(12) United States Patent
Beale et al.

(10) Patent No.: US 9,078,671 B2
(45) Date of Patent: Jul. 14, 2015

(54) SURGICAL TOOL

(75) Inventors: Jeff Beale, Bartlett, TN (US); Harold Taylor, Memphis, TN (US); Oivind Brockmeier, Somerville, MA (US); Jared Alden Judson, Topsfield, MA (US); Jeffrey R. Chapin, Jamaica Plain, MA (US); Timothy Proulx, Nashua, NH (US); Ari Tao Adler, Cambridge, MA (US); Jason Robinson, Tewksbury, MA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1036 days.

(21) Appl. No.: 12/104,604

(22) Filed: Apr. 17, 2008

(65) Prior Publication Data

US 2009/0264940 A1 Oct. 22, 2009

(51) Int. Cl.

| | |
|---|---|
| A61F 2/46 | (2006.01) |
| A61B 17/16 | (2006.01) |
| A61B 5/04 | (2006.01) |
| A61B 17/88 | (2006.01) |
| B25B 21/00 | (2006.01) |
| B25B 23/00 | (2006.01) |
| B25F 5/00 | (2006.01) |
| A61B 19/00 | (2006.01) |
| A61B 17/00 | (2006.01) |

(52) U.S. Cl.
CPC ......... *A61B 17/1628* (2013.01); *A61B 5/04001* (2013.01); *A61B 17/162* (2013.01); *A61B 17/1624* (2013.01); *A61B 17/8875* (2013.01); *A61B 19/54* (2013.01); *B25B 21/00* (2013.01); *B25B 21/002* (2013.01); *B25B 23/00* (2013.01); *B25F 5/00* (2013.01); *A61B 17/1671* (2013.01); *A61B 19/5244* (2013.01); *A61B 2017/00039* (2013.01); *A61B 2017/00477* (2013.01); *A61B 2017/00876* (2013.01); *A61B 2019/5483* (2013.01)

(58) Field of Classification Search
CPC ............... A61B 17/16; A61B 17/1615; A61B 17/1622; A61B 17/1628
USPC ............. 606/79, 80, 81, 104, 96, 86 R, 86 A; 173/217, 216; 310/47–50
See application file for complete search history.

(56) References Cited

U.S. PATENT DOCUMENTS

| | | | |
|---|---|---|---|
| 2,979,089 A | 4/1961 | Piesker | |
| 5,207,697 A * | 5/1993 | Carusillo et al. | ............. 606/167 |
| 5,251,707 A | 10/1993 | Grahl | |

(Continued)

OTHER PUBLICATIONS

International Searching Authority, International Search Report and Written Opinion, Jul. 17, 2009.

*Primary Examiner* — Kevin T Truong
*Assistant Examiner* — Christine Nelson
(74) *Attorney, Agent, or Firm* — Sorell Lenna & Schmidt LLP

(57) ABSTRACT

A tool for use during surgery includes a housing including a distal end and a proximal end, a motor disposed within the housing, and an output shaft having a proximal end connected to the motor and a distal end extending from the distal end of the housing. The tool further includes a battery pack contained within the housing, and a passage extending from the distal end to the proximal end of the housing through the output shaft and the battery pack, wherein the passage is defined by an interior surface of the output shaft and a channel through the battery.

24 Claims, 35 Drawing Sheets

(56) References Cited

U.S. PATENT DOCUMENTS

| | | |
|---|---|---|
| 5,603,179 A | 2/1997 | Adams |
| 5,807,313 A | 9/1998 | Delk |
| 5,997,538 A | 12/1999 | Asnis |
| 6,199,642 B1 | 3/2001 | Becker et al. |
| 6,631,579 B1 | 10/2003 | Lauster |
| 6,746,153 B2 | 6/2004 | Del Rio |
| 7,043,961 B2 | 5/2006 | Pandey |
| 7,137,324 B2 | 11/2006 | Ludwig et al. |
| 7,165,663 B2 | 1/2007 | Donner |
| 7,296,500 B1 | 11/2007 | Martinelli |
| 2003/0216743 A1 | 11/2003 | Hoffman |
| 2004/0204658 A1 | 10/2004 | Dietz |
| 2006/0025703 A1 | 2/2006 | Miles |
| 2006/0041241 A1 | 2/2006 | Herndon |
| 2006/0111723 A1 | 5/2006 | Chapolini |
| 2006/0173521 A1 | 8/2006 | Pond |
| 2006/0178593 A1 | 8/2006 | Neubardt |
| 2006/0271096 A1 | 11/2006 | Hamada |
| 2007/0021752 A1 | 1/2007 | Rogers |
| 2007/0100334 A1* | 5/2007 | McFarlin et al. ............... 606/45 |
| 2007/0260257 A1 | 11/2007 | Phan |
| 2007/0287910 A1 | 12/2007 | Stallings |
| 2008/0077158 A1 | 3/2008 | Haider |

* cited by examiner

SURGICAL TOOL

BACKGROUND

1. Field of the Disclosure

This disclosure is directed to a surgical tool, and more particularly directed to a surgical tool for inserting implantable devices within the body.

2. Description of the Related Art

There are a variety of different spinal diseases, such as scoliosis, as well as others, which may be cured or mitigated by implantation of certain devices. Such devices can include articles and mechanisms useful for repairing damaged portions of the spine, stabilizing portions of the spine, or changing the position of the spine to a more healthy state. For example, rod and anchor systems are commonly employed when portions of the spine need to be realigned, such as in patients with abnormal curvatures, wherein the rod provides rigid support for urging the spine to a more healthy position.

The implantation of rod and anchor systems typically involves the fixation of a plurality of screws within particular portions of a patient's spine. For example, it is typical for a surgeon to implant a series of anchors or set screws into a patient's spine and couple these screws to a rigid rod such that the spine is urged to align with the rod. Depending upon the severity of the curvature and the surgical procedure chosen by the patient and surgeon, the process of implanting the anchors and aligning them with a rod can be a time consuming and daunting procedure, with surgeries commonly taking hours if not longer. Such a process is particularly draining because the current state of the art with regard to the tools used to affixing the anchors within the spine is a generally manual process including the use of powerless, hand-held tools.

DETAILED DESCRIPTION

Description of Relevant Anatomy

Figure 1:
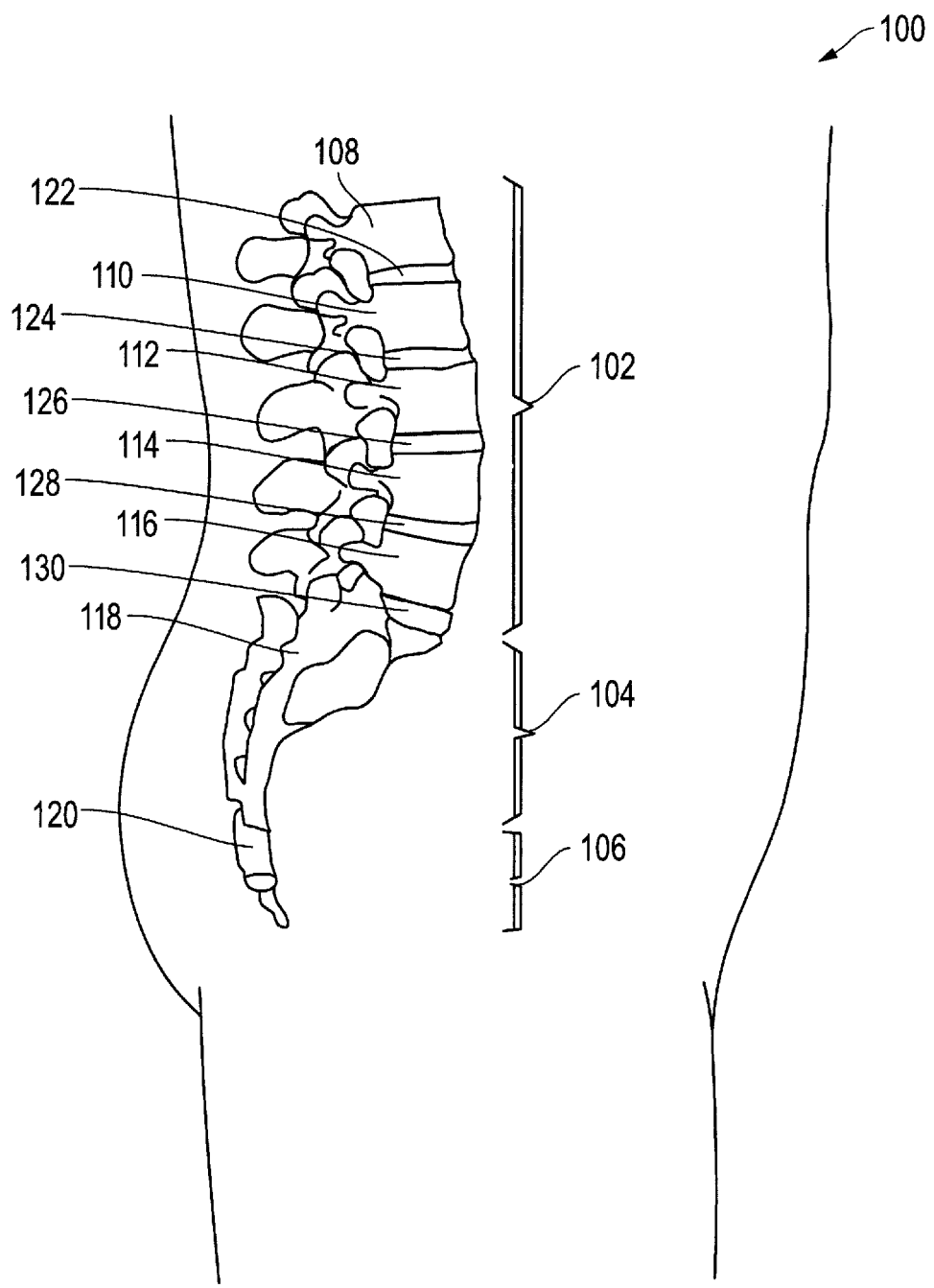
FIG. 1 includes a lateral view of a portion of a vertebral column.

Referring initially to FIG. 1, a portion of a vertebral column, designated 100, is shown. As depicted, the vertebral column 100 includes a lumbar region 102, a sacral region 104, and a coccygeal region 106. The vertebral column 100 also includes a cervical region and a thoracic region. For clarity and ease of discussion, the cervical region and the thoracic region are not illustrated.

As illustrated in FIG. 1, the lumbar region 102 includes a first lumbar vertebra 108, a second lumbar vertebra 110, a third lumbar vertebra 112, a fourth lumbar vertebra 114, and a fifth lumbar vertebra 116. The sacral region 104 includes a sacrum 118. Further, the coccygeal region 106 includes a coccyx 120.

As depicted in FIG. 1, a first intervertebral lumbar disc 122 is disposed between the first lumbar vertebra 108 and the second lumbar vertebra 110. A second intervertebral lumbar disc 124 is disposed between the second lumbar vertebra 110 and the third lumbar vertebra 112. A third intervertebral lumbar disc 126 is disposed between the third lumbar vertebra 112 and the fourth lumbar vertebra 114. Further, a fourth intervertebral lumbar disc 128 is disposed between the fourth lumbar vertebra 114 and the fifth lumbar vertebra 116. Additionally, a fifth intervertebral lumbar disc 130 is disposed between the fifth lumbar vertebra 116 and the sacrum 118.

In a particular embodiment, if one of the intervertebral lumbar discs 122, 124, 126, 128, 130 is diseased, degenerated, or damaged or if one of the zygapophyseal joints is diseased, degenerated or damaged, that disc or joint can be at least partially treated with an implanted device according to one or more of the embodiments described herein.

Figure 2:
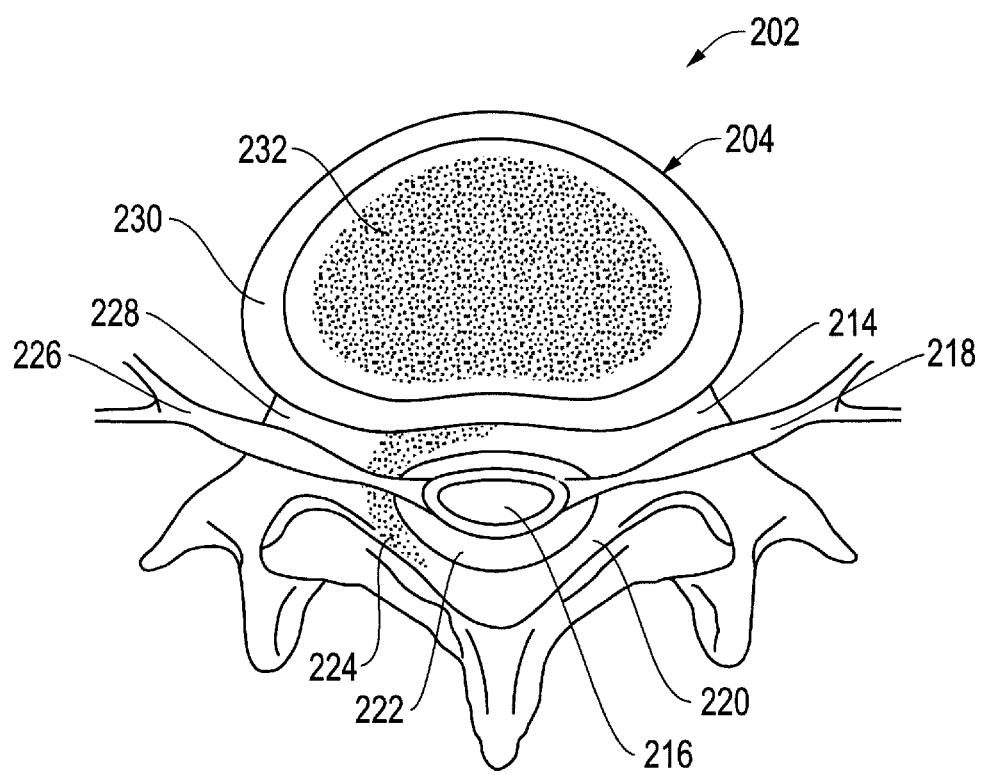
FIG. 2 includes a top plan view of a vertebrate.

Referring to FIG. 2, a top plan view of a vertebra is illustrated. As shown, the vertebral body 204 of the inferior vertebra 202 includes a cortical rim 230 composed of cortical bone. Also, the vertebral body 204 includes cancellous bone 232 within the cortical rim 230. The cortical rim 230 is often referred to as the apophyseal rim or apophyseal ring. Further, the cancellous bone 232 is generally softer than the cortical bone of the cortical rim 230.

As illustrated in FIG. 2, the inferior vertebra 202 further includes a first pedicle 214, a second pedicle 228, a first lamina 220, and a second lamina 224. Further, a vertebral foramen 222 is established within the inferior vertebra 202. A spinal cord 216 passes through the vertebral foramen 222. Moreover, a first nerve root 218 and a second nerve root 226 extend from the spinal cord 216. In particular, the first pedicle 214 and the second pedicle 228 represent regions of the spine in which surgeons often choose to implant anchors, such as bone screws for attaching an anchor and rod system to the spine. Notably, given the proximity to the spinal cord 216 and other significant anatomical portions, the implantation of such screws is a delicate and precise procedure requiring tools significantly different than available to the general public.

The vertebrae that make up the vertebral column have slightly different appearances as they range from the cervical region to the lumbar region of the vertebral column. However, all of the vertebrae, except the first and second cervical vertebrae, have the same basic structures, e.g., those structures described above in conjunction with FIG. 2. The first and second cervical vertebrae are structurally different than the rest of the vertebrae in order to support a skull.

FIGS. 3-11 provide illustrations of the surgical tool or portions of the surgical tool in accordance with embodiments. In particular, FIGS. 3-11 provide embodiments regarding a surgical tool configured for affixing orthopedic anchors, intervertebral bodies such as threaded cages, and screws in bone or spaces between bones, such as between vertebrae. In particular, the surgical tool of the present description is suitable for tapping bone, including using a tapper bit head to form a pilot hole within the bone. Moreover, the present surgical tool is particularly well-suited for driving a screw into bone using a screw driver bit head. In particular, the present surgical tool facilitates initial driving of a screw into bone using the power of the tool, and then optionally, manually finishing the driving process of setting the screw using the surgical tool as it has improved feel and ratcheting capabilities.

Figure 3:
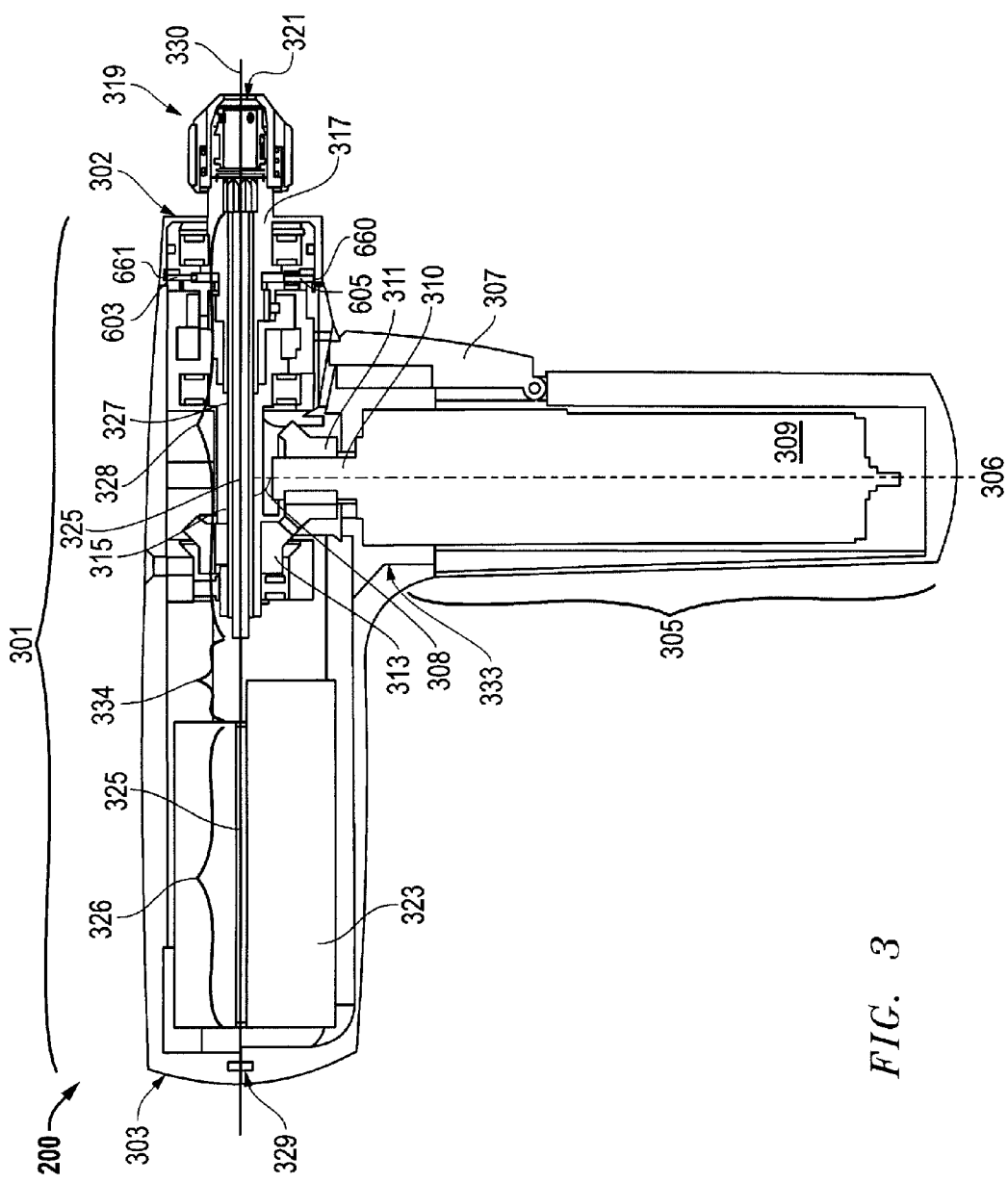
FIG. 3 includes a cross-section illustration of a surgical tool in accordance with an embodiment.

Referring to FIG. 3, a cross-sectional illustration of the surgical tool is illustrated in accordance with an embodiment. As illustrated, the surgical tool 300 includes a housing 301 extending from a proximal end 303 to a distal end 302 opposite the proximal end 303. In general reference to the operation of the surgical tool 300, the housing 301 includes a motor 309 disposed within a handle 305 and coupled to the housing 301. A trigger 307 is coupled to the handle 305 and is electrically coupled to the motor 309 such that upon depression of the trigger 307 by a user the motor is engaged. The motor 309 includes a drive shaft 310 extending from the motor 309 and coupled to a transfer mechanism 311. In accordance with one embodiment, the transfer mechanism 311 includes a bevel gear. Additionally, in one embodiment, the transfer mechanism 311 can be coupled to a second transfer mechanism 313, which can include a second bevel gear, which in turn is coupled to an output shaft 315. Accordingly, engagement of the trigger 307 can include engagement of the motor to turn the transfer mechanism 311, and correspondingly rotate the second transfer mechanism 313, thereby causing rotation of the output shaft 315. Accordingly, a tool 300 is provided that is capable of providing a rotational force to a work piece.

Additionally as will be illustrated in other embodiments, the output shaft 315 can be separated into various sections including a proximal output shaft portion 315 which is coupled to a distal output shaft portion 317.

In accordance with an embodiment, the housing 301 is connected to a handle 305 extending at an angle from the housing 301 and coupled to the housing 301 between the proximal end 303 and the distal end 302. In accordance with another embodiment, the handle 305 extends from the housing 301 at a substantially orthogonal angle 308 as defined between a longitudinal axis 306 of the handle 305 relative to a longitudinal axis 330 of the housing 301. In accordance with another embodiment, the angle 308 can be a non-orthogonal angle such that the handle 305 is angled relative to the housing 301. As such, in embodiments utilizing an angle 308 that is substantially non-orthogonal, the handle 305 has a forward rake design, such that a proximal end 333 of the handle 305 is angled toward the distal end 302 of the housing 301. Accordingly, in such embodiments, the angle 308 can be acute, such as less than about 80°, such as less than 75°, or even less than 60°. Still, for embodiments utilizing a non-orthogonal angle connection between the handle 305 and housing 301, the angle 308 can be within a range between about 55° and about 85°.

Moreover, in accordance with another embodiment, the surgical tool 300 can include a chuck 319 coupled to the housing 301 at the distal end 302. According to a particular embodiment, the chuck 319 can include an opening 321 configured to engage a bit shaft. In accordance with a particular embodiment, the chuck 319 can include a quick-connect adapter, configured to engage a proximal end of a bit shaft via a snap-fit connection. As will be appreciated, such a quick-connect adapter can include biasing members, or channels for receiving bearings to accomplish the snap-fit or quick-connect coupling.

In accordance with a particular embodiment, the surgical tool 300 includes a passage 325 extending through the housing 301 from the distal end 302 to the proximal end 303. As illustrated, the passage 325 can extend through the interior of the output shaft 315 and through the interior of a battery pack 323 and exit the housing 301 at an opening 329 adjacent to the proximal end 303. In accordance with one embodiment, the passage 325 can have a generally circular cross-sectional contour including a diameter of at least of about 1 mm. In accordance with another embodiment, the diameter of the passage can be greater, such as at least about 1.5 mm or at least about 2 mm. Still, another embodiment the diameter of the passage 325 is generally limited such that is not greater than about 10 mm, such as not greater than about 8 mm, or even not greater than about 5 mm. In one particular embodiment, the passage has a diameter within a range between about 2 mm and about 5 mm.

According to one embodiment, the passage 325 generally has a length between the distal end 302 and the proximal end 303 of the housing 301, such that the passage extends for a length of the output shaft 315. In one embodiment, the passage 325 has a length of at least about 10 cm. In accordance with another embodiment, the passage 325 has a length of at least about 12 cm, such as at least about 15 cm, or even at least about 20 cm. Generally, in certain embodiments, the length of the passage 325 is not greater than about 25 cm, and more particularly within a range between about 10 cm and about 25 cm.

In accordance with another embodiment, the passage 325 can be segmented. As illustrated in FIG. 3, the passage 325 includes two discrete passage portions including a first portion 328 disposed within the interior of the output shaft 315 and a second portion 326 extending through the interior of the battery pack 323, wherein the first portion 328 and the second portion 326 are axially separated by an opening 334. According to one embodiment, the first portion 328 of the passage 325 has a length extending through the interior of the output shaft 315 of at least about 5 cm. In accordance with another embodiment, the length of the first portion 328 is at least about 8 cm or as at least about 10 cm. Generally, in certain embodiments, the length of the first portion 328 of the passage 325 is not greater than about 15 cm, and more particularly within a range between about 5 cm and about 12 cm.

In referenced to the second portion 326 of the passage 325 extending through the battery pack 323, this portion can have a length that is the same as the length of the first portion 328 of the passage 325. However, in accordance with a particular embodiment, the length of the second portion 326 of the passage 325 can be less than the length of the first portion 328 of the passage 325. In one embodiment, the length of the second portion 326 of the passage 325 extending through the battery pack 323 has a length that is at least about 5 cm, such as at least 8 cm, or at least about 10 cm. In accordance with another particular embodiment, however, the length of the passage portion 326 extending through the battery pack 323 is generally not greater than about 15 cm, and more particularly within a range between about 5 cm and about 12 cm.

While FIG. 3 illustrates that the passage 325 can be segmented including a first portion 328 and a second portion 326, it will be appreciated that the passage can be further segmented into three portions, or even more portions. Still, according to another embodiment, the passage 325 can be a single, sealed passage extending for the entire length of the housing 301 between the proximal end 303 and the distal end 302 without any openings. Still, according to other embodiments, the passage can have alternative designs. For example, in one embodiment the passage 325 can be a channel including an opening that extends substantially along the longitudinal length of the passage 325. In another embodiment, the passage 325 can include a series of openings or perforations extending along the length of passage 325.

In accordance with another embodiment, the passage 325 can include an electrically insulated liner 327 extending along the interior surface of the passage 325 and extending for a portion of the passage 325. The electrically insulating liner 327 can facilitate electrical insulation between the passage 325 and surrounding components contained within the housing 301. In accordance with a particular embodiment, the electrically insulated liner 327 can extend for a portion of the length of the passage 325. As such, in one particular embodiment, at least 25% of the length of the passage 325 can include the electrically insulating liner 327. In another embodiment, at least 30%, such as at least 50%, or at least 75% of the length of the passage 325 includes the electrically insulating liner 327. In one particular embodiment, the entire length of the passage 325 can include the electrically insulating liner 327.

In reference to embodiments wherein the passage 325 is segmented, one of the portions can include the electrically insulating liner 327 while the second portion may not include the electrically insulating liner 327. For example, as illustrated in FIG. 3, the first portion 328 includes an electrically insulating portion 327 while the second portion 326 of the passage 325 does not include an electrically insulating liner 327. However, it is particularly suitable that at least a portion of the passage 325 extending through the battery pack 323 include the electrically insulating liner 327.

Materials suitable for forming the electrically insulating lining 327 can generally include dielectric materials. Various dielectric materials can include ceramics or polymers. According to a particular embodiment, the electrically insulating lining 327 includes a polymer material. In one embodiment, suitable polymer materials can include polyurethane materials, polyolefin materials, polyether materials, silicone materials, or a combination thereof. Further, the polyolefin materials can include polypropylene, polyethylene, halogenated polyolefin, fluoropolyolefin, or a combination thereof. The polyether materials can include polyetherketone (PEK), polyetheretherketone (PEEK), polyetherketoneketone (PEKK), polyaryletherketone (PAEK), or a combination thereof. In one particular embodiment, the ring body 1500 is made entirely of PEEK.

As further illustrated in FIG. 3, the passage 325 can extend along a single axis 330 of the housing 301 from the distal end 302 to the proximal end 303. Accordingly, in one embodiment, the passage 325 can have a substantially linear shape such that it may include no turns, which in turn may facilitate the passage of articles therethrough. Alternatively, in another embodiment, the passage includes at least one turn such that it extends along more than one axis. In still another embodiment, the housing can further include additional passages extending from the passage 325 to different parts of the housing 301.

In further reference to FIG. 3, a portion of the housing 301 can include a sealed compartment. In a particular embodiment, the seal compartment can include the motor 309. The sealed compartment within the housing can be facilitated by positioning of gaskets, such as for example, o-rings at particular locations within the housing. Moreover, provision of a sealed portion within the housing including the motor 309 facilitates sterilizing of the surgical tool 300.

In further reference to sterilizing of the surgical tool 300, the housing 301 and components contained therein can be made of autoclavable materials. As used herein, reference to autoclavable materials include materials capable of withstanding temperatures in excess of 121° C. and pressures in excess of 15 PSIA. As such, in one particular embodiment, suitable autoclavable materials can include metal, metal alloys, or polymers. According to a particular embodiment, the housing 301 and components contained within the housing 301 can include metals such as titanium, aluminum, magnesium, iron, cobalt, nickel, tungsten, steel, or any combination thereof. In a more particular embodiment, certain components can be made of a polymer materials, including for example polyurethane materials, polyolefin materials, polyether materials, silicone materials, or a combination thereof. Further, the polyolefin materials can include polypropylene, polyethylene, halogenated polyolefin, fluoropolyolefin, or a combination thereof. The polyether materials can include polyetherketone (PEK), polyetheretherketone (PEEK), polyetherketoneketone (PEKK), polyaryletherketone (PAEK), or a combination thereof. Other suitable materials can include styrenes (e.g., acrylonitrile butadiene styrene), polycarbonates, polysulphones, and carbon fiber, for example, carbon fiber-reinforced composites.

In reference to another embodiment, portions of the housing 301 can include electromagnetic shielding. In one embodiment, the electromagnetic shielding can include metal meshing disposed around particular components within the housing 301. In accordance with a particular embodiment, the battery pack 323 and motor 309 can include electromagnetic shielding provided around at least a portion of the outer surface, and more particularly substantially surround the outer surfaces. Electromagnetic shielding of the components, particularly of the battery pack 323 and motor 309, facilitates efficient and reliable use of the surgical tool 300 in an environment such as an operating room wherein many electrical machines are used and electromagnetic interferences may occur.

In reference to another particular embodiment, the surgical tool 300 can further include a torque limiter, which may be selectable by the user. According to one embodiment, the surgical tool 300 can include a microprocessor electrically coupled to the motor and the battery pack wherein the microprocessor controls the current from the battery to the motor 309, thereby controlling the torque output of the motor 309. In accordance with an alternative embodiment, the surgical tool 300 can include a mechanical torque limiter coupled to the motor 309 and output shaft 315. On such suitable torque limiter can include bearings and a clutch wherein if a particular torque is exceeded a first portion of the output shaft can be decoupled from a second portion of the output shaft.

Figure 4:
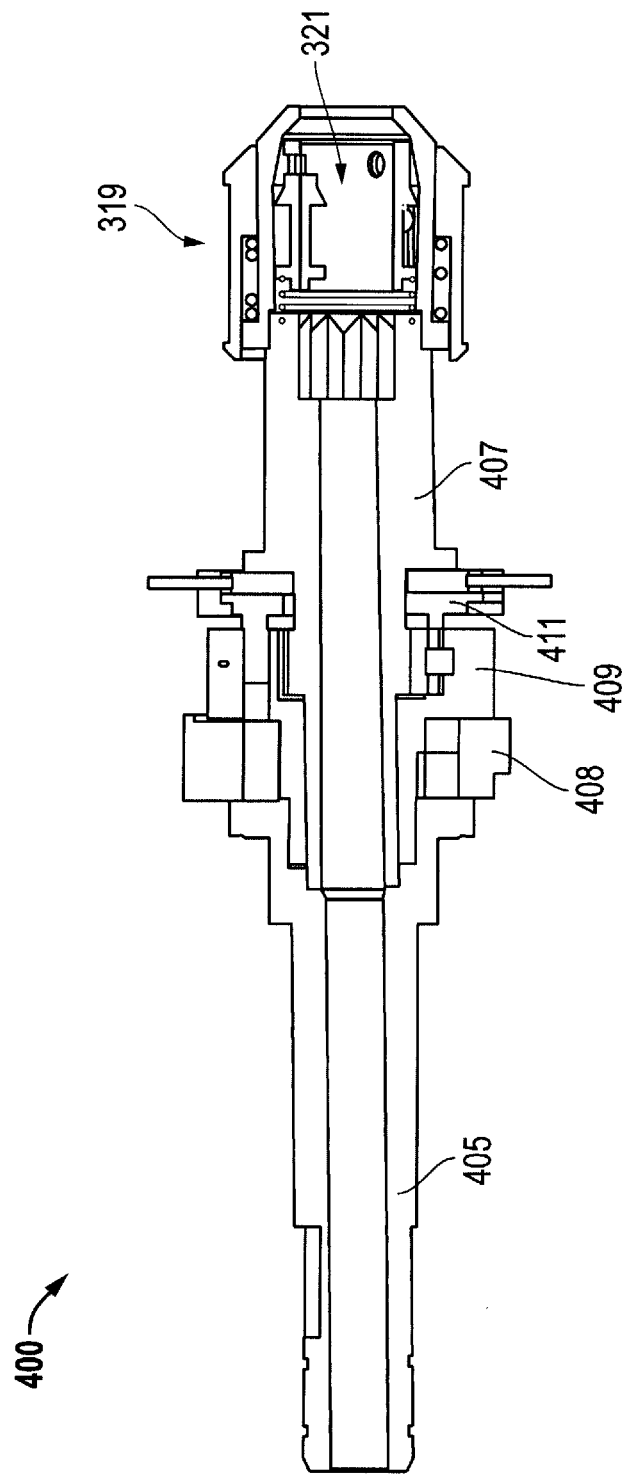
FIG. 4 includes a cross-sectional illustration of a portion of a surgical tool in accordance with an embodiment.

Referring to FIG. 4, a cross-sectional illustration of the output shaft of the surgical tool is provided in accordance with an embodiment. As illustrated, the output shaft 400 is segmented such that is has a proximal portion 405 coupled to a distal portion 407. In accordance with a particular embodiment, the proximal portion 405 of the output shaft 400 is coupled to the distal portion 407 via a jam ring 408, which is coupled to a ratcheting mechanism 409, which in turn is coupled to a member 411. The combination of these components will be described in further detail in subsequent figures and the combination of these components (i.e., 408, 409 and 411) facilitate ratcheted rotation of the output shaft 400 such that rotational movement of the output shaft 400 can be finely controlled, which is particularly suitable for surgical procedures.

Figure 5:
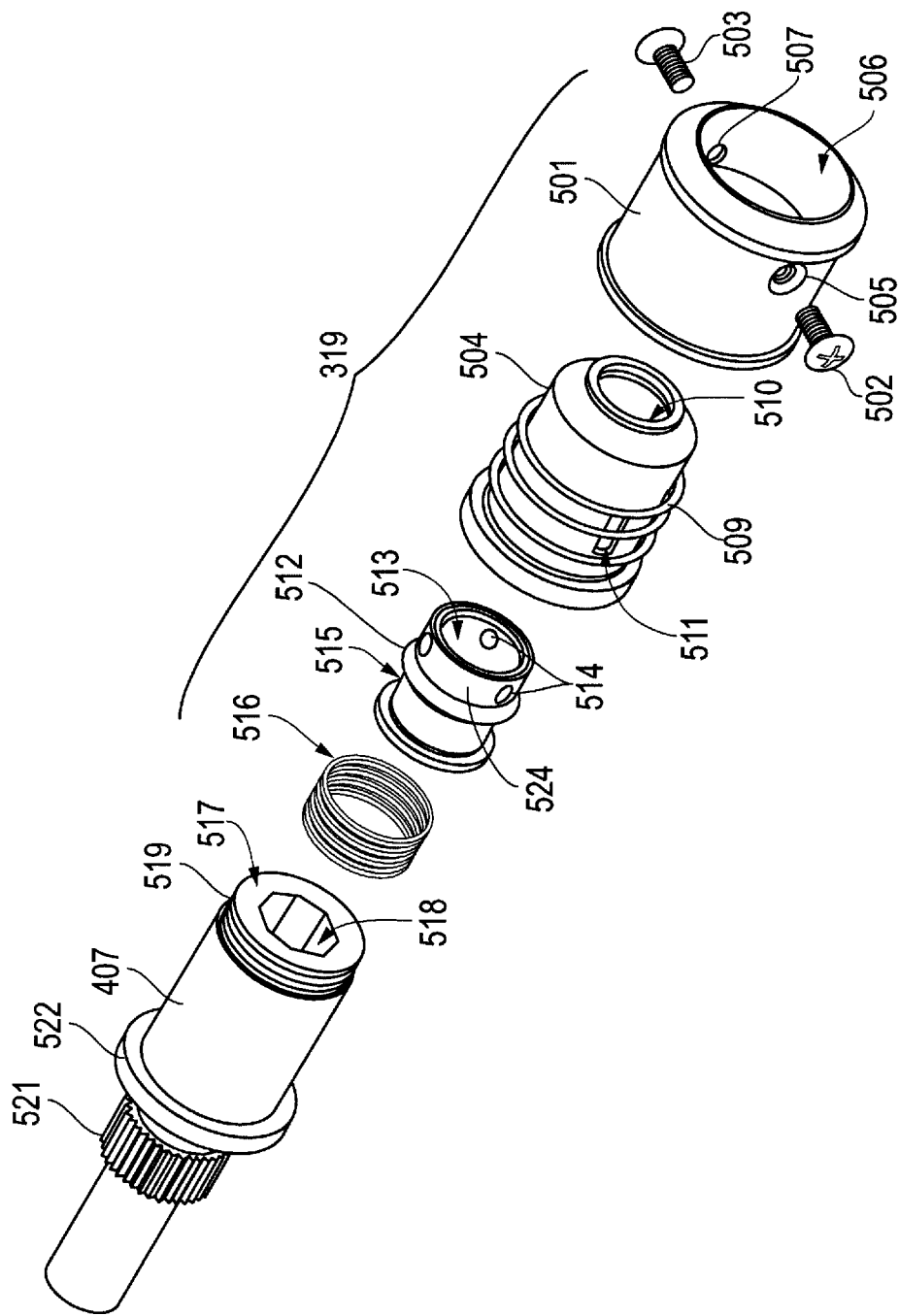
FIG. 5 includes a perspective view of a portion of a surgical tool in accordance with an embodiment.

FIG. 5 includes a perspective view of the output shaft of the surgical tool as previously illustrated in FIG. 4. Referring to FIG. 5, a perspective view of the distal portion of the output shaft of the surgical tool is provided in accordance with an embodiment. As illustrated, FIG. 5 includes a chuck 319 having an outer sleeve portion 501 coupleable to a sleeve portion 504, which is coupleable to an inner sleeve portion 512, which in turn is coupleable to a biasing member 516. The outer sleeve portion 501 provides the outer surface of the chuck 319 and houses the sleeve portion 504 and the inner sleeve portion 512. As illustrated, the outer sleeve portion 501 can include an opening 506 configured to allow extension of sleeve portion 504 therethrough for engagement of a bit shaft. The outer sleeve portion 501 includes openings 505 and 507 configured to engage screws 502 and 503 that are configured to couple the outer sleeve portion 501, sleeve portion 504, and the inner sleeve portion 512.

According to the illustrated embodiment of FIG. 5, the sleeve portion 504 of the chuck 319 includes an opening 510 configured to extend through the opening 506 of the outer sleeve portion 501 and engage a bit shaft. In accordance with a particular embodiment, the sleeve portion 504 is configured to slide within and engage a portion of the inner surface of the outer sleeve portion 501. Moreover, sleeve portion 504 includes an opening 511 axially located along the length of sleeve portion 504 and configured to engage with the screws 502 and 503 thereby coupling the sleeve portion 504 with the outer sleeve portion 501. Moreover, the sleeve portion 504 can include a biasing member 509, such as a coiled spring, configured to engage an inner surface of the outer sleeve portion 501 and bias the outer sleeve portion 501 against the sleeve portion 504.

The chuck 319 further includes an inner sleeve portion 512 configured to engage the inner surface of sleeve portion 504. According to the illustrated embodiment, the inner sleeve portion 512 includes an opening 513 configured to align with the opening 510 of sleeve portion 504, the opening 506 of outer sleeve portion 501, and configured to receive a bit shaft. According to a particular embodiment, the inner sleeve portion 512 includes openings 514 displaced circumferentially around a collar portion 524 of the inner sleeve portion 512. The openings 514 are configured to couple with bearings or other surfaces along a bit shaft for a quick-connect coupling. Additionally, the inner sleeve portion 512 includes a channel region 515 extending circumferentially around the outer surface of the inner sleeve portion 512 and configured to engage with the screws 502 and 503 thereby fixably attaching the inner sleeve portion 512 within the sleeve portion 504 and further within the outer sleeve portion 501.

The chuck 319 further includes a biasing member 516, such as a coiled spring, configured to couple between a front surface of the distal portion 407 of the output shaft and a back surface of the inner sleeve portion 512. The resilient biasing member 516 facilitates decoupling of a bit shaft from the chuck 319 by compressing the inner sleeve portion 512 axially toward the face portion 517 of the distal portion 407 of the output shaft thereby enabling one-handed decoupling of a bit shaft.

The distal portion 407 of the output shaft includes an opening 518 configured to receive a portion of a bit shaft. As illustrated, the opening 518 can have a cross-sectional contour configured to engage a proximal end of a bit shaft, such as having a hexagonal cross-sectional contour as illustrated. Moreover, the distal portion 407 of the output shaft includes threading 519 configured to engage threads within an inner surface of the inner sleeve portion 504 and fixably couple the chuck 319 on the end of the distal portion 407 of the output shaft. According to another embodiment, the distal portion of the output shaft 407 further includes a lip 522 configured to engage and directly contact components further illustrated in FIG. 6.

Figure 6A:
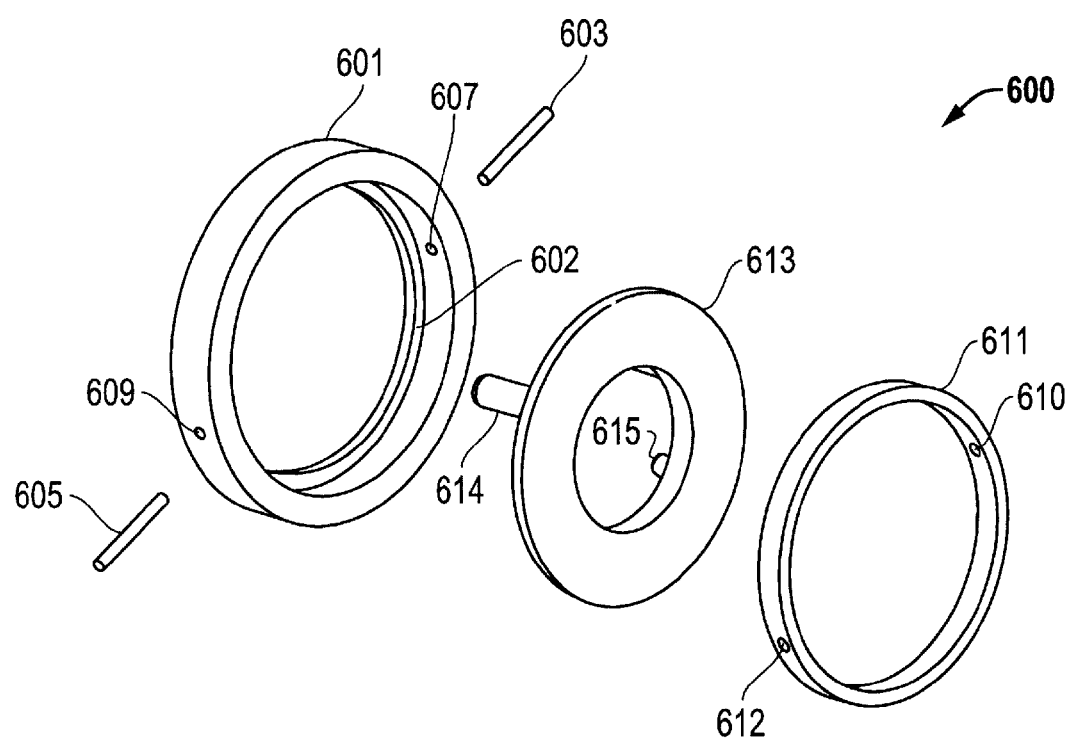
FIG. 6A includes a perspective view of a direction selection assembly of a surgical tool in accordance with an embodiment.
Figure 6B:
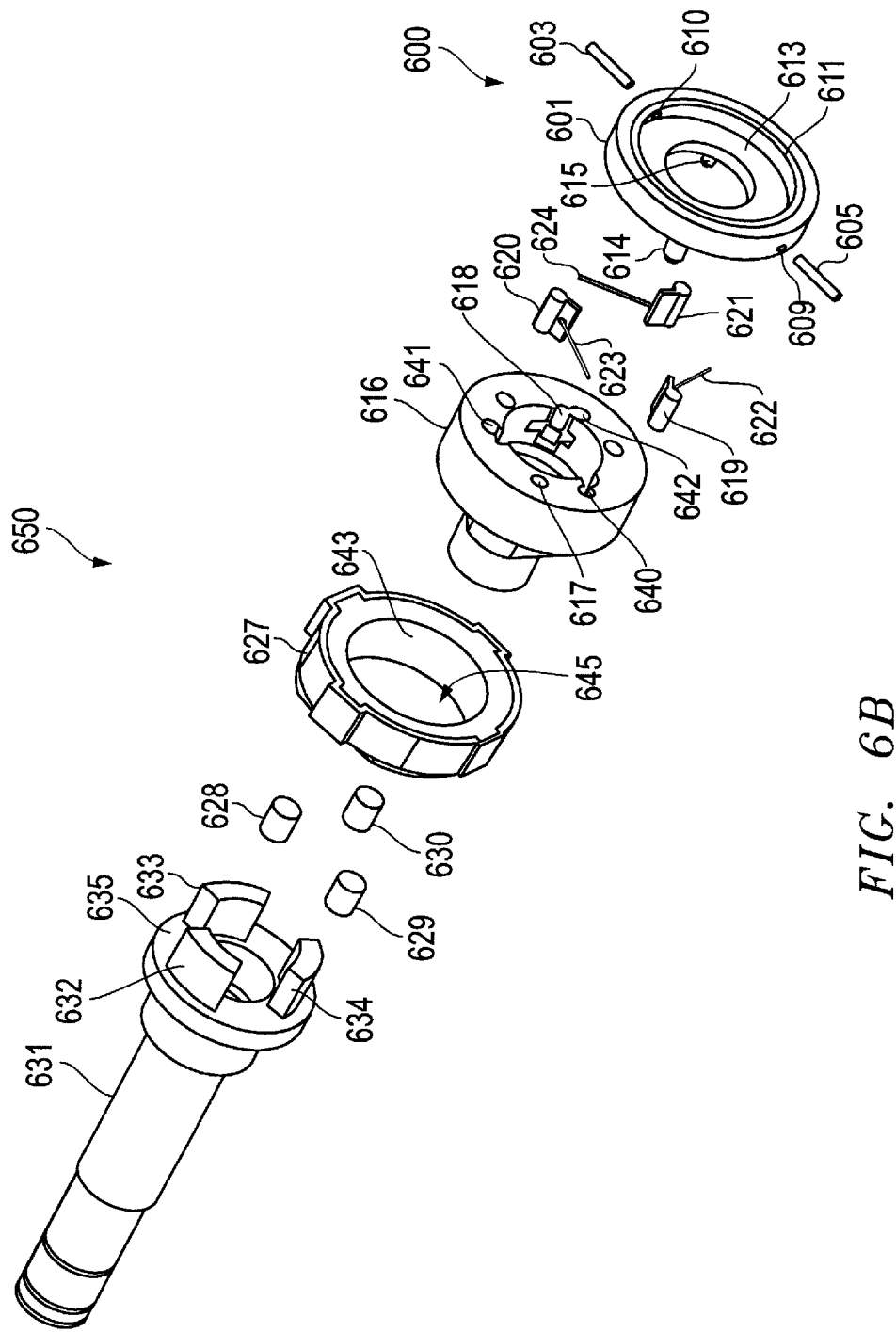
FIG. 6B includes a perspective view of an anti-backdrive assembly and a direction selection assembly of a surgical tool in accordance with an embodiment.

Moreover, the distal portion 407 of the output shaft can include a toothed surface 521 extending around the circumference of the outer surface and configured to engage components further illustrated in FIG. 6B. In particular, the teeth 521 facilitate coupling of a ratcheting mechanism (see FIG. 6B) for fine control. As such, in one embodiment, the toothed surface 521 includes at least about 20 total teeth extending around the circumference of the distal portion 407. According to a particular embodiment, the toothed surface 521 includes at least about 25 total teeth, or even at least about 30 total teeth. In a more particular embodiment, the toothed surface includes between about 30 and about 50 total teeth on the toothed surface 521. The provision of a toothed surface 521 having such numbers of total teeth facilitates fine ratcheting control, which is particularly suitable for use during surgical procedures.

FIGS. 6A and 6B include a perspective views of a portion of the output shaft 600 for use in the surgical tool in accordance with an embodiment. Generally, FIG. 6A illustrates a direction selection assembly 600 used to select between a forward and reverse drive positions. FIG. 6B generally illustrates components of the ratcheting mechanism and an anti-backdrive assembly. Referring to FIG. 6A, a sleeve 601 is provided having openings 607 and 609 configured to engage pins 603 and 605. The direction selection assembly 600 further includes a member 613 configured to be disposed within the sleeve 601 such that it abuts the inner lip 602 of the sleeve 601. The member 613 further includes one or more protrusions or pins extending from a rear surface and configured to engage portions of an anti-backdrive device illustrated in FIG. 6B. In one embodiment, the pin 614 of the member 613 is configured to engage openings within the anti-back drive device, thereby acting as a clutch and capable of locking pawls (illustrated in FIG. 6B) within the anti-backdrive device in a particular location.

Moreover, the member 613 includes at least one pin 615 that is shorter in length than the pin 614 and particularly configured to selectively engage openings within the anti-backdrive device to engage or disengage the ratcheting capabilities. In accordance with one particular embodiment, the member 613 includes three pins having the same length of pin 614 and three pins having a shorter length, such as pin 615 extending from the back surface of the member 613.

As further illustrated in FIG. 6A, the direction selection assembly 600 further includes a sleeve 611 having openings 610 and 612 extending through the width of the body. The sleeve 611 is configured to fit within the inner diameter of the sleeve 601 and hold the member 613 within the sleeve 601. In accordance with one embodiment, while the member 613 is within the sleeve 601 it is generally free to rotate. Moreover, the openings 610 and 612 are configured to engage the pins 603 and 605, such that the pins 603 and 605 extend through the openings 610 and 612 and are flush with the inner surface of the sleeve 611.

In accordance with one embodiment, the pins 603 and 605 are configured to engage channels or slots (660 and 661 in FIG. 3) along the inner surface of the housing. The pins 603 and 605 can freely slide within the channels and upon movement of the pins 605 and 605 from one position to another, the pin 615 of the member 613 can engage or disengage an opening on the anti-backdrive device and accordingly select or deselect actuation of the ratcheting mechanism. In accordance with another embodiment, the pins 603 and 605 can be engaged within cam slots inside a cap that is keyed to the housing to facilitate direction selection control.

FIG. 6B includes a perspective view of the components of an anti-backdrive assembly and the direction selection assembly. As illustrated, the anti-backdrive assembly 650 is configured to engage the direction selection assembly 600. The anti-backdrive assembly 650 includes anti-backdrive device 616, which includes openings 617 and 618 configured to engage pins 614 and 615 respectively of the direction selection assembly 600 in certain situations. The anti-backdrive device 616 further includes openings 640, 641, and 642 for housing pawls 619, 620, and 621 and the corresponding biasing members 622, 623, and 624 respectively. According to a particular embodiment, the ratcheting action of the anti-back drive device 616 is facilitated by pawls 619, 620, and 621 (619-621) configured to be disposed within openings 640, 641, and 642, respectively. Additionally, in one particular embodiment, the pawls 619-621 are resiliently biased against a portion of the anti-backdrive device 616 such that they extend into the opening and are configured to engage teeth (previously illustrated as teeth 521 in FIG. 5) by biasing members 622, 623, and 621.

As further illustrated in FIG. 6B, the anti-backdrive assembly 650 further includes a jam ring 627 configured to engage a surface of the anti-backdrive device 616. Moreover, as further illustrated, rollers 628, 629, and 630 are configured to be disposed and coupled with an inner surface 643 of the jam ring 627. In one embodiment, a proximal portion of the output shaft 631 includes arms 632, 633, and 634 (632-634) axially extending from a distal surface 635 which are configured to extend into the opening 645 of the jam ring 627 and engage a portion of the anti-back drive device when the motor is providing the torque to the proximal portion of the output shaft 631. The coupling between the arms 632-634 with portions of the anti-backdrive device 616 facilitates transfer of torque from the proximal portion of the output shaft 631 to the distal portion of the output shaft (407 in FIG. 5) when the motor is providing the torque. Alternatively, if torque is applied to the proximal portion 600 from the distal portion of the output shaft 407 (i.e., not from the motor), the jam ring 627 facilitates decoupling of the motor from the output shaft to avoid damage to the motor. In particular, in situations where torque is applied to the portion 600 from the opposite end of the motor, the rollers 628-630 lock against the inner surface of the jam ring 627 and decouple the distal portion 407 of the output shaft from the proximal portion 631.

In operating the surgical tool in a forward direction under the power of the motor, the pins 603 and 605 move in slots or channels within the housing and pin 615 of the member 613 is disengaged from the opening 618 in the anti-backdrive device 616. The proximal portion of the output shaft 631 rotates clockwise and the arms 632-634 engage and contact surfaces of the anti-backdrive device 616 while the rollers 628-630 spin freely within the inner surface 643 of the jam ring 627. The rotational motion is imparted to the distal portion of the output shaft 407 and it rotates while the pawls 619-621 engage the teeth of the toothed surface providing torque transfer to distal end 600.

The surgical tool can be operated in a forward direction under manual power up to a specific torque, which may be selected by the user or pre-set by the manufacturer upon assembly. During forward manual operation, if the specific torque is exceeded the output shaft can be rotated in reverse or backdrive. Upon exceeding the specified torque, the proximal portion of the output shaft 631 can reverse rotation for a short distance until the arms 632-634 and rollers 628-630 lock up in the inner surface 643 of the jam ring 627. Since, according to one embodiment, the jam ring 627 is locked to the housing of the tool, the backdrive is stopped and manual forward driving of the output shaft can continue. It should be noted, that in this instance, the pawls 619-621 may freely engage the teeth of the toothed surface 521 as they normally would when the tool is operated in the forward direction under power.

The surgical tool can be operated in a reverse direction, either using the motor or manual power. The reverse direction can be selected by using the direction selection assembly, and particularly changing the position of the pins 603 and 605 in the channels within the housing. Upon changing the position of the pins 603 and 605, the pin 615 of the member 613 is engaged within the opening 618 of the anti-backdrive device 616, thereby locking the pawls 619-621 in a fixed or engaged position with the toothed surface 521 and not allowing them to "flip". Engagement of the pin 615 within the opening 618 removes the ratcheting action. Accordingly, in one embodiment, upon operation of the tool in reverse under power, the arms 632-634 transfer torque directly to the anti-backdrive device 616 via engagement of the pawls 619-621 with the pin 615. As such, in accordance with a particular embodiment, there is no ratcheting function in the reverse direction.

Figure 7:
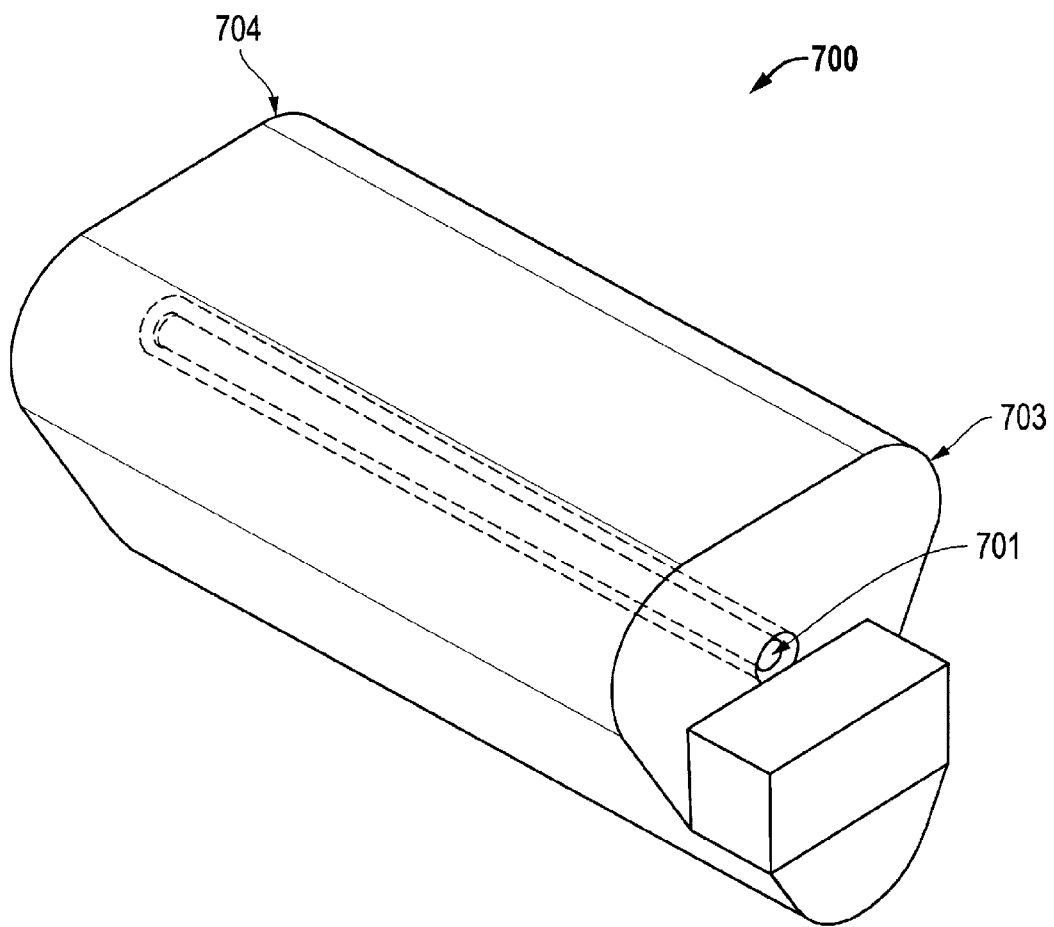
FIG. 7 includes a perspective view of a battery pack for use in a surgical tool in accordance with an embodiment.

FIG. 7 includes a perspective view of a battery pack 700 in accordance with an embodiment. In one embodiment, the battery pack 700 is configured to be disposed within the housing of the surgical tool proximate to the proximal end (see battery pack 323 of FIG. 3). In a more particular embodiment, the battery pack 700 includes a passage 701. As illustrated in FIG. 7, and discussed previously, the passage 701 can extend for substantially the entire length of the battery pack from a distal end 703 to a proximal end 704.

Figure 8A:
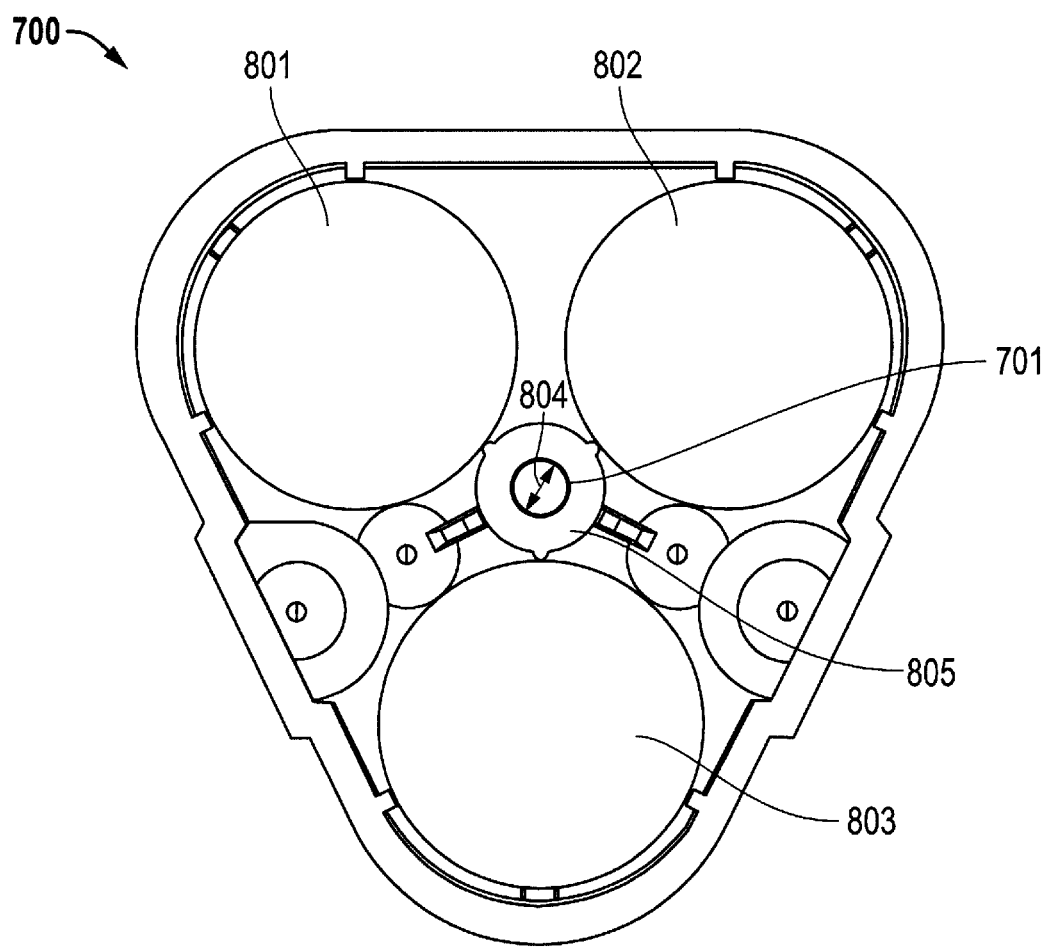
FIGS. 8A-8D include a cross-sectional illustrations of a battery pack for use in a surgical tool in accordance with an embodiment.
Figure 8B:
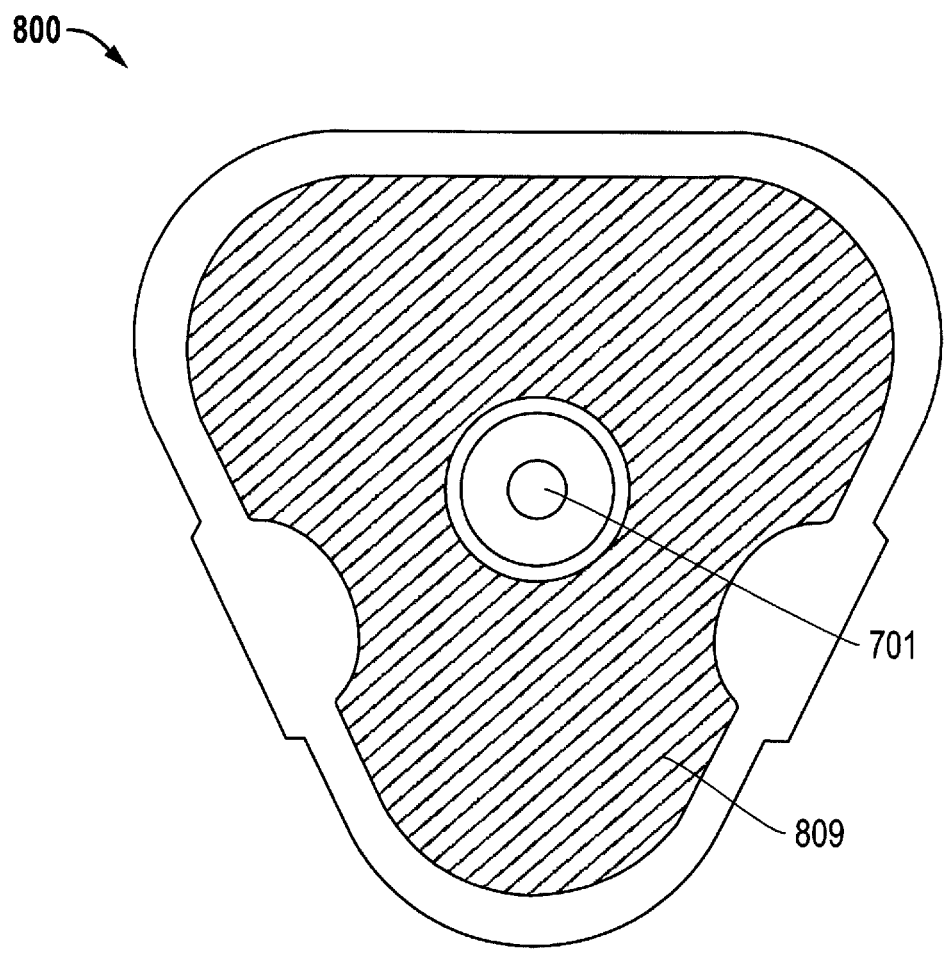

FIGS. 8A-8D illustrate different battery packs in accordance with a number of different embodiments. In particular, FIGS. 8A-8D illustrate different arrangements of power cells within the battery pack. Referring to FIG. 8A, a cross-sectional illustration of the battery pack is provided in accordance with an embodiment. In particular, the battery pack 700 illustrated includes multiple power cells 801, 802 and 803 (801-803). More particularly, the cross-sectional illustration of FIG. 8A further illustrates the passage 701 having a diameter 804 as previously described in accordance with FIG. 3. Moreover, in accordance with another embodiment, the passage 701 includes an electrically insulating lining 805 such that it substantially surrounds and defines the diameter 804 of the passage 701. The characteristics and materials useful for the insulating lining 805 are discussed in more detail in accordance with FIG. 3. In accordance with one embodiment, the battery pack 700 can have a generally triangular cross-sectional contour including three corners, wherein the power cells 801-803 are disposed within the corners of the battery pack 700. Moreover, in another particular embodiment, the battery pack 700 includes batteries 801-803 that are arranged around the passage 701, such that the passage 701 extends substantially between the power cells 801-803.

It will be appreciated that while the illustrated embodiment of FIG. 8A demonstrates multiple discrete power cells 801-803, according to another embodiment, the battery pack can include a single power cell having a passage extending therethrough. For example, referring to FIG. 8B, an alternative embodiment of the battery pack and power cells contained therein is illustrated. In particular, the illustrated embodiment of FIG. 8B includes a single power cell 809 substantially filling the interior of the battery pack 800. Moreover, in one embodiment, the battery pack 800 can include a passage 701 extending through the center of the battery pack 800 from a distal end to a proximal end. Still, according to another embodiment, the battery pack 800 may be absent a passage and may contain only openings at the distal end and the proximal end, and accordingly the power cell 809 includes a physical passage extending through its center and aligned with the openings within the battery pack at the distal end and the proximal end.

Figure 8C:
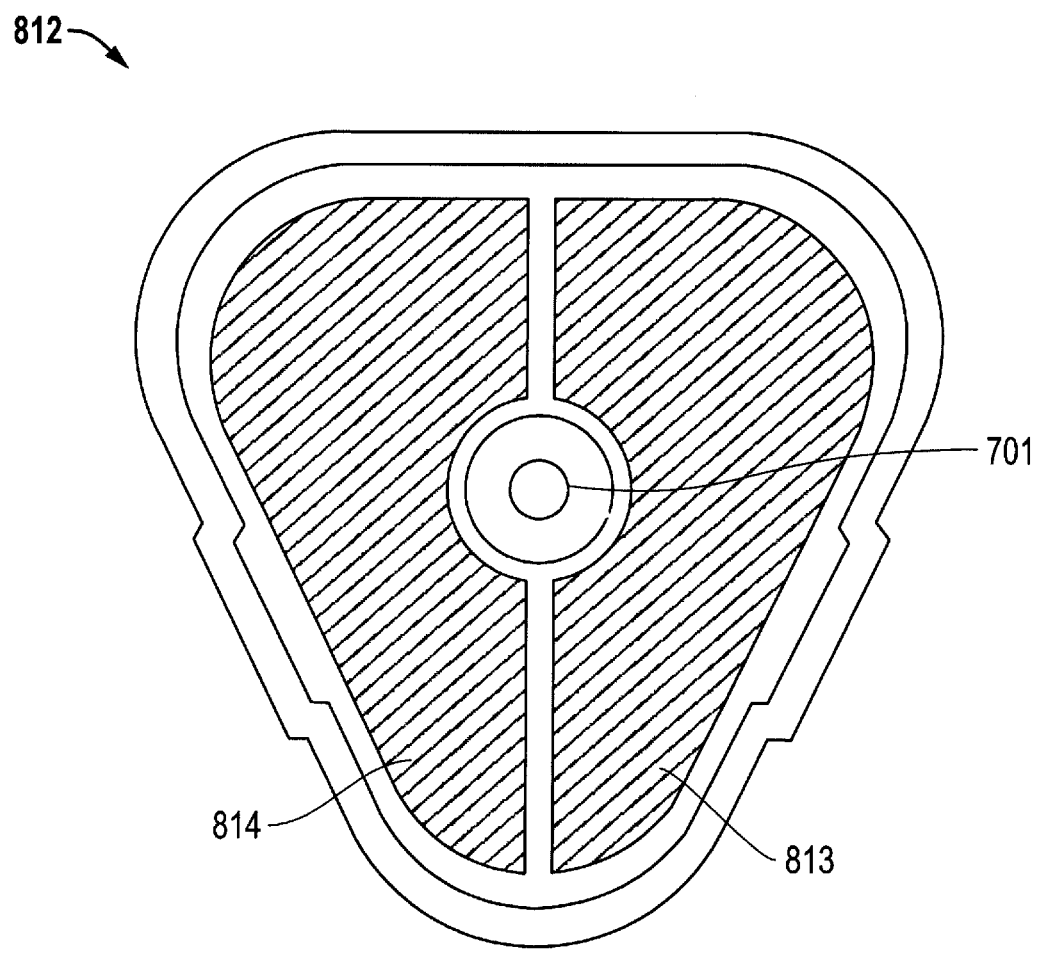

According to an alternative embodiment illustrated in FIG. 8C, a battery pack 812 can include two discrete power cells 813 and 814 disposed around a passage 701. As illustrated in FIG. 8C, in accordance with one embodiment, the power cells 813 and 814 can be bifurcated, having a shape substantially the same as a portion of the contour of the inner surface of the battery pack 812.

Figure 8D:
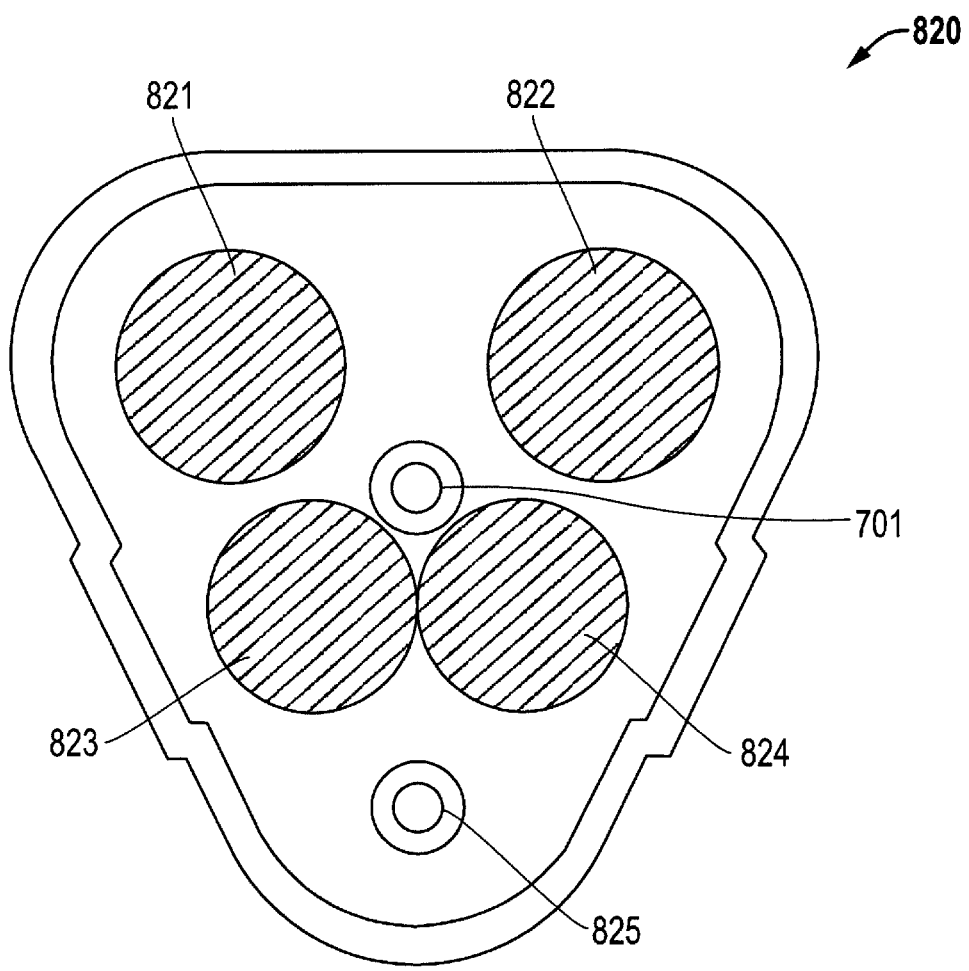

FIG. 8D illustrates a battery pack according to another embodiment. As illustrated, the battery pack 820 includes four discrete power cells 821, 822, 823, and 824 disposed within the interior of the battery pack 820. In a more particular embodiment, the battery pack 820 includes a passage 701 that is positioned at the center generally defined as the longitudinal axis of the battery pack 820. According to another embodiment, the battery pack 820 can further include a second passage 824 extending through the battery pack 824 and positioned a lateral distance away from the passage 701. In one particular embodiment, the passage 824 is positioned a distance away from the center of the battery pack 824 as generally defined by the longitudinal axis of the battery pack 820. The provision of a second passage 824 can facilitate cannulation of an additional device or object through the tool. Accordingly, the second passage 824 can extend individually through the length of the housing, or alternatively, may be combined with the passage 701 after exiting the battery pack.

As illustrated in FIGS. 8A-8D, the battery pack can include one or more power cells in various arrangements around or adjacent to one or more passages. Moreover, while the battery packs illustrated in FIGS. 8A-8D have been illustrated as having a generally triangular cross-sectional shape, other geometric shapes may be used. As such, in one particular embodiment, a square or rectangular cross-sectional shape is used to accommodate at least four discrete power cells in each of the four corners, while providing sufficient area for a passage through the center of the battery pack. In another embodiment, a circular battery pack can be used. In one embodiment, a power cell having a circular cross-sectional shape is particularly useful when using a single power cell designed to substantially fill the interior of the battery pack.

Figure 9:
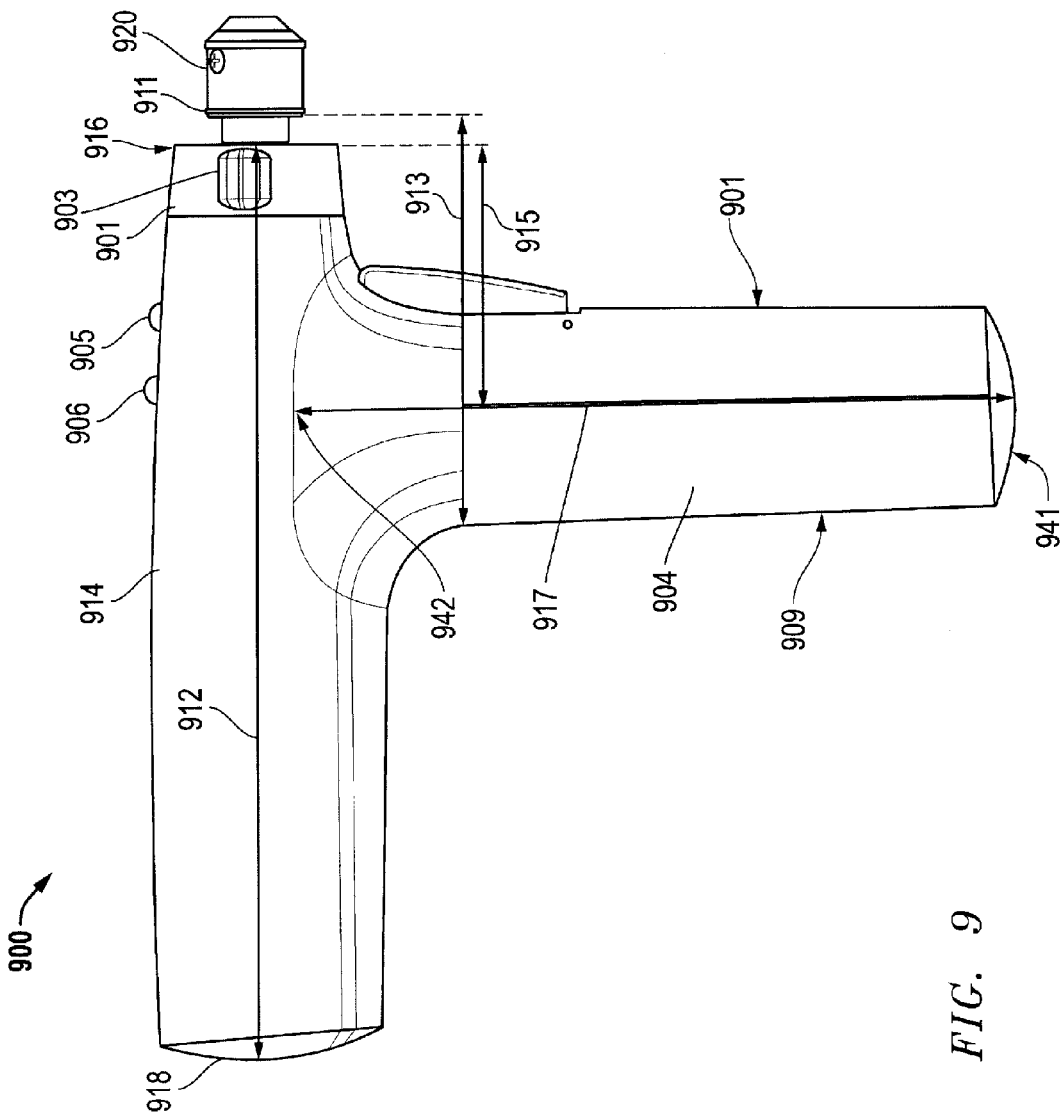
FIG. 9 includes a side view of a surgical tool in accordance with an embodiment.

FIG. 9 includes a side view of the surgical tool in accordance with an embodiment. According to one embodiment, the surgical tool 900 can include a switch 903 coupled to the housing 914 and electrically coupled to the motor. In accordance with a particular embodiment, the switch 903 is directly connected to a collar 901 which is rotatably connected to the housing 914 at the distal end 916. According to one particular embodiment, the switch 903 is moveable between a first position and a second position corresponding to a forward operating position and a reverse operating position of the motor. In another particular embodiment, the switch 903 is coupled to the collar 901, both of which are moveable such as around the circumference of the housing 914 to select between a forward operating condition and a reverse operating condition of the motor. In accordance with one particular embodiment, electrical coupling of the switch 903 with the motor can include ganging of a forward electrical switch and a reverse electrical switch, such that both must be operated to change the motor direction. Such a combination can facilitate certain safety control which may suitable for use in a surgical tool.

In accordance with another embodiment, the switch can be moved between a forward position and a reverse position, respectively operating the motor in a forward condition or a reverse condition. More particularly, in one embodiment, the ratchet mechanism (previously illustrated in FIG. 6B) can be coupled to the output shaft independent of the position of the switch 603. That is, ratcheting capabilities are available in the forward position or the reverse position. Still, in accordance with an alternative embodiment, the ratcheting mechanism may be disengaged from the output shaft when the shaft is in a reverse position.

In accordance with another embodiment, the switch 903 can further include a neutral position. Generally, the neutral position of the switch 903 may include decoupling of power to the motor, thereby making the tool suitable for a manual ratcheting procedure. In accordance with another embodiment, the switch 903 can include a neutral position wherein the output shaft is disengaged from the ratcheting position.

The surgical tool 900 can further include optical indictors 905 for indicating a state of the tool to the user. For example, in one particular embodiment, the optical indicators 905 and 906 can be electrically connected to the tools power source and electrically connected to the switch 903 and configured to indicate a forward or reverse state of the motor. In accordance with a particular embodiment, the optical indicator 905 can display an output when the switch 903 has selected the motor to rotate in a forward direction, and the optical indicator 906 can display an output when the switch 903 has selected the motor to rotate in a reverse direction. Suitable optical indicators can include lights such as LED's or the like. More particularly, the optical indicators 905 and 906 can have different optical qualities, such as color, making it suitable for the operator to verify the position of the switch 903 and the driving direction of the motor. As will be appreciated, in embodiments utilizing a switch 903 having a neutral position, an optical indicator may be coupled to that position of the switch 903 as well, or alternatively, neither of the optical indicators 905 and 906 may display an output when the motor is switched to the neutral position.

According to another embodiment, the surgical tool 900 can further include audible indicators configured to relay a state of the tool to the user. Like the optical indicators, according to one particular embodiment, audible indicators can be coupled to the switch to convey to the user the driving direction of the motor.

As illustrated in FIG. 9, the surgical tool 900 includes particular dimensions that have been configured to make the tool particularly useful for surgical applications. As such, in accordance with one embodiment, the surgical tool 900 can include a cradle distance 913 measured between a back surface of the handle 909 and a proximal end 911 of the chuck 920. Generally, the cradle distance 913 can be a fraction of the housing length 912 measured between the proximal end 918 of the housing 914 and a distal end 916 of the housing 914. As such, in accordance with a particular embodiment, the cradle distance 913 is not greater than about 50% of the housing length 912. In accordance with another embodiment, the cradle distance 913 is not greater than about 45% of the housing length or even not greater than about 42% of the housing length 912. In a more particular embodiment, the cradle distance 913 is a fraction of the housing length, such that it is at least about 30% and not greater than about 45% of the housing length 912, and more particularly within a range between about 38% and about 44%. In particular, a suitable cradle distance 913 facilitates one-handed operation of the surgical tool 900 and the capability to grasp the proximal end 911 of the chuck 920 while maintaining a grasp on the handle 904, thus releasing a bit shaft using a single hand. Such one-handed operation is particularly useful in surgical environments where contact with foreign objects (i.e., foreign to the patient's body) introduces a risk of infection. Accordingly, control of the tool with a single hand removes the need for contact of both of the surgeons' hands with a foreign object thus reducing risk of infection to the patient. Moreover, one handed operation of the surgical tool 900 facilitates efficient surgical procedures as well as the ability to quickly decouple a bit shaft from the chuck 920.

In accordance with another embodiment, the handle 904 is coupled with the housing 914 such that the handle 904 is closer to the distal end 916 than the proximal end 918 of the housing 914. In accordance with a particular embodiment, the handle 904 includes a central longitudinal axis 917 extending along the center of the handle 904 between the front surface 907 and the back surface 909. In accordance with one embodiment, the distance 915 between the central longitudinal axis and the distal end 916 of the housing 914 is particular suited for one-handed engagement of the switch 903. As such, the distance 915 is generally a fraction of the housing length 912. More particularly, in one embodiment, the distance 915 is not greater than 40% of the housing length 912. In accordance with anther embodiment, the distance 915 can be not greater than about 35% or even not greater than about 30% of the housing length 912. Still, in a more particular embodiment, the distance 915 is within a range between about 20% and 30% of the housing length 912, and more particularly within a range between about 22% and about 29% of the housing length. Such a distance 915 facilitates efficient use of the surgical tool, proper balance and improved feel of the tool, and reduced contamination to the patient, as again, it facilitates one-handed operation. Moreover, coupling of the handle 904 closer to the distal end 916 of the housing 914 improves tactile feedback, enabling finer control by the surgeon.

Moreover, the handle 904 has a length 920 measured between a distal end 941 and a proximal end 942 where the handle 904 connects to the housing 914 along the longitudinal axis that is a significant fraction of the housing length 912. In accordance with one embodiment, the handle 904 has a length 920 that is at least about 75% of the housing length 912. In accordance with another embodiment, the handle 904 has a length 920 that is at least about 75%, such as at least about 80% of the housing length 912. In a more particular embodiment, the handle 904 has a length 920 within a range between about 70% and about 90% of the housing length 912, and more particularly within a range between 74% and about 87% of the housing length 912. Such a design facilitates improved balance and tactile feed back of the surgical tool 900 as more weight is provided within the surgeon's hand, thereby facilitating greater control.

Generally, the surgical tool 900 has a housing length 912 of not greater than about 30 cm. In one particular embodiment, the housing length is not greater than about 25 cm, such as not greater than about 22 cm, or not greater than about 18 cm. According to another embodiment, the housing length 912 is at least about 5 cm, such as at least about 8 cm, and even at least about 10 cm. In accordance with a particular embodiment, the housing length 912 is within a range between 10 cm and about 25 cm.

Figure 10:
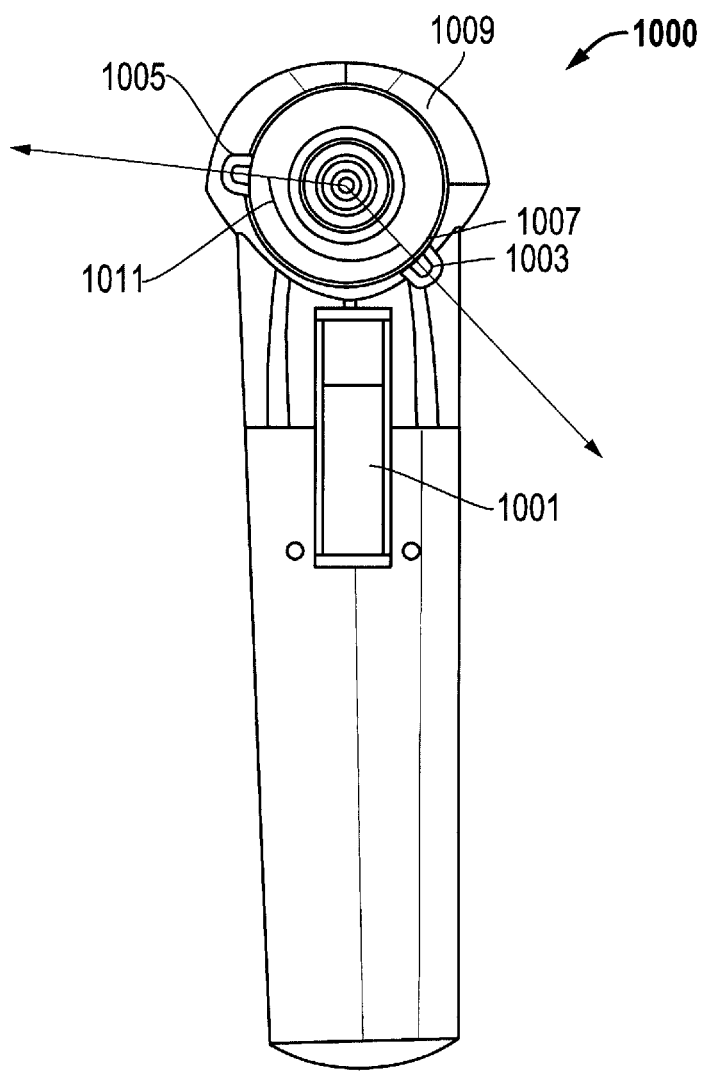
FIG. 10 includes a frontal view of a surgical tool in accordance with an embodiment.

Referring to FIG. 10, a front view of the surgical tool is illustrated in accordance with an embodiment. In particular, FIG. 10 is provided to illustrate the use of a first switch 1003 and a second switch 1005 coupled to a collar 1007 which in turn is coupled to the housing 1009. In accordance with one particular embodiment, the combination of a first switch 1003 and a second switch 1005 facilitates greater control and more accuracy in rotating the collar 1007 circumferentially around the housing 1009 to switch between a forward position, reverse position, and potentially a neutral position.

As further illustrated, the switches 1003 and 1005 can be positioned on the collar 1007 such that a particular angle 1011 is formed between them as measured from a longitudinal axis of the tool between vertices extending through the centers of the switches 1003 and 1005 as illustrated in FIG. 10. As such, in one embodiment, the angle 1011 is at least about 90°. In another embodiment, the angle 1011 is at least about 110°, such as at least about 120°. In one particular embodiment, the angle 1011 is within a range between about 120° and about 180°, and more particularly within a range between about 130° and about 160°. Such an arrangement of the switches 1003 and 1005 on the collar 1007 further facilitates efficient one-handed operation of the surgical tool 1000.

Figure 11:
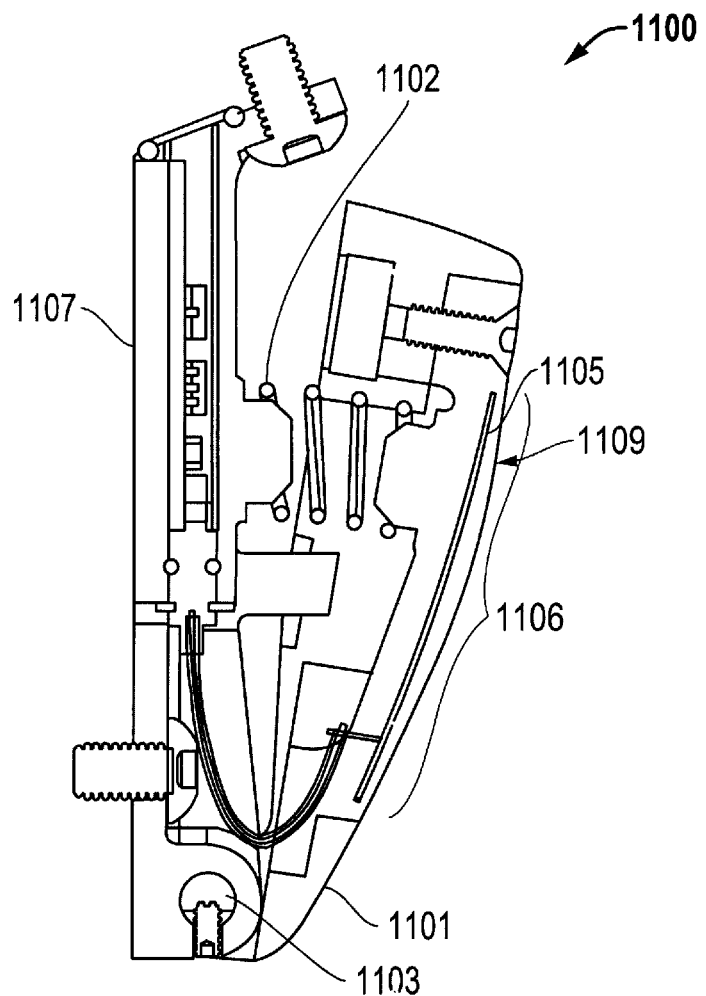
FIG. 11 includes a cross-sectional illustration of a trigger for use with a surgical tool in accordance with an embodiment.

Referring to FIG. 11, a cross-sectional illustration of a trigger in accordance with one embodiment is provided. As illustrated, a trigger 1100 is provided that includes a moveable trigger portion 1101 biased against a base portion 1107 by a biasing member 1102. As illustrated, the moveable trigger portion 1101 and base portion 1107 are pivotally connected at a pivot point 1103, such that the base portion 1107 can be fixably attached to the housing of the handle and the moveable trigger portion 1101 can pivot around the pivot point 1103 upon actuation by a user. In accordance with one embodiment, the trigger 1500 can include a magnetic trigger, including magnetic components, such as a reed switch.

Moreover, in accordance with one particular embodiment, the trigger 1100 includes a failsafe switch 1106 disposed on a surface of the moveable trigger portion 1101. In accordance with one particular embodiment, the failsafe switch 1106 includes a capacitive member 1105, sensing the presence of a user's finger on the surface 1107 of the failsafe switch 1106 such that absent minimal contact with the surface 1107, the trigger 1100 is decoupled from the motor. Utilization of a failsafe switch 1106 on the face of moveable trigger portion 1101 facilitates disengagement of the motor if the user's finger ceases contact with the surface 1107.

FIGS. 12-24 generally illustrate the incorporation of a navigation enabling member (NAV member) coupled to the tool as described herein. Generally, a navigation enabling member is attached to the tool and facilitates precise surgical procedures as the NAV member helps a surgeon identify the exact positioning of the tool with respect to the patient and therefore carry out more precise surgical procedures and placement of implants within the patient. Such NAV members that are attached to the tool may be part of a larger navigation system including a detector or monitor within the operating room that is used to identify the tool and triangulate the position of the tool in the operating room with respect to the detector. In particular, the NAV members disclosed herein may be particularly suitable for use with computer-assisted surgery (CAS) systems, for example, Medtronic Stealth Station™ systems.

Figure 12:
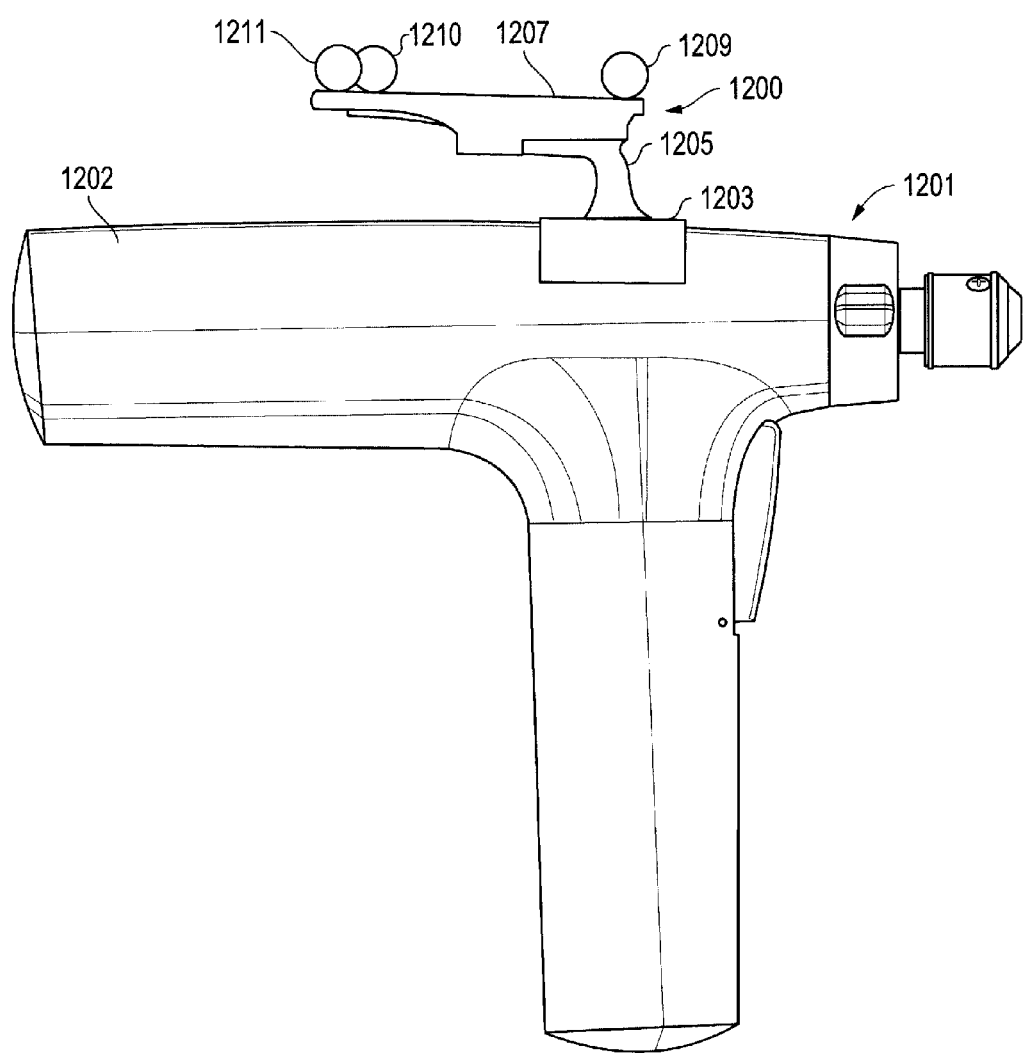
FIG. 12 includes a side view of a surgical tool and a navigation enabling member in accordance with one embodiment.

FIG. 12 includes a side view of a surgical tool, including a navigation enabling member in accordance with an embodiment. In particular, FIG. 12 illustrates a tool 1201 including the navigation enabling member 1200, otherwise a NAV member, connected to the housing 1202. The navigation enabling member 1200 can include a coupling 1203 directly connected to the housing 1202, a base 1205 connected to the coupling 1203, and an upper portion 1207 connected to the base 1205. In accordance with one embodiment, the upper portion 1207 may be selectively coupleable to the base 1205 such that the surgeon may remove the upper portion 1207 from the base 1205 for instances when a navigation enabling member is not desired for the particular procedure. In accordance within another embodiment, the base 1205 and the upper portion 1207 are selectively coupleable to the coupling 1203 such that the surgeon can remove the base 1205 and upper portion 1207 if desired. In still another embodiment, the coupling 1203, base 1205, and upper portion 1207 are selectively coupleable to the housing 1201 such that the surgeon can selectively couple the NAV member 1200 to the housing 1201 if desired. Further embodiments described herein will provide greater detail on the coupling mechanisms.

In accordance with another embodiment, the coupling 1203, base 1205, and upper portion 1207 can all be made of an autoclavable material including metals and polymers as described herein.

The navigation enabling member 1200 further includes passive components 1209, 1210 and 1211 (1209-1211) connected to the upper portion 1207. Generally, navigation enabling members can include passive components or active components, which are used to aid location of the tool within the operating room by a detector. In accordance with an embodiment, the passive components 1209-1211 can include reflecting structures capable of reflecting radiation emitted from a detector, enabling triangulation and location of the tool within the operating room. In accordance with an embodiment, the reflecting structures can include spheres, such as those illustrated in FIG. 12. In accordance with a more particular embodiment, generally the navigation enabling member 1200 includes at least three reflecting structures 1209-1211. Still, in other embodiments, the NAV member 1200 can include a greater number of reflecting structures.

In accordance with embodiments described herein regarding a navigation enabling member, it will be appreciated that description of passive components, such as reflecting structures 1209-1211 can be replaced by active components. Generally, active components differ from passive components in that they are radiation emitting components that emit radiation to be identified by a detector placed within the operating room, thereby facilitating triangulation and location of the tool. In accordance with one embodiment, suitable radiation emitting components can include optical components such as those emitting light within the visible spectrum. Still, other optical components may be used, such as those emitting in other portions of the electromagnetic spectrum, for example IR radiation. According to a particular embodiment, radiation emitting components can include light emitting diodes (LEDs). Notably, use of active components further includes electrical connection of active components to a power source. As such, in certain embodiments, active components used within a navigation enabling member can be electrically connected to the battery pack of the tool.

Figure 13:
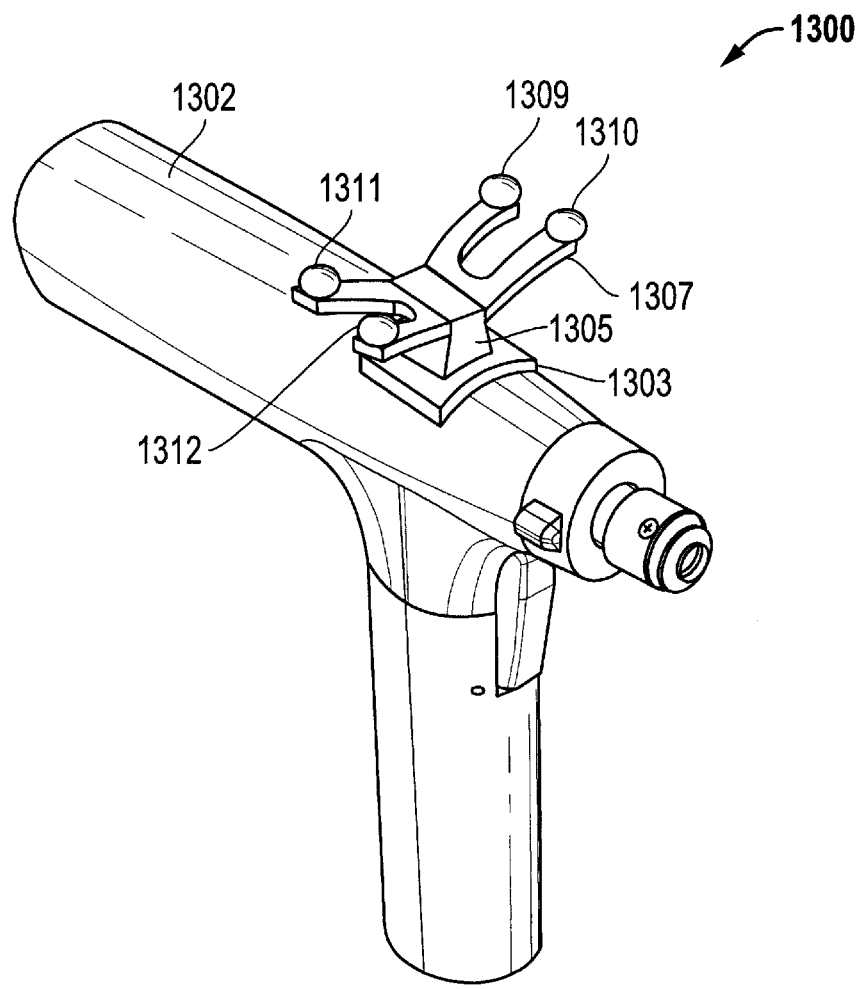
FIG. 13 includes a perspective view of a surgical tool and a navigation enabling member in accordance with one embodiment.

FIG. 13 includes a perspective view of the tool including a navigation enabling member in accordance with an embodiment. As illustrated, the navigation enabling member 1300 is connected to the housing 1302 via a coupling 1303. The navigation enabling member 1300 further includes a base 1305 connected to the coupling 1303, an upper portion 1307 connected to the base 1305, and reflecting structures 1309, 1310, 1312, and 1311 supported by the upper portion 1307. Notably, the navigation enabling member 1300 demonstrates that different orientations and numbers of reflecting structures 1309-1312 are possible.

Figure 14:
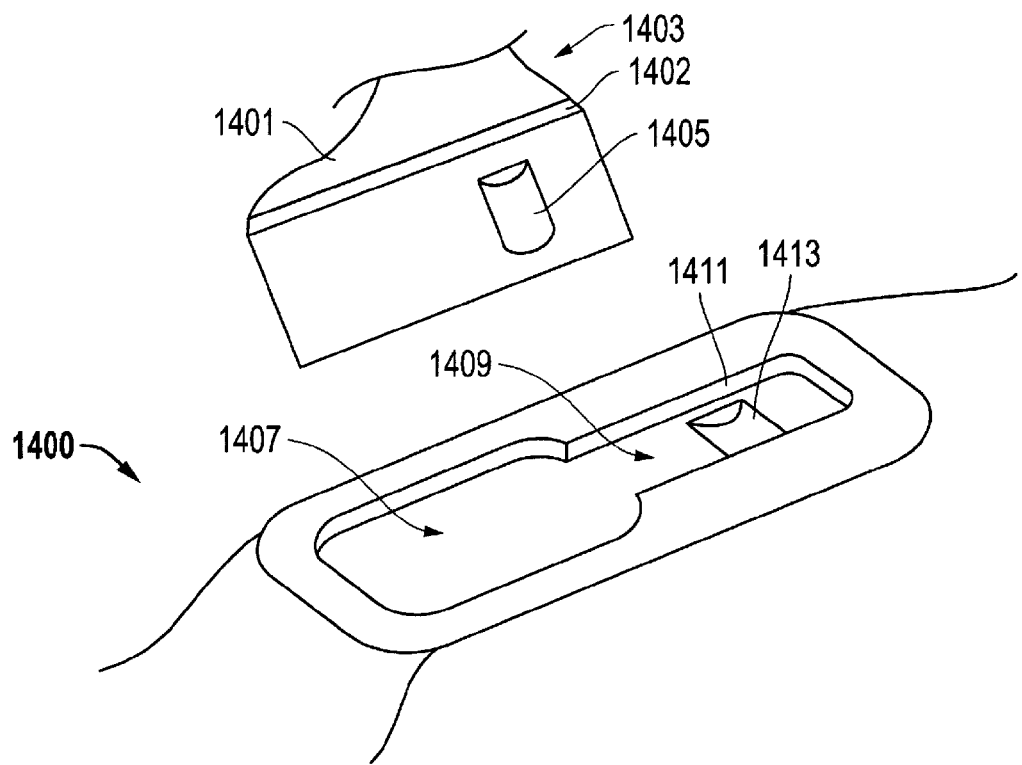
FIG. 14 includes a perspective view of a portion of a surgical tool having a coupling for connecting a navigation enabling member in accordance with one embodiment.

FIGS. 14-19 illustrated various coupling mechanisms used to attach a navigation enabling member to the housing of the tool. Generally, the navigation enabling member is rigidly attached to the housing to facilitate rigid positioning of the active components or passive components with respect to the tool and facilitating accurate triangulation of the tool by the detector. Accordingly, referring to FIG. 14, a perspective view of a coupling is provided for connecting a navigation enabling member to the housing of a surgical tool. In particular, FIG. 14 illustrates a tongue-in-groove connection including an opening 1407 within the housing 1400. The opening 1407 further includes a channel 1409 extending from the opening 1407 and defining a region having a narrow width as compared to the width of the opening 1407. Moreover, in one embodiment, the channel 1409 includes a lip 1411 extending over a portion of the channel 1409 and a depression 1413 within the bottom surface of the channel 1409.

The base 1401 of the navigation enabling member 1403 can include a coupling 1402 attached to a bottom surface of the base 1401 and configured to engage channel 1409 and fixably attach the navigation enabling member 1403 to the housing 1400. To couple the navigation enabling member 1403 to the housing 1400, the coupling 1402 may be initially engaged within the opening 1407 and slid forward into the channel 1409 such that the lip 1411 engages an upper surface of the coupling 1402 and a protrusion 1405 disposed on the bottom surface of the coupling 1402 is engaged within the depression 1413 of the channel 1409. Such a coupling mechanism facilitates a rigid connection between the housing 1400 and the navigation enabling member 1403.

Figure 15:
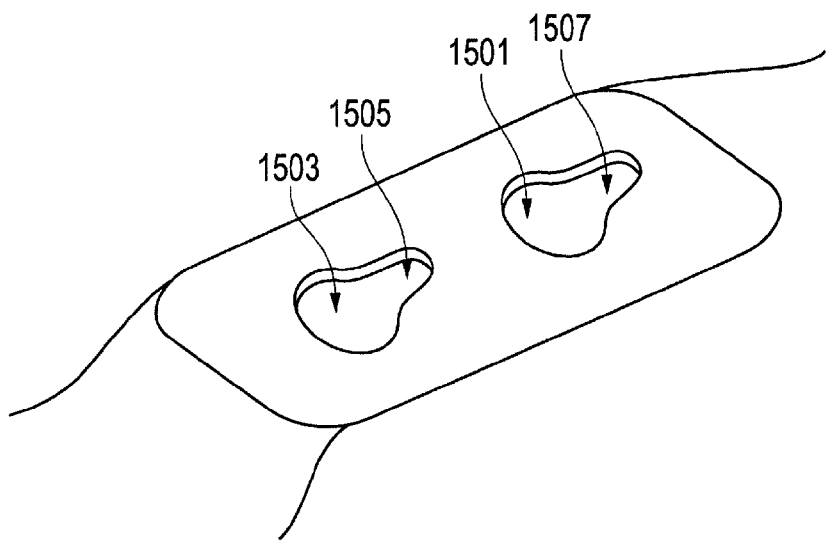
FIG. 15 includes a perspective view of a portion of a surgical tool having a coupling for connecting a navigation enabling member in accordance with one embodiment.

FIG. 15 illustrates another method of fixably attaching a navigation enabling member to the housing of the tool. In accordance with one embodiment, coupling of the navigation enabling member and the housing of the tool can be accomplished via sockets 1501 and 1503 as illustrated in FIG. 15. In particular, sockets 1501 and 1503 can include neck regions 1505 and 1507 wherein the width of the sockets 1501 and 1503 are reduced and facilitate engagement of protrusions having a complimentary structure on the bottom of a base portion of the navigation enabling member.

Figure 16:
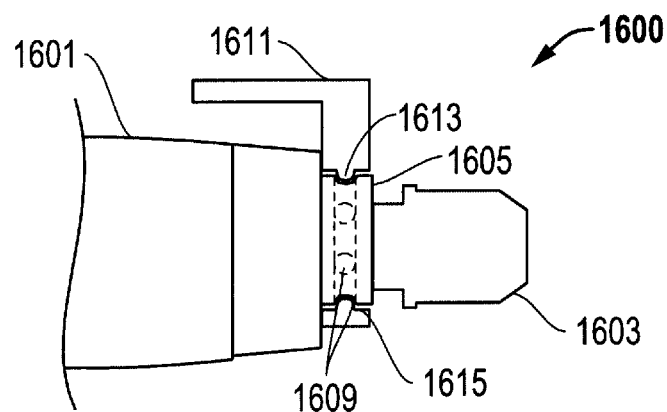
FIG. 16 includes a side view of a portion of a surgical tool having a coupling for connecting a navigation enabling member in accordance with one embodiment.
Figure 17:
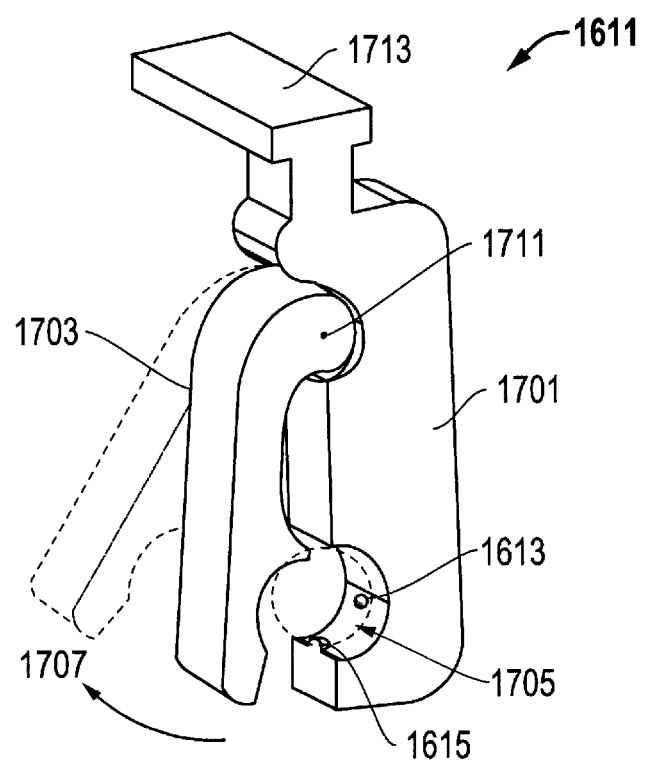
FIG. 17 includes a perspective view of a coupling of a navigation enabling member for connection to a surgical tool in accordance with one embodiment.

FIGS. 16 and 17 generally illustrate a coupling mechanisms for securing a navigation enabling member to a portion of the tool in accordance with an alternative embodiment. Referring to FIG. 16, a portion of the tool 1600 is illustrated including the housing 1601, a coupling 1605 extending from the housing 1601, and a quick connect assembly 1603 extending from the coupling 1605. In accordance with an embodiment, the coupling 1605 extends from the housing 1601 proximate to the output shaft of the tool, and the distal portion of the housing 1601. In accordance with a particular embodiment, the coupling 1605 is an extension of the housing 1601 and is a non-rotating portion of the tool. In another embodiment, the base 1611 can be used to support a navigation enabling member and can include protrusions 1613 and 1615. The protrusions 1613 and 1615 are configured to engage depressions 1609 within the coupling 1605 to rigidly fix the position of the base 1611 with respect to the coupling 1605 and housing 1601.

FIG. 17 includes a perspective view of the base 1611 for coupling a navigation enabling member to the tool as illustrated in FIG. 16. As illustrated, in accordance with one embodiment, the base 1611 includes a first arm 1701 connected to a second arm 1703 via a pivot point 1711. The arm 1703 can be pivoted between a variety of positions including an open position wherein the arm 1703 is extended away from arm 1701 as illustrated by the arrow 1707 and facilitating coupling of the base 1611 with the coupling 1605 illustrated in FIG. 16. Moreover, the base 1611 can include an opening 1705 configured to engage and fit around the coupling 1605. As previously illustrated, the base 1611 can include protrusion 1613 and 1615 within the opening 1705 configured to engage depressions 1609 of the coupling 1605 and fixably attach the base 1611 to the coupling 1605 and therefore the tool. The base 1611 can further include an upper portion 1713 extending from the base and configured to engage a portion of a navigation enabling member having passive components or active components.

In accordance with a particular embodiment, the base 1611 includes the arms 1701 and 1703 that are moveable such that the base 1611 can engage the coupling 1605 in a variety of positions. For example, in one position the base 1611 can be connected to the coupling 1605 such that the upper portion 1713 extends substantially above the top of the housing. In another embodiment, the base 1611 can be rotated with respect to the coupling 1605 and the tool, such that it engages the coupling in a different orientation and the upper portion 1713 extends to a side of the tool. Selective coupling and rotation of the base 1611 with respect to the coupling 1605 and the tool may be suitable for line of sight positioning of the navigation enabling member with a detector for accurate triangulation of the tool by the detector.

Figure 18:
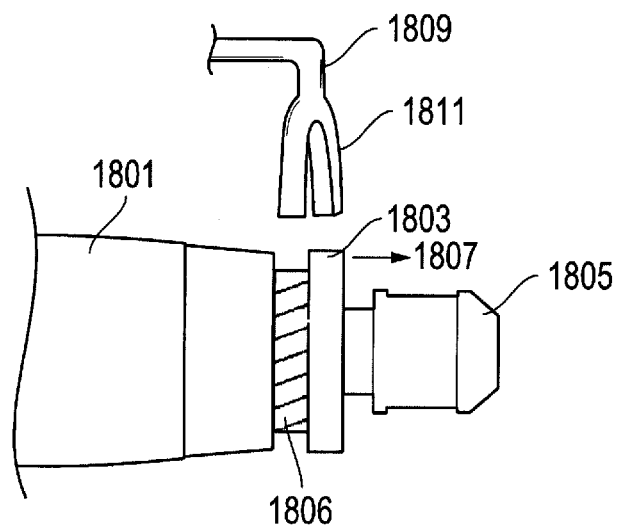
FIG. 18 includes a side view of a portion of a surgical tool including a port and a coupling for connecting a navigation enabling member in accordance with one embodiment.
Figure 19:
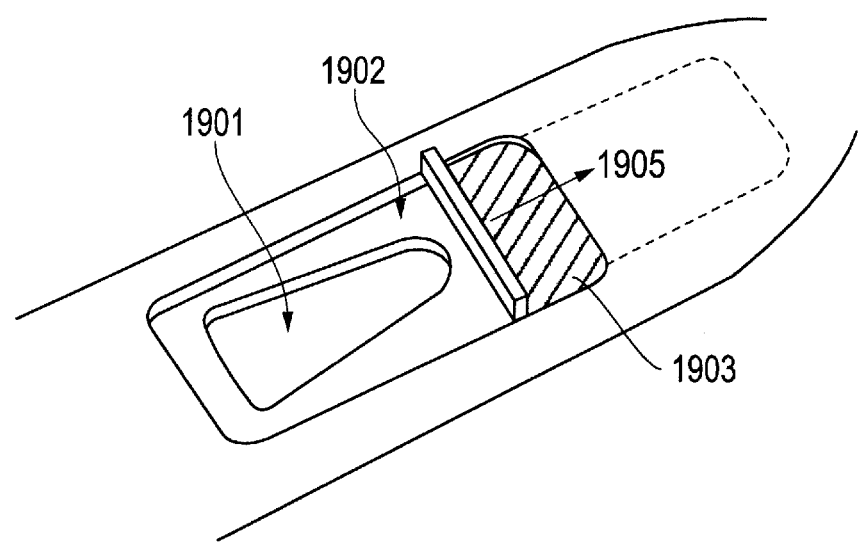
FIG. 19 includes a perspective view of a portion of a surgical tool including a port for connecting a navigation enabling member in accordance with one embodiment.

FIGS. 18 and 19 provide illustrations of ports for coupling of a navigation enabling member in accordance with one embodiment. FIGS. 18 and 19 demonstrate ports on the tool which may be selected between open positions and closed positions for selective engagement of a portion of a navigation enabling member. Referring to FIG. 18, a portion of the tool is illustrated including the housing 1801, a portion 1803 connected to the housing 1801, and a quick connect coupling 1805 connected to the portion 1803. In accordance with one embodiment, the portion 1803 is movable, such that it is part of a port selectable between an open position and a closed position. In accordance with a particular embodiment, the portion 1803 can be translated in a direction 1807 exposing a channel 1806 suitable for engaging a coupling 1811 of a base 1809 therein. In accordance with a particular embodiment, the coupling 1811 is positioned within the channel 1806 via a snap-fit connection fixably attaching the base 1809 to the housing 1801. In accordance with a more particular embodiment, the coupling 1811 can include protrusions configured to engage depressions within the channel 1806. In still another embodiment, the coupling 1811 may be positioned within the channel 1806 and the portion 1803 may be partially translated to another position, such as translated backwards toward an original closed position, until it is abutting the coupling 181, thereby facilitating a rigid attachment between the base 1809 and the housing 1801. The port facilitates selective engagement of a navigation enabling member when desired by a surgeon, and removal of the navigation enabling member when not desired.

FIG. 19 includes a perspective view of a port moveable between an open position and a closed position wherein in the open position the port is configured to engage a coupling of a navigation enabling member. As illustrated, FIG. 19 includes a port 1902 including a socket 1901 within the base of the port 1902 and a door 1903. In one embodiment, the door 1903 is slideable in a direction 1905 between an open position and a closed position, wherein in the open position the socket 1901 is exposed. As illustrated the socket 1901 within the port 1902 is suitable for coupling of a complimentary structure extending from a base of a navigation enabling member.

FIGS. 20-24 illustrate various embodiments of a navigation enabling member suitable for pivoting, rotation, translation or a combination of such movements. Movement of the navigation enabling member between positions may be suitable given the design and intended use of the tool. In particular, the shape of the tool may have the surgeon operating in close proximity to the patient, and impeding line-of-sight communication between the navigation enabling member and the detector. Accordingly, movement of the navigation enabling member around the tool may facilitate positioning of the NAV member such that it is detectable by the detector while the surgeon performs the task. It should be noted that movement of the navigation enabling member either pivoting, rotation, translation, or a combination thereof may be done so in a regimented fashion such that the position of the navigation enabling member with respect to a virtual center is maintained. Maintenance of the position of the NAV member with respect to a virtual center is suitable for accurate triangulation and positioning of the tool within the operating room thus allowing the surgeon to operate with the precision necessary during the procedure.

Figure 20:
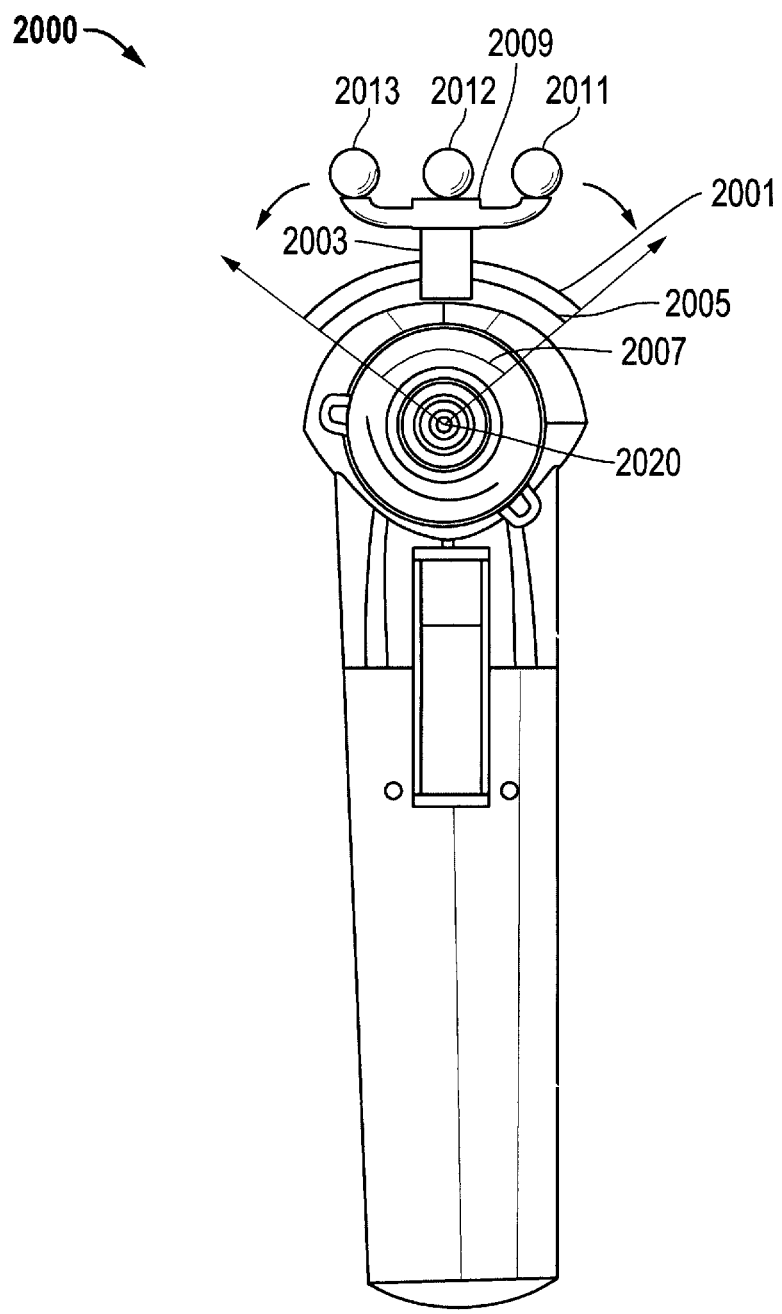
FIG. 20 includes a front view of a surgical tool including a navigation enabling member that is moveable in accordance with one embodiment.

FIG. 20 includes an illustration of the front portion of the tool and a navigation enabling member connected to the housing. As illustrated, the navigation enabling member 2000 includes a coupling 2001 connected to a base 2003, and an upper portion 2009 connected to the base 2003. The navigation enabling member 200 further includes passive components 2011, 2012, and 2013 connected to the upper portion 2009 and configured to reflect radiation and facilitate triangulation of the navigation enabling member 2000 and the tool. In accordance with a particular embodiment, the coupling 2001 includes a track 2005 configured to engage the base 2003. In accordance with a more particular embodiment, the base 2003 is configured to slideably engage along the track 2005 such that it is moveable between a variety of positions along the track through the central angle 2007.

Generally, the central angle 2007 spans an angle of not greater than about 180°. In a particular embodiment, the central angle 2007 is not greater than about 160°, such as not greater than about 130°, or even not greater than about 110°. In accordance with a particular embodiment, the central angle 2007 is not less than about 30°, and more particularly, within a range between about 45° and about 180°. In still another particular embodiment, translation of the navigation enabling member is restricted between 60° and 130° as defined by the central angle 2007.

Movement of the navigation enabling member 2000 along the track 2005 facilitates regimented motion of the navigation enabling member 2000 with respect to a virtual axis 2020 defined by the central axis of the output shaft. In accordance with a particular embodiment, rotation of the navigation enabling member 2000 along a track facilitates movement of the navigation enabling member 2000 along a series of pre-defined positions in which the distance between the navigation enabling member 2000 and the virtual axis 2020 is maintained such that accurate triangulation and precise positioning of the tool is maintained during surgery. As such, in one particular embodiment, the navigation enabling member 2000 can be moved along a path defined by the track 2005 wherein the path defined by the track 2005 not only rotates around the central angle 2005 but further translates laterally in a direction parallel to the virtual axis 2020. Translation of the NAV member 2000 in a direction parallel to the virtual axis 2020 may be suitable to maintain the distance between the virtual axis 2020 and the navigational enabling member 2000.

Figure 21:
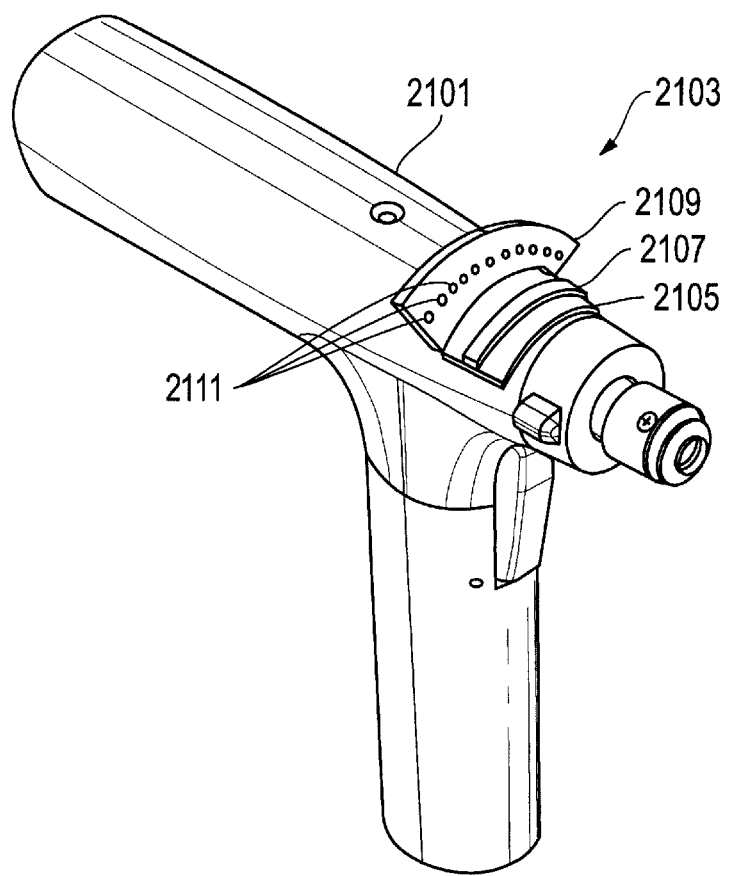
FIG. 21 includes a perspective view of a surgical tool including a base assembly of a navigation enabling member in accordance with one embodiment.

FIG. 21 illustrates a perspective view of a tool including a base assembly for a navigation enabling member in accordance with an embodiment. As illustrated in FIG. 21, the base assembly 2103 includes a coupling 2105, a track 2107 connected to the coupling 2105, and a positioning member 2109 connected to the coupling 2105. In accordance with one embodiment, the coupling 2105 is configured to connect the base assembly 2103 to the housing 2101 of the tool. In accordance with a particular embodiment, the base assembly 2103 is configured to provide motion to a moveable portion of a navigation enabling member. According to a more particular embodiment, the track 2107 of the base assembly 2103 provides a predetermined path along which a moveable portion of a navigation enabling member can traverse. Moreover, the positioning member 2109 includes a series of protrusions 2111 extending from a front face of the positioning member 2109 and configured to engage a portion of the moveable portion of the navigation enabling member. In accordance with a particular embodiment, the protrusions 2111 are spaced apart at discrete intervals across the front surface of the positioning member 2109 and facilitate positioning of a moveable portion of a navigational enabling member at any one of the locations defined by the protrusions 2111.

Figure 22:
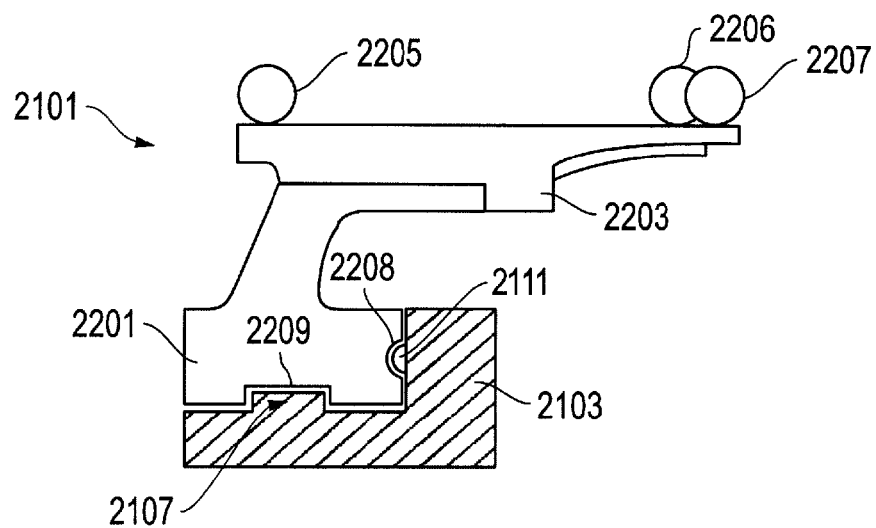
FIG. 22 includes a cross-sectional view of a portion of a base assembly, moveable portion, and upper portion of a navigation enabling member in accordance with one embodiment.

FIG. 22 includes a side view of navigation enabling member including the base assembly illustrated in FIG. 21 in accordance with one embodiment. As illustrated, the navigation enabling member 2101 includes a base assembly 2103 including a track 2107 extending from a bottom surface of the base assembly 2103 and a protrusion 2111 extending from a forward surface of the base assembly 2103 as previously illustrated in FIG. 21. In accordance with one embodiment, the navigation enabling member 2101 further includes a moveable portion 2201 connected to an upper portion 2203 and reflecting components 2205, 2206, and 2207 connected to an upper surface of the upper portion 2203. In accordance with one embodiment, the moveable portion 2201 includes a depression 2209 configured to engage the track 2107 of the base assembly 2103 and facilitate slideable engagement of the moveable portion 2201 with the base assembly 2103.

In another embodiment, the moveable portion 2201 further includes a depression 2208 along a rear surface configured to engage the protrusion 2111 and fixing the relative position of the moveable 2201 relative to the base assembly 2103. According to one embodiment, the protrusion 2111 can be a moveable plunger, such as a ball plunger, configured to be recessed within the rear portion of the base assembly until aligned with a depression 2208 within the moveable portion 2201 and then extending into the depression 2208 and fixing the relative position of the moveable portion 2201 with respect to the base assembly 2103. The moveable portion 2201 and base assembly 2103 are configured to interact such that the moveable portion 2201 is moveable along the track 2107 and positionable with respect to the base assembly 2103 at any one of a series of discrete positions defined by a protrusion 2111.

Figure 23:
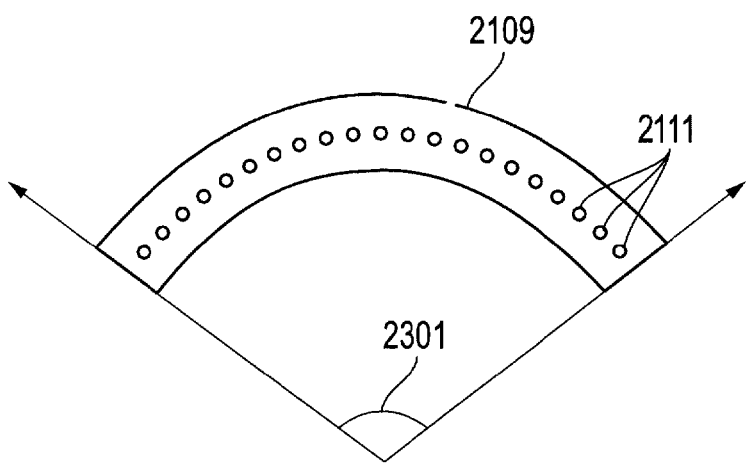
FIG. 23 includes a front view of a portion of a base assembly of a navigation enabling member in accordance with one embodiment.

Referring to FIG. 23, a portion of the base assembly is illustrated in accordance with one embodiment. The positioning member 2109 of the base assembly is illustrated including a series of protrusions 2111 equally spaced apart and defining discrete positions along the surface of the positioning portion 2109. In accordance with one embodiment, the positioning portion 2019 spans a central angle 2301 of not greater than about 180°. In accordance with another embodiment, the central angle 2301 spanned by the positioning portion 2109 is not greater than about 160°, such as not greater than about 130°, or even not greater than about 110°. Still, in accordance with a particular embodiment, the central angle 2301 spanned by the positioning portion 2109 is within a range between about 45° and about 160°, and more particularly, within a range between about 60° and about 120°. It will be appreciated that while the positioning member 2109 is illustrated as having a series of protrusions 2111, a series of depressions may be used, such that the depressions are configured to engage a protrusion on a complementary member.

In further reference to FIG. 23, the series of protrusions 2111, or in certain embodiments, the series of plungers, extend along the surface of the positioning portion 2109 and define discrete positions for fixing the moveable portion 2201 relative to a base assembly 2103 as illustrated in FIG. 22. In accordance with a particular embodiment, the protrusions define a plurality of positions that are discrete positions and are equally spaced apart by at least 5°. In another embodiment, the protrusions 2111 define discrete positions that are spaced apart by at least about 10°, such as at least about 15°, or even at least about 20°. Still, for other embodiments, the protrusions 2111 define discrete positions that are spaced apart by not greater than about 60°, such as not greater than about 45°, or even not greater than about 30°. According to one particular embodiment, the protrusions 211 define discrete positions that are spaced apart from each other within a range between about 5° and about 45°, and more particularly within a range between about 10° and about 20°.

Figure 24:
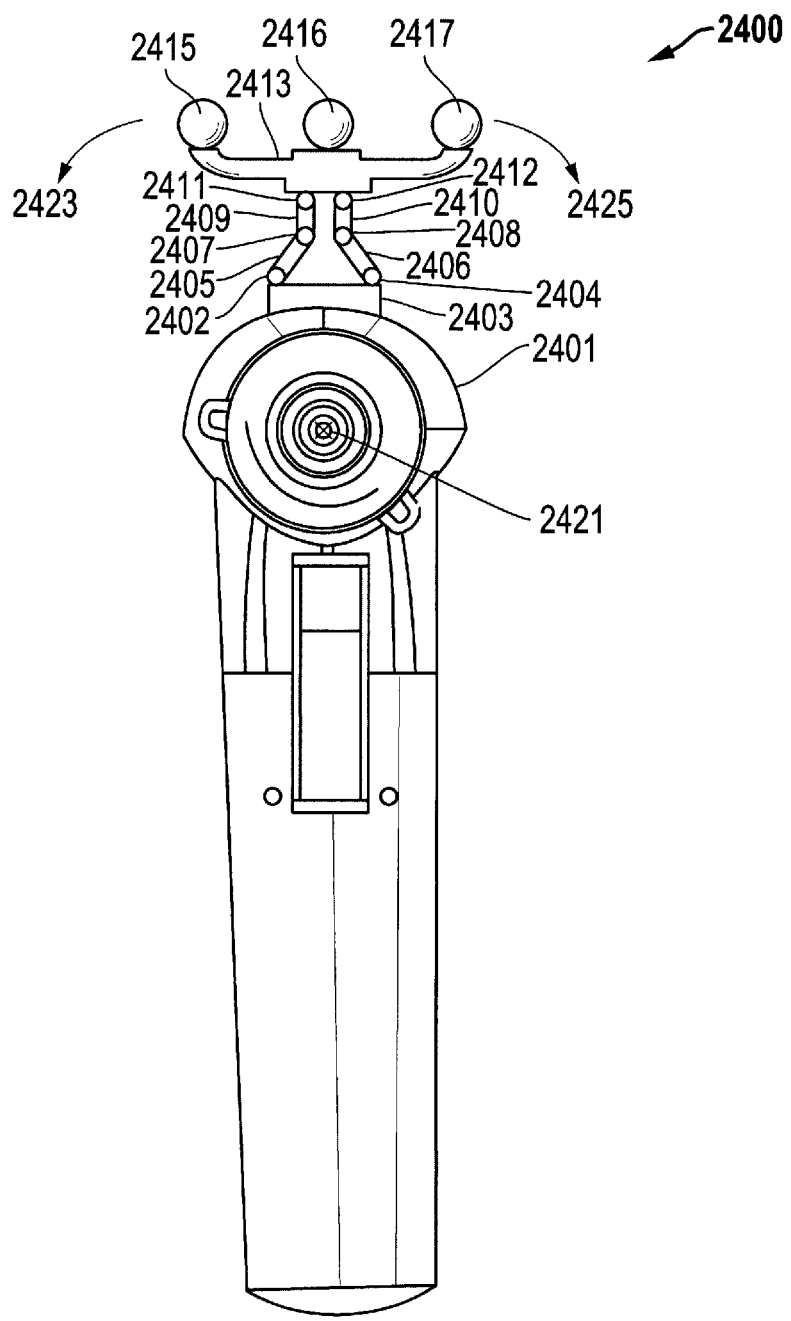
FIG. 24 includes a front view of a surgical tool including a moveable navigation enabling member in accordance with one embodiment.

FIG. 24 includes an illustration of a surgical tool including a navigation enabling member in accordance with an embodiment. As illustrated, the tool includes a housing 2401 and a coupling 2403 connected to the housing 2401 to support a navigation enabling member 2404. The navigation enabling member 2404 further includes articulating joints 2402 and 2404 connected to the coupling member 2403, arms 2405 and 2406 connected to the articulating joints 2402 and 2404, and articulating joints 2407 and 2408 connected to the arms 2405 and 2406. The navigation enabling member 2400 further includes another set of arms 2409 and 2410 connected to the articulating joints 2407 and 2408, and can further include another set of articulating joints 2411 and 2412 connected to the arms 2409 and 2410. In accordance with one embodiment, the navigation enabling member 2404 further includes an upper portion 2413 supporting reflecting components 2414, 2416, and 2417.

In accordance with a particular embodiment, the navigation enabling member 2404 is configured to be freely moveable with respect to the housing 2401 of the tool such that it is rotatable, pivotable, translatable, or a combination thereof. Generally, the navigation enabling member 2404 is rotatable around a virtual axis 2421 defined by the longitudinal axis of the output shaft of the tool. Accordingly, the navigation enabling member 2404 is rotatable with respect to this axis and the directions 2423 and 2425 as illustrated. Moreover, the navigation enabling member 2404 maybe translatable in a direction parallel to the virtual axis 2421 defined by the longitudinal axis of the output shaft of the tool.

In accordance with one particular embodiment, the navigation enabling member 2404 is moveable between a discrete set of predetermined positions, wherein such positions are defined by limited movement of the arms 2405, 2406, 2409 and 2410 with respect to the articulating joints 2402, 2404, 2407, 2408, 2411 and 2412. The ability to move the navigation enabling member 2404 between a discrete set of predetermined positions can facilitate maintaining a predefined distance between the navigation enabling member 2404 and the virtual axis 2421 for accurate triangulation of the navigation enabling member 2404 by the detector in the operating room.

FIGS. 25-32 provide illustrations of the tool as described herein combined with a neural integrity monitoring (NIM) system. Generally, NIM systems are useful for monitoring the neurological system of a patient during particular surgical procedures. For example, during spinal surgeries where the spinal cord, a critical component of the neurological system, is within close proximity of the surgical site, use of a NIM systems allow a surgeon to monitor changes and avoid damage to the neurological systems that may occur due to certain surgical procedures. For example, in one particular instance, a surgeon may wish to place anchors within the pedicles of the spinal column for a certain implant. The placement of these anchors must be precise, such that they do not interfere with the spinal cord and, accordingly, integration of a NIM system within the operating room allows a surgeon to monitor the neurological status of the patient while placing the anchors in the patient, providing the surgeon with greater assurance that the placed anchors do not adversely affect the neurological system of the patient.

Neural integrity monitoring (NIM) systems can have a variety of components, but generally include a series of electrodes placed on the patient during surgery, a tool capable of carrying an electrical signal, and a monitor capable of receiving the electrical signals from the tool and monitoring the neurological status of the patient. As will be illustrated in FIGS. 25-32, given the design of the surgical tool and its intended use, particular designs of NIM system integrations are particularly designed to integrate with the surgical tool.

Figure 25:
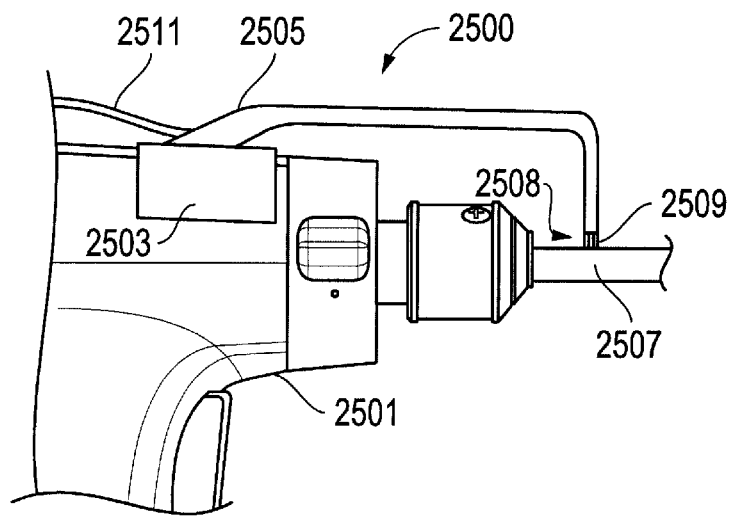
FIG. 25 includes a side view of a portion of a surgical tool including a neural integrity monitoring (NIM) member in accordance with one embodiment.

FIG. 25 includes a side view of a portion of the tool and a NIM member connected to the tool. As illustrated in FIG. 25, the NIM member 2500 includes a base assembly 2503 connected to the housing 2501 of the tool. In accordance with one embodiment, the NIM member 2500 further includes an arm 2505 extending from the base assembly 2503 and extending over the housing 2501 of the tool.

In a more particular embodiment, the arm 2505 includes an active assembly 2508 at the distal end of the arm 2505 configured to make electrical contact with an electrically conductive portion of a bit 2507. Generally, when using a NIM system, portions of the tools, such as the bit 2507 and NIM member 2500 have electrically conductive portions facilitating the transmission of electrical signals between the patient and a monitoring system. Accordingly, reference to an active assembly as used herein includes a portion of the NIM member that is capable of carrying an electrical signal and relaying information between the patient and a monitoring system. As such, the bit 2507 illustrated in FIG. 25 can have a conductive portion facilitating transmission of a signal from the patient to the active assembly 2508 of the NIM member 2500. In accordance with a particular embodiment, the active assembly 2508 includes a brush 2509 having at least one electrically conductive bristle, or possibly a plurality of electrically conductive bristles, electrically connected to the conductive portion of the bit 2507. The electrical contact of the brush 2509 with the conductive portion of the bit 2507 facilitates transmission of the signals from the patient to the active assembly 2508 of the NIM member 2500 and subsequently to a monitoring system.

In accordance with one embodiment, the active assembly 2508 can include power driven components that can be connected to a power supply. In a more particular embodiment, the active assembly 2508 can include components that are electrically connected and powered by the battery pack contained within the tool.

FIG. 25 further illustrates a wire 2511 extending from the arm 2505. In accordance with a particular embodiment, the arm 2505 has an electrically conductive portion that can electrically connect the wire 2511 with the active assembly 2508 for transmission of an electrical signal there through. The wire 2511 can connect the NIM member 2500 with a remote monitoring system within the operating room. As will be described in more detail with particular embodiments, the NIM member 2500 can alternatively have wireless capabilities such that it can transmit a signal to a remote monitoring system without a wire connection. Moreover, it will be appreciated that for all NIM member embodiments described herein, a wire connection or wireless connection can be utilized for transmitting a signal between the active assembly and a remote monitoring system.

Figure 26:
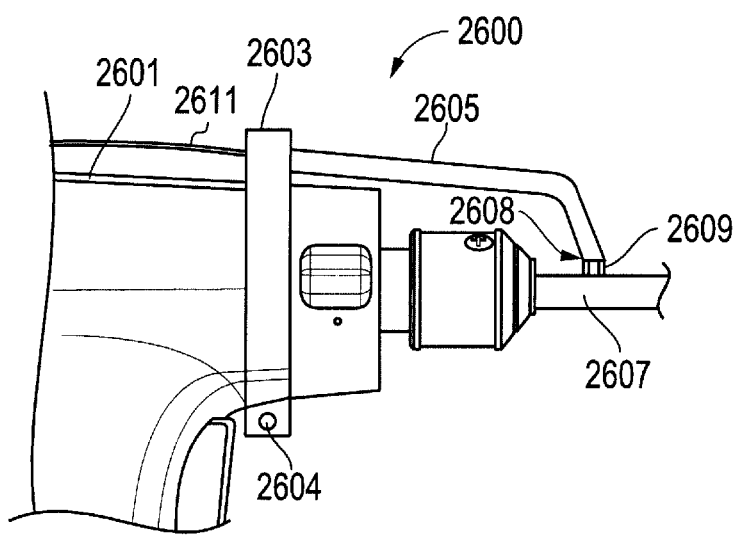
FIG. 26 includes a side view of a portion of a surgical tool including a neural integrity monitoring (NIM) member in accordance with one embodiment.

Referring to FIG. 26, a side view of a portion of the tool including an NIM member is illustrated in accordance with one embodiment. As illustrated, the NIM member 2600 includes a base assembly 2603 extending around a periphery of a portion of the housing 2601. In accordance with a particular embodiment, the base assembly 2603 is a collar extending around a circumference of the housing 2601 and selectively coupled via a pin 2604 extending through a portion of the base assembly 2603 and fastening it to the housing 2601. The NIM member 2600 further includes an arm 2605 extending from the base assembly 2603, and an active assembly 2608 including a brush 2609 configured to electrically connect the active assembly 2608 with a conductive portion of a bit 2607. In accordance with one embodiment, the NIM member 2600 further includes a wire 2611 extending from the base assembly 2603 and electrically connecting the active assembly 2608 with a remote monitoring system.

Generally, the NIM members illustrated herein are fixably and rigidly connected to the housing of the tool, such that the active assembly maintains an electrical contact with a conductive portion of a bit. Accordingly, coupling mechanisms such as those shown in FIGS. 14-19 including channels, sockets, and ports having selectively open and closed positions can be used to selectively couple a NIM member to a portion of the housing.

Figure 27:
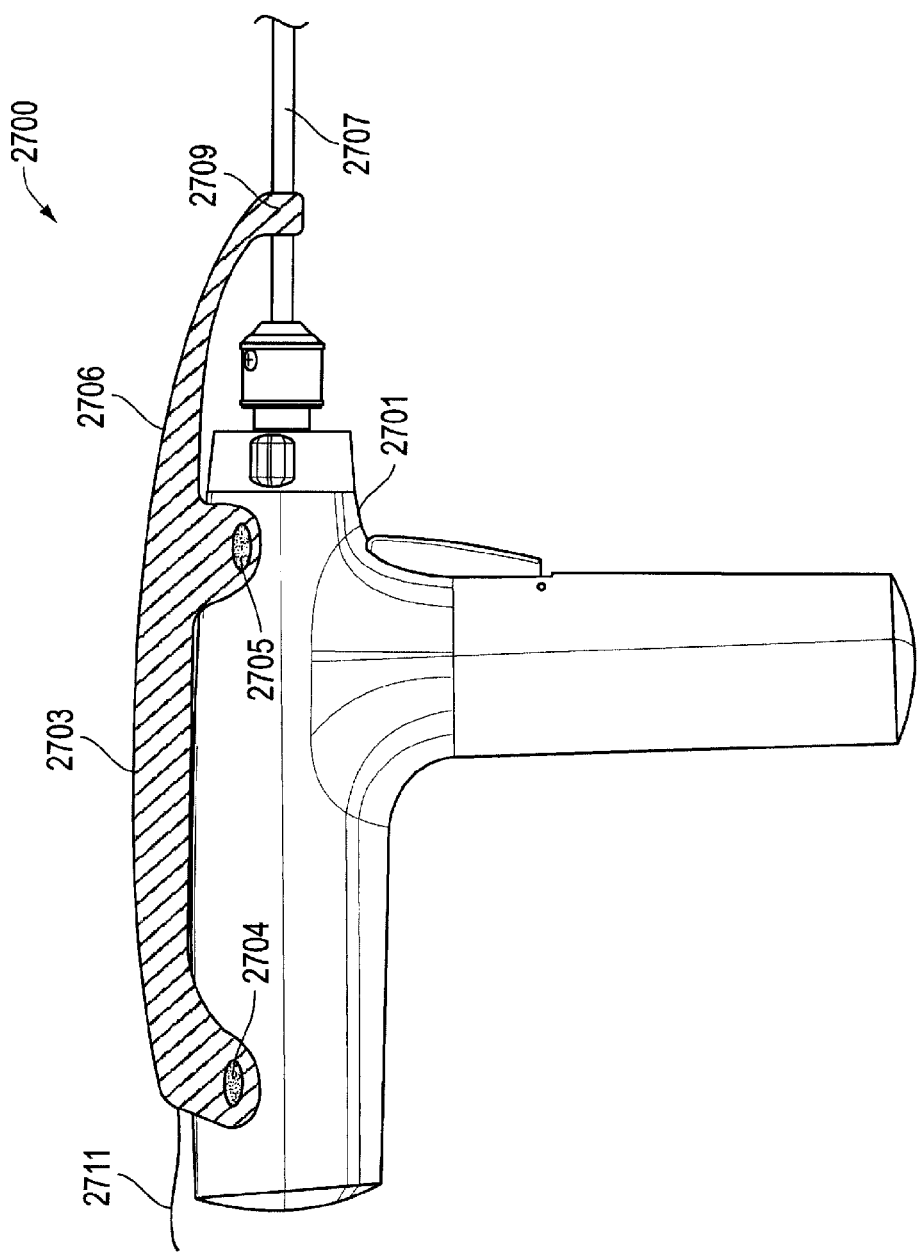
FIG. 27 includes a side view of a surgical tool including a neural integrity monitoring (NIM) member in accordance with one embodiment.

FIG. 27 includes a side view of a surgical tool and a NIM member connected in accordance with one embodiment. As illustrated, the NIM member 2700 includes a base assembly 2703 coupled to the housing 2701 of the tool via couplings 2704 and 2705. In accordance with a particular embodiment, the base assembly 2703 extends along the majority of the length of the housing 2701 and has a particularly low profile designed to reduce interference with line-of-sight operations of the surgeon. In one embodiment, the couplings 2704 and 2705 can connect to the housing via a snap-fit connection. In another embodiment, the couplings 2704 and 2705 are connected to the housing 2701 via magnets. Use of such couplings 2704 and 2705 facilitate selective coupling and decoupling of the NIM member 2700 with the tool.

As illustrated, the NIM member 2700 further includes an arm 2706 extending from the base assembly 2703 over the housing 2701 and the quick-connect coupling. In accordance with an embodiment, the NIM member 2700 further includes an active assembly coupled to the distal end of the arm and configured to electrically connect the active assembly 2709 with a conductive portion of a bit 2707. In accordance with a particular embodiment, the active assembly 2709 can be connected to the bit 2707 such that it substantially surrounds the circumference of the bit 2707. In accordance with a more particular embodiment, the active assembly 2709 can further include a brush assembly such as that shown in FIG. 25 or FIG. 26, to make electrical contact with the conductive portion of the bit 2707. In accordance with an alternative embodiment, the active assembly 2709 can further include a slip-ring contact with the bit 2707 configured to make electrical contact with the conductive portion of the bit 2707. As further illustrated, the NIM member 2700 further includes a wire 2711 extending from the base assembly 2703 and configured to provide an electrical connection and transmission of a signal to a remote monitoring system.

Figure 28:
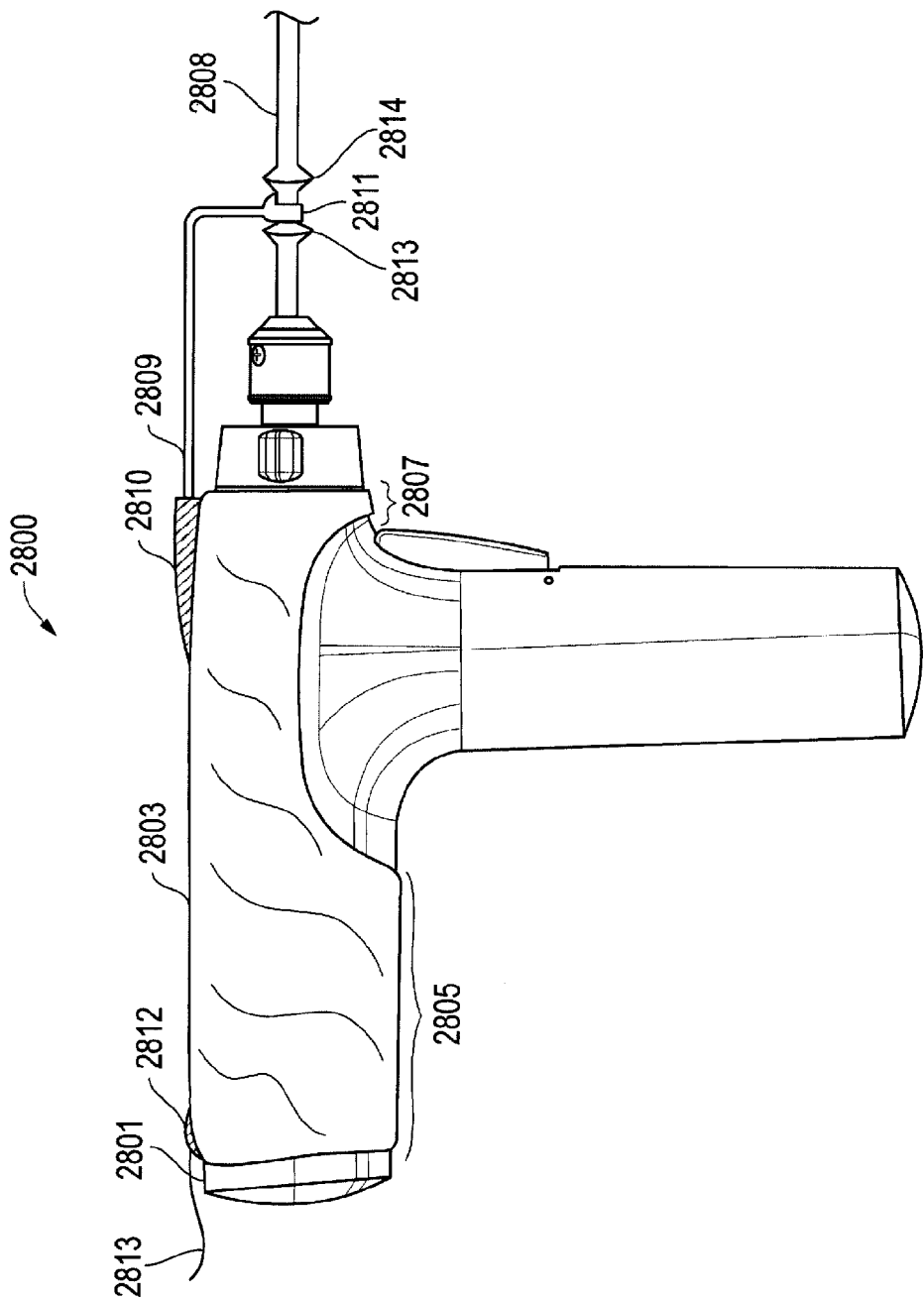
FIG. 28 includes a side view of a surgical tool including a neural integrity monitoring (NIM) member in accordance with one embodiment.

FIG. 28 includes a side view of a surgical tool including an NIM member in accordance with an embodiment. As illustrated, the NIM member 2800 includes a base assembly 2803 directly connected to the housing 2801. In accordance with an embodiment, the base assembly 2803 can include a pliable material, suitable for wrapping around the contours of the housing 2801. In a more particular embodiment, the base assembly 2803 can include a polymer material. Use of a pliable, polymer material for the base assembly 2803 facilitates reduction of particulate material entering the interior of the tool, and may further be disposable after conducting the surgery. In accordance with one embodiment, the base assembly 2803 includes a pliable material capable of wrapping around itself within regions 2805 and 2807. In accordance with another embodiment, the base assembly 2803 includes a pliable material that can be connected to itself via a physical attachment or an adhesive for selective coupling and decoupling by the surgeon.

In accordance with another embodiment, the base assembly 2803 can further include a base member 2810 connected to the base assembly 2803 proximate to the distal end of the housing. The base member 2810 may be a more rigid component as compared to the base assembly 2803 thereby facilitating rigid fixation and coupling of the arm 2809 extending from the base member 2810. The base assembly 2803 can further include a coupling 2812 connected to the base assembly 2803 at the proximal end of the housing and configured to connect a wire 2813 with the base assembly 2803.

The NIM member 2800 further includes an active assembly 2811 connected to a distal end of the arm 2809 and configured to electrically connect the active assembly 2811 with a conductive portion of the bit 2808. In accordance with one embodiment, the active assembly 2811 has a u-shaped or horseshoe-shaped configuration to facilitate electrical connection between the active assembly and the conductive portion of the bit 2808 while maintaining free rotation of the bit 2808. In another embodiment, the bit 2808 can include flanges 2813 and 2814 configured to maintain a proper contact of the active assembly 2811 with a conductive portion of the bit 2808. Flanges 2813 and 2814 may further indicate the intended region along the bit 2808 for coupling the active assembly 2811.

Figure 29:
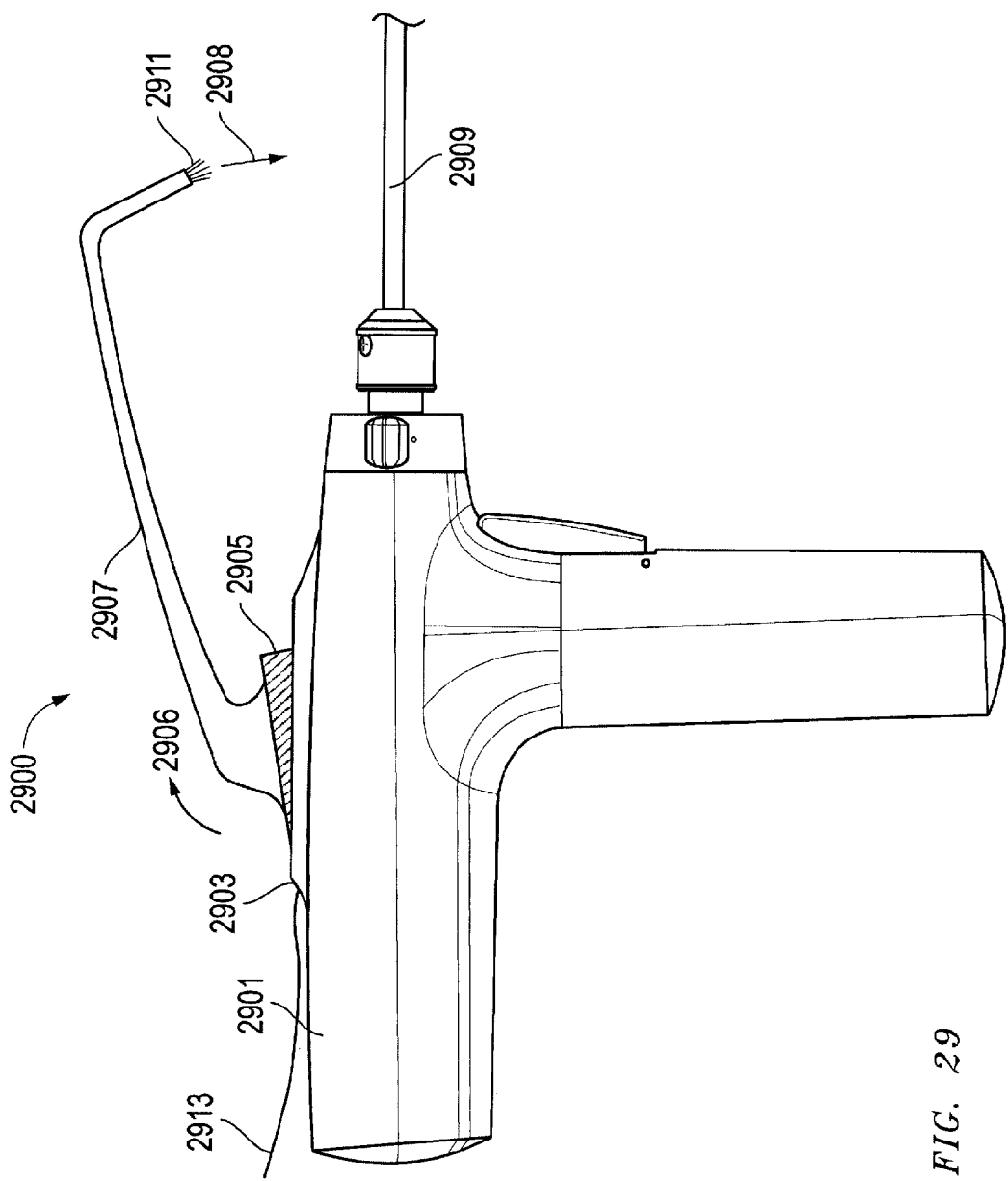
FIG. 29 includes a side view of a surgical tool including a neural integrity monitoring (NIM) member in accordance with one embodiment.

FIG. 29 includes a side view of the tool including a NIM member 2900 connected to the tool. As illustrated, the NIM member 2900 includes a base assembly 2903 that can include a coupling for directly connected to the housing 2901 of the tool. The NIM member 2900 further includes a pivot member 2905 connected to the base assembly 2903 and configured to provide a pivoting motion 2906 to an arm 2907 for selective engagement of an active assembly 2911 with a conductive portion of a bit 2909. As illustrated, the pivot member 2905 provides selective pivoting in a pivot direction 2506, such that the surgeon can selectively actuate the arm 2907 and active assembly 2911 in a direction 2908 to facilitate electrical connection of the active assembly 2911 with an electrically conductive portion of the bit 2909 when use of the NIM system is desired. As further illustrated, a wire 2913 is electrically connected to the base assembly 2903 and configured to transmit and electric signal to a remote monitoring system within the operating room.

Figure 30:
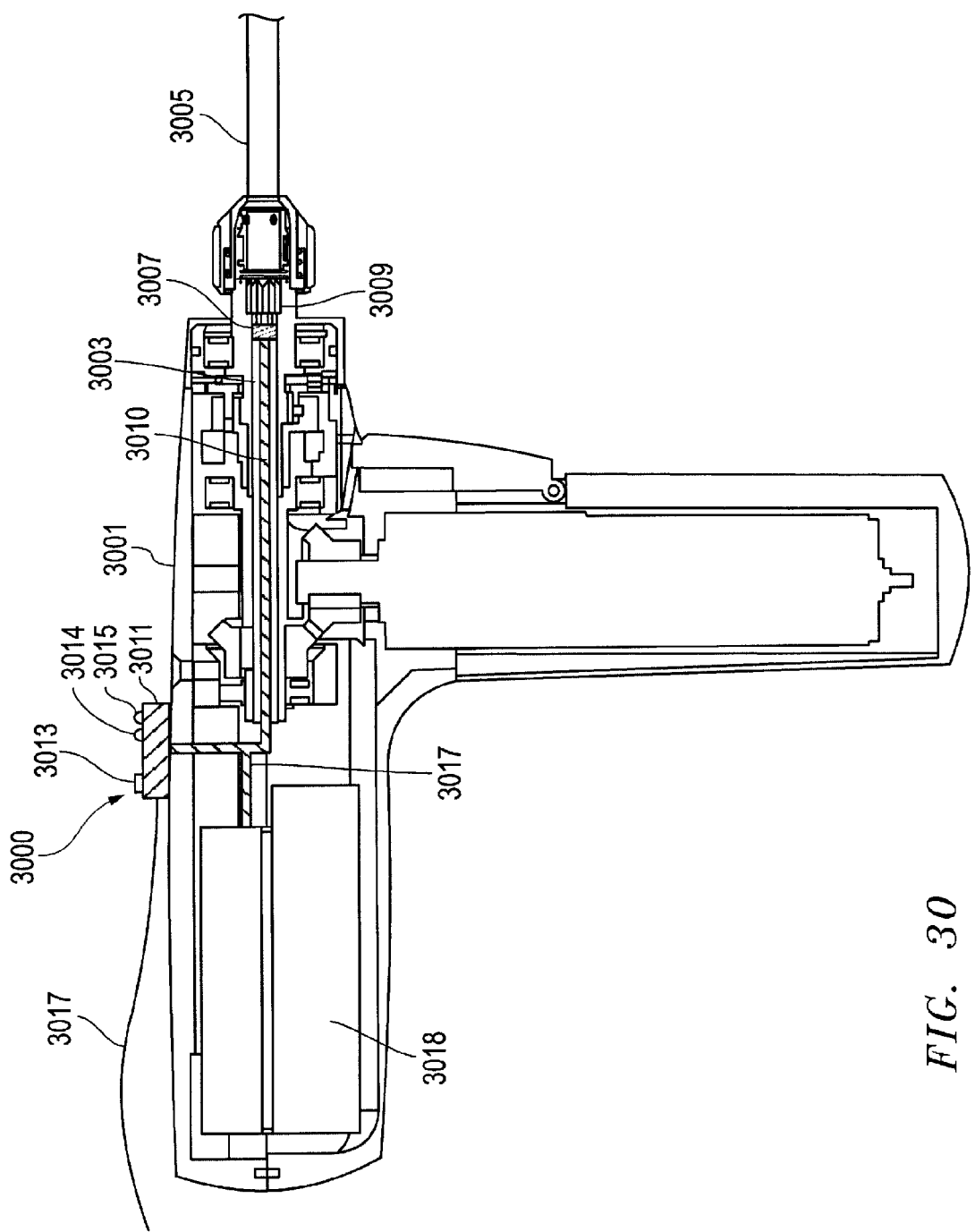
FIG. 30 includes a cross-sectional view of a surgical tool including a neural integrity monitoring (NIM) member in accordance with one embodiment.
Figure 31:
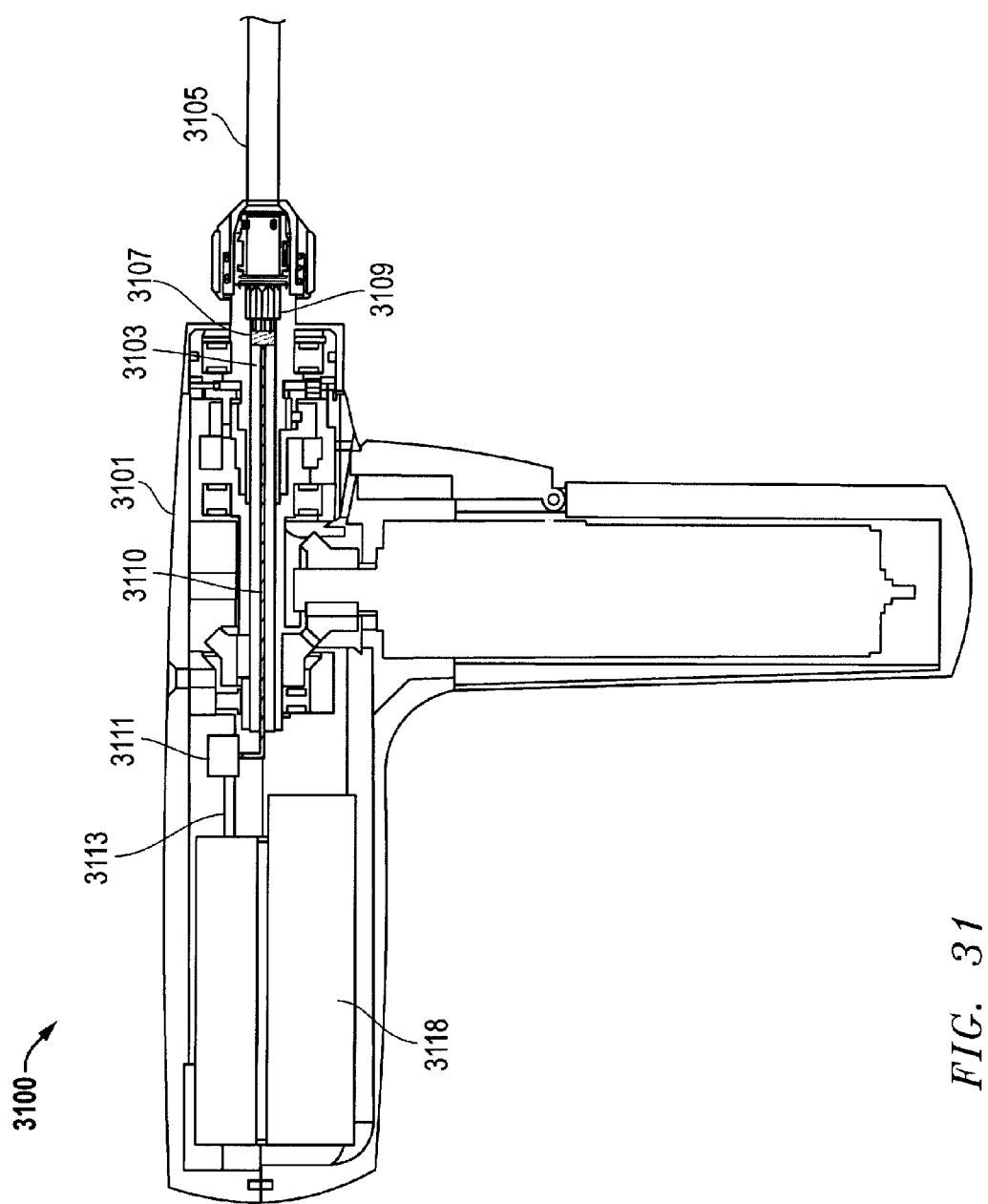
FIG. 31 includes a cross-sectional view of a surgical tool including a neural integrity monitoring (NIM) member in accordance with one embodiment.
Figure 32:
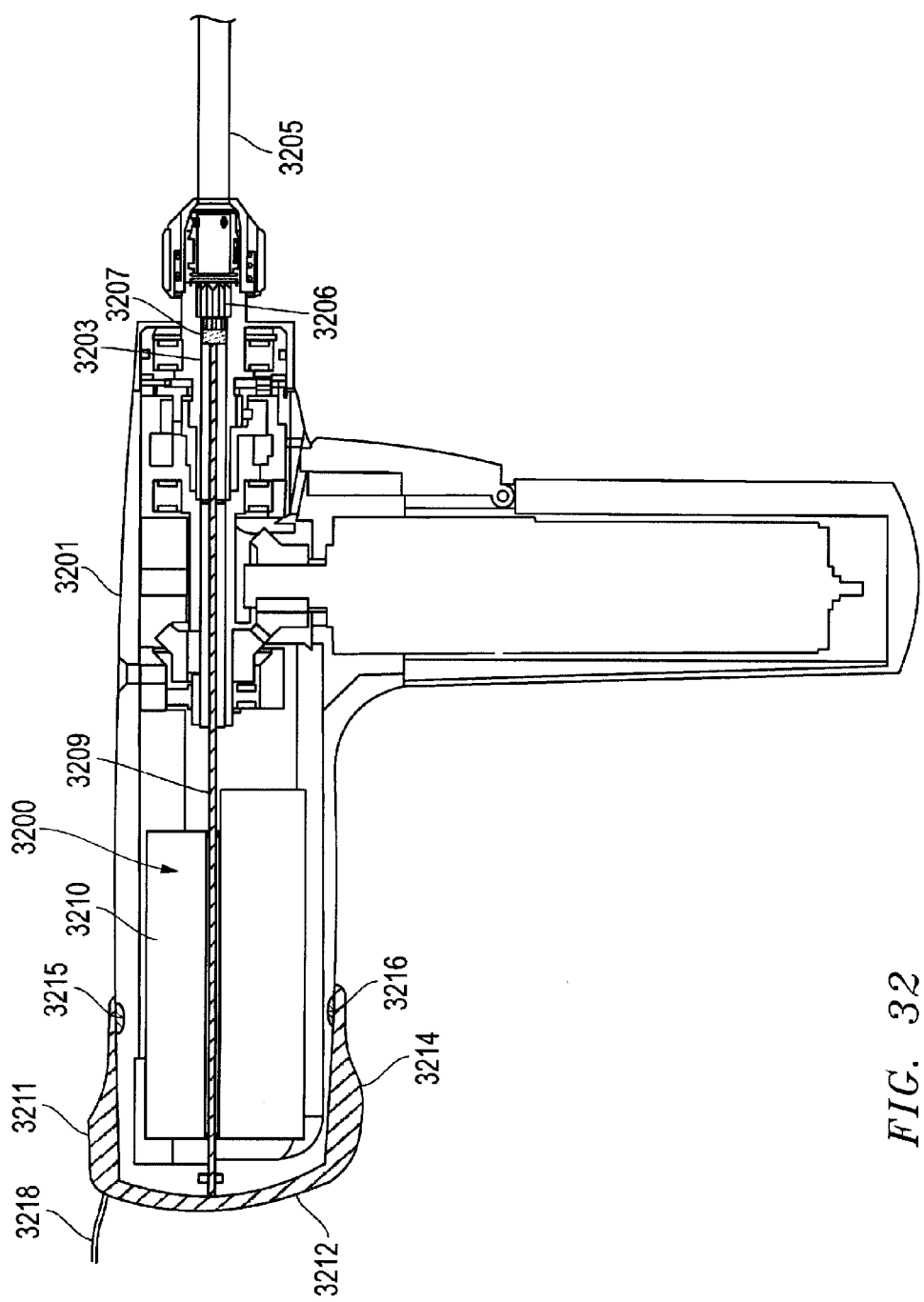
FIG. 32 includes a cross-sectional view of a surgical tool including a neural integrity monitoring (NIM) member in accordance with one embodiment.

Previous embodiments of the NIM member coupled to the tool have illustrated electrical connection of an active assembly to an electrically conductive portion of a bit external to the housing of the tool. As previously illustrated in FIGS. 25-29, generally, the electrical connection of the active assembly to a conductive portion of the bit is done in an external capacity wherein an arm and active assembly are extending exterior to the housing and connecting to an exterior portion of the bit. FIGS. 30-32 show an alternative embodiment, wherein at least a portion of the NIM member is placed within the interior of the housing of the tool.

FIG. 30 includes a cross-sectional view of a portion of the tool including a NIM member in accordance with an embodiment. As previously described herein, the tool can include a passage 3003 generally extending from a distal end to a proximal end of the housing 3001 and more particularly extending through a battery pack 3018. In accordance with a particular embodiment, the NIM member 3000 includes a base assembly 3011 connected to the housing 3001. In a more particular embodiment, the base assembly 3011 includes a conductive portion 3010 extending within the interior of the tool and more particularly extending along at least a portion of the passage 3003 within the interior of the tool.

In another embodiment, the NIM member 3000 includes an active assembly 3007 connected to the conductive portion 3010 and disposed within a portion of the passage 3003 within the interior of the tool. In accordance with a particular embodiment, the active assembly 3007 electrically connects the conductive portion 3010 to a conductive portion of a bit 3005. In a more particular embodiment, the active assembly 3007 is disposed within a portion of the passage 3003 abutting the quick-connect coupling 3009, such that upon engagement of the bit 3005 within the quick-connect coupling 3009 an electrical connection is formed between the active assembly 3007 and a conductive portion of the bit 3005.

In such embodiments utilizing a conductive portion 3010 disposed within a portion of the passage 3003, at least a portion of the passage 3003 can include an electrically insulating liner material to avoid electrical connection of the conductive portion 3010 with other electrical components within the interior of the tool. Moreover, an electrical liner may provide suitable electromagnetic shielding between the conductive portion 2010 and the active assembly 3007 with the motor within the housing 3001. Generally, at least the portion of the passage 3003 housing the conductive portion 3010 comprises the electrically insulating liner. However, in accordance with a more particular embodiment, the entire length of the passage 3003 may include an electrically insulating liner. Still, in another embodiment, the conductive portion can include an electrically insulating portion, such as a liner wrapping around the exterior for further electrical insulation.

In accordance with another embodiment, the base assembly 3011 can include a switch 3013 operable between an on state and an off stated for selective operation of the NIM member 3000. According to one embodiment, the base assembly 3011 can further include indicators 3014 and 3015, such as audible indicators or optical indicators, suitable for alerting the surgeon to neurological conditions of the patient. For example, indicator 3014 may be an LED providing one indication when the condition of the patient is normal and, alternatively, indicator 3015 may further include an LED providing a different indication when the condition of the patient has changed or is abnormal. Accordingly, the indicators 3014 and 3015 can aid the surgeon in carrying out a precise and safe surgical procedure.

As further illustrated, the NIM member 3000 further includes a wire 3017 extending from the base assembly 3011 and configured to transmit electrical signals between the active assembly 3007 and a remote monitoring system within the operating room. Moreover, in accordance with another embodiment, the base assembly 3011 can be connected to a power source. In accordance with one particular embodiment, the base assembly 3011 can be electrically connected to the battery pack 3018 via an electrical connection 3017. It will be appreciated that while the electrical connection 3017 is not illustrated as extending along the passage 3003, a suitable electrical connection between the base assembly 3011 and the battery pack 3018 may also include extension of an electrical connection 3017 within the passage 3003.

FIG. 31 includes a cross-sectional illustration of a surgical tool incorporating an NIM member in accordance with an embodiment. As illustrated, the NIM member 3100 includes a conductive portion 3110 disclosed within a portion of the passage 3103 within the interior of the housing 3101. As further illustrated, the NIM member 3100 further includes an active assembly 3107 electrically connected to the conductive portion 3110 and disposed within a portion of the passage 3103 proximate to the quick-connect coupling 3109 and configured to connect the active assembly 3107 with a conductive portion of a bit 3105.

In accordance with one particular embodiment, the electrically conductive portion 3110 is electrically connected to an integrated circuit 3111 disposed within the interior of the housing 3101 of the tool. In accordance with a particular embodiment, the integrated circuit 3111 is configured to transmit electrical signals wirelessly between the active assembly 3107 and a remote monitoring system. The integrated circuit 3111 can be connected to a power source, and more particularly, connected to the battery pack 3118 via an electrical connection 3113. While the integrated circuit 3111 is illustrated as being disposed within the housing 3101, in another suitable embodiment, the integrated circuit 3111 is connected to the housing 3101 in an external configuration. In still another particular embodiment, the integrated circuit 3111 may be partially disposed or wholly disposed within the passage 3103. In such embodiments, the integrated circuit 3111 may further include electromagnetic shielding to avoid electromagnetic disturbances from other electronic components within the tool.

FIG. 32 includes a cross-sectional illustration of a surgical tool including an NIM member in accordance with an embodiment. As illustrated, the NIM member 3200 includes a base assembly 3212 connected to the proximal end of the housing 3201 proximate to the battery pack 3210. The base assembly 3212 includes an upper arm 3211 and a lower arm 3214 configured to engage the housing 3201 and selectively couple or decouple the NIM member 3200 with the tool. In accordance with one particular embodiment, the base assembly 3212 and more particularly the upper arm 3211 and lower arm 3214 include flanges 3215 and 3216 configured to engage coupling locations on the housing 3201 and fixably connect the base assembly 3212 to the housing 3201.

As illustrated, the NIM member 3200 further includes an electrically conductive portion 3205 and active assembly 3207 disposed within a passage 3203. Moreover, according to this particular embodiment, the conductive portion 3205 extends for the entire length of the passage 3203. The active assembly 3207 is configured to engage the conductive portion of the bit 3205 at the quick-connect coupling 3206 such that upon engagement of the bit 3205 within the quick connect coupling 3206 an electrical connection is made between the active assembly 3207 and electrically conductive portion of the bit 3205. In another embodiment, the active assembly 3207 can include electrically coupling mechanisms, such as a brush or slip ring as previously described, suitable for facilitating transmission of electrical signals between the conductive portion of the bit 3205 and a remote monitoring system.

In certain embodiments, the conductive portion 3209 and the active assembly 3207 are rigid components suitable for selective insertion by the surgeon through the length of the passage 3203 for electrical connection at the quick-connect coupling 3206 with a conductive portion of a bit 3205. As such, when a surgeon wishes to use a NIM system for a surgical procedure, the NIM member 3200 can be engaged on the tool such that the conductive portion 3209 and active assembly 3207 are inserted into the passage 3203 by the surgeon at the proximal end of the housing until the arms 3211 and 3214 engage the housing 3201 and are rigidly fixed in place via flanges 3215 and 3216. As further illustrated, the NIM member 3200 further includes a wire 3218 configured to carry an electrical signal from the active assembly 3207 to a remote monitoring system within the operating room.

Previous embodiments have shown incorporation of navigation enabling members or neural integrity monitoring members with a surgical tool. FIGS. 33-36 illustrate a combination of navigation enabling members and neural integrity monitoring members in connection with the tool. The following configurations illustrated in FIGS. 33-36 are particularly suited to the tool as described herein given the particular design of the tool and its intended use.

Figure 33:
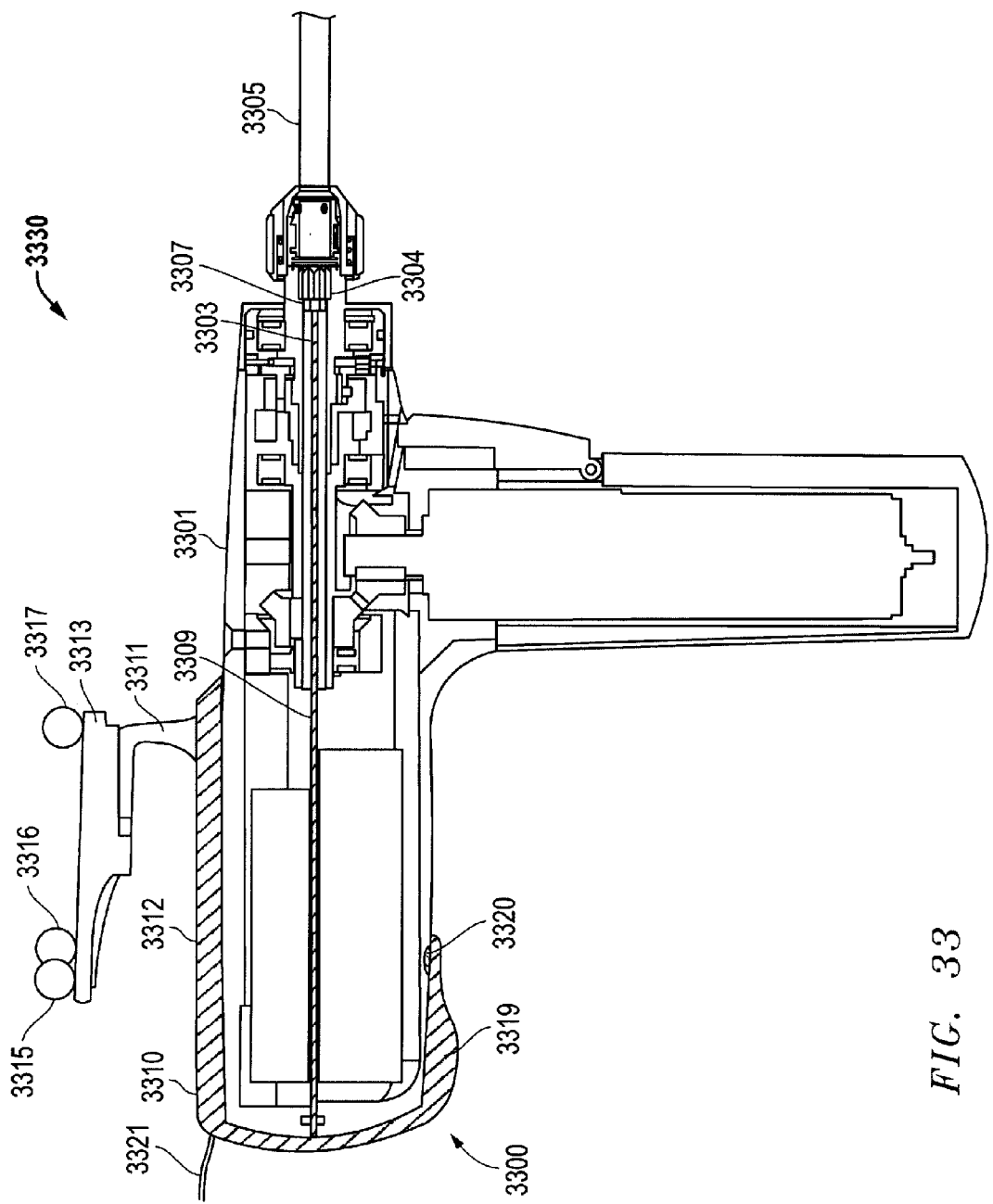
FIG. 33 includes a cross-sectional view of a surgical tool including a neural integrity monitoring (NIM) member and a navigation enabling member in accordance with one embodiment.

FIG. 33 includes a cross-sectional illustration of the tool incorporating a navigation enabling member and a NIM member in accordance with an embodiment. As illustrated, the NIM member 3300 includes a base assembly 3310 including an upper arm 3312 and a lower arm 3319 connected to the housing 3301 of the tool. In accordance with a particular embodiment, the arm 3319 extending along the lower portion of the housing 3301 includes a flange 3320 configured to engage a coupling portion or depression within the housing 3301 and fixably attach the base assembly 3310 to the housing 3301. The NIM member 3300 further includes a conductive portion 3309 and active assembly 3307 extending the length of the passage 3303 from the proximal end of the housing 3301 to the distal end of the housing 3301, such as previously illustrated in FIG. 32. The NIM member 3300 further includes a wire 3321 extending from the base assembly 3310 and configured to electrically connect the active assembly 3307 with a remote monitoring system.

As further illustrated, a tool can include a navigation enabling member 3330 connected to the base assembly 3310 and more particularly, the upper arm 3312 of the NIM member 3300. In accordance with one embodiment, the navigation enabling member 3330 includes a base 3311 directly connected to the arm 3312. In accordance with another embodiment, the navigation enabling member 3330 further includes an upper portion 3313 supporting reflecting structures 3315, 3316 and 3317 that are configured to reflect radiation emitted by a detector and facilitate triangulation of the tool within the operating room. The combination of the NIM member 3300 and the navigation enabling member 3330 facilitates improved computer assisted surgeries wherein the surgeon is capable of locating and orienting the tool within the operating room as well as monitoring the neural status of the patient during delicate procedures such as spinal surgeries.

Figure 34:
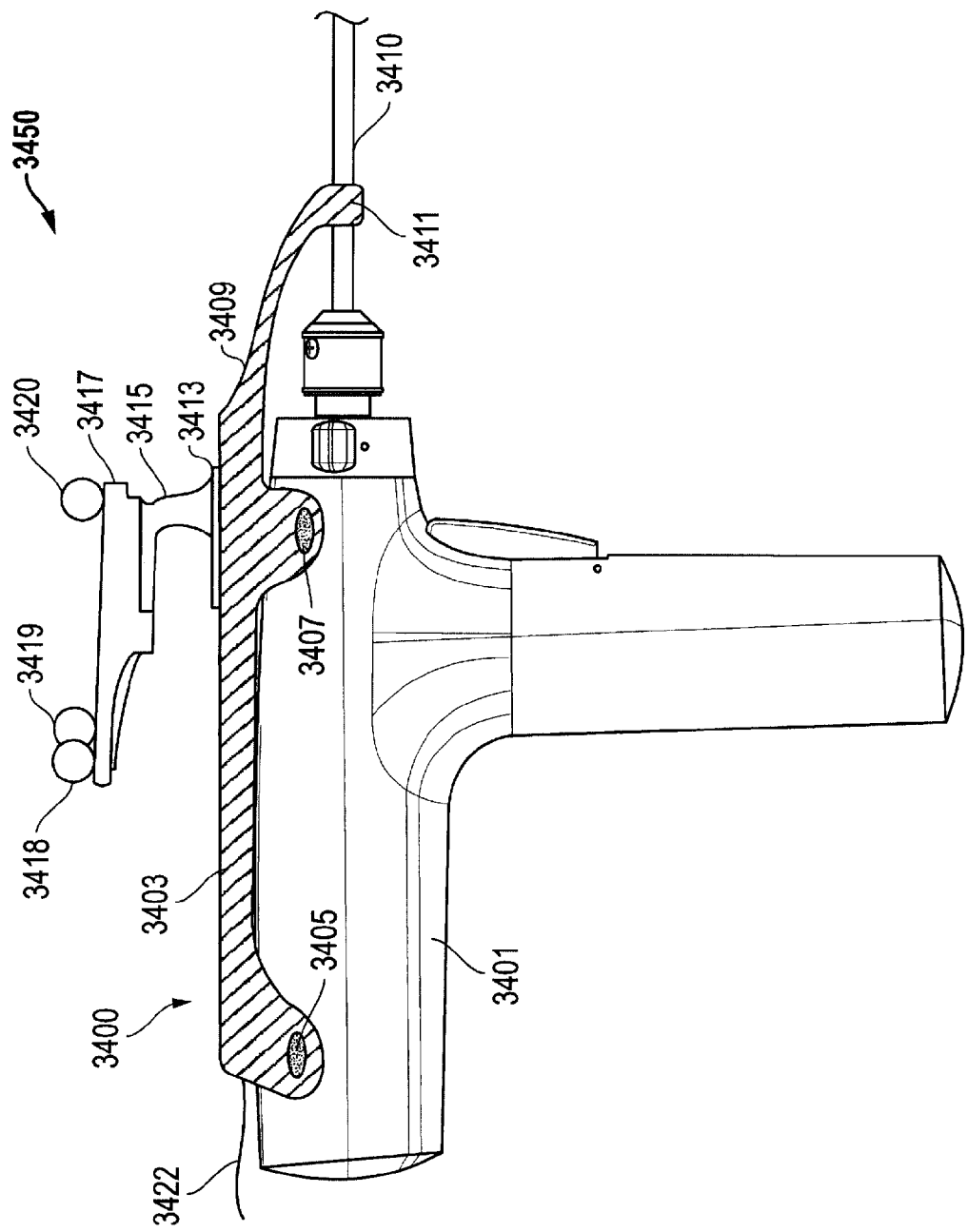
FIG. 34 includes a cross-sectional view of a surgical tool including a neural integrity monitoring (NIM) member and a navigation enabling member in accordance with one embodiment FIG. 35 includes a side view of a surgical tool including a neural integrity monitoring (NIM) member and reflecting structures for navigation enabling capabilities in accordance with one embodiment.

FIG. 34 includes a side view of a tool including a NIM member and a navigation enabling member in accordance with an embodiment. As illustrated, the NIM member 3400 includes a base assembly 3403 including those components substantially as illustrated in FIG. 27. Accordingly, the base assembly 3403 includes couplings 3405 and 3407 configured to attach the base assembly 3403 to the housing 3401. The NIM member 3400 further includes an arm 3409 extending from the base assembly 3403, and an active assembly 3411 extending from a distal end of the arm 3409 configured to electrically connect the active assembly 3411 with a conductive portion of the bit 3410. The NIM member 3400 further includes a wire 3422 extending from the base assembly 3403 and configured to electrically connect the active assembly 3411 to a remote monitoring system within the operating room.

In accordance with a particular embodiment, the tool further includes a navigation enabling member 3450 connected to the NIM member 3400. In accordance with a particular embodiment, the navigation enabling member 3450 includes a coupling 3413 connected to the base assembly 3403. In another embodiment, the navigation enabling member further includes a base 3415 connected to the coupling 3413. The navigation enabling member in another embodiment further includes an upper portion 3417 connected to the base 3415 and supporting reflecting structures 3418, 3419, and 3420. In accordance with an embodiment, the coupling 3413 can utilize coupling designs previously illustrated and described in FIGS. 14-19. Moreover, while not illustrated, it will be appreciated that the coupling 3413 can further be pivoted, rotated, or translated in accordance with such NAV members described herein. Accordingly, the coupling 3413 may further include members as illustrated in FIGS. 20-24 to facilitate movement of the navigation enabling member 3450.

Figure 35:
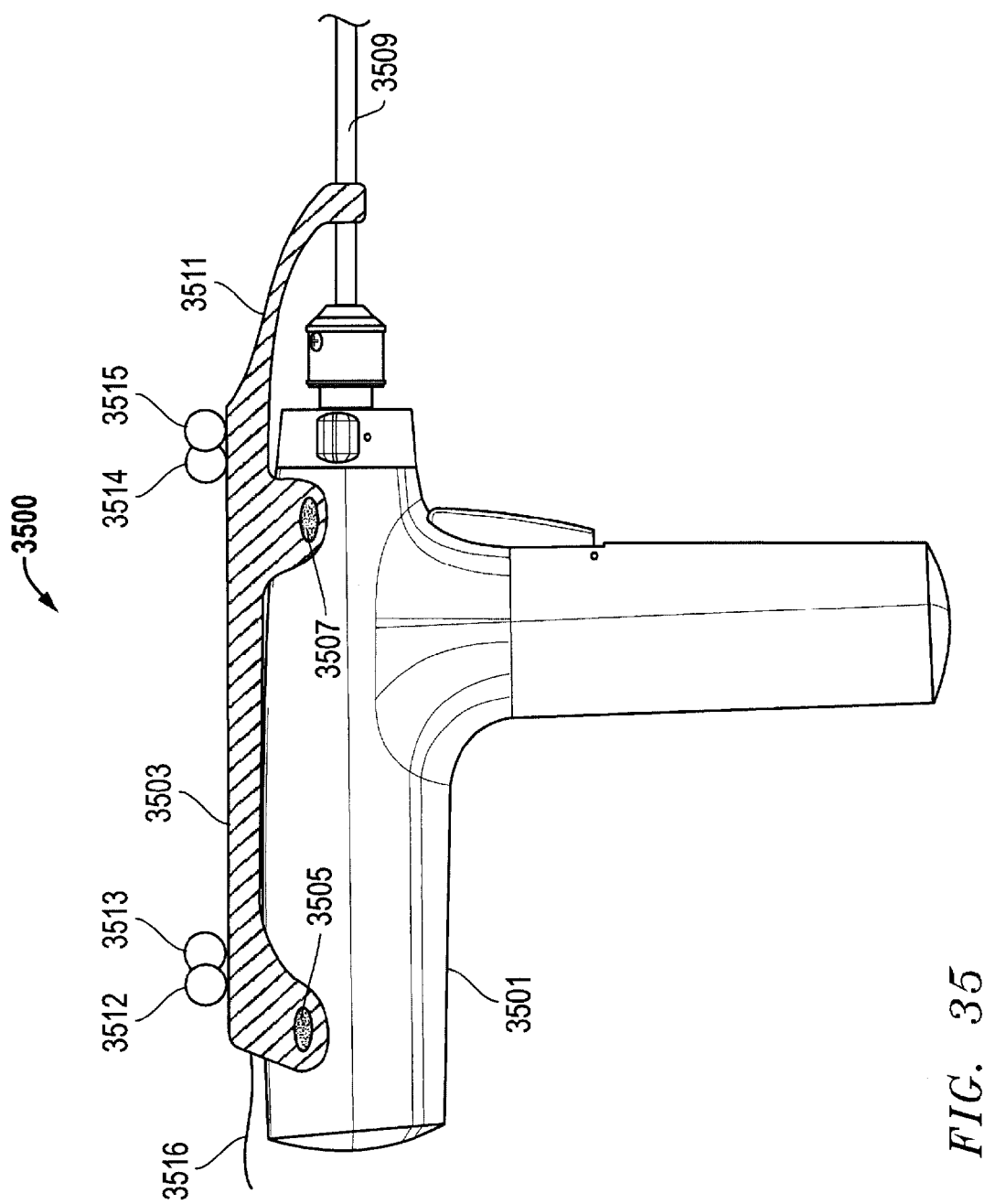

FIG. 35 includes a side view of a surgical tool including a NIM member and reflecting structures in accordance with an embodiment. In particular, FIG. 35 illustrates a particular combination of a NIM member and navigation enabling structures facilitating a low profile structure for improved field of view around the tool suitable for conducting precise surgical procedures. Accordingly, the NIM member 3500 includes those portions previously described in accordance with FIG. 34. In particular, the NIM member 3500 includes a base assembly 3503 directly connected to the housing 3501. Connection of the base assembly 3503 to the housing 3501 is facilitated by couplings 3505 and 3507. The NIM member 3500 further includes an arm 3511 connected to the base assembly 3505 and an active assembly 3513 connected to a distal end of the arm 3511 configured to electrically connect to a conductive portion of a bit 3509. Moreover, the NIM member 3500 further includes a wire 3516 configured to electrically connect the active assembly with a remote monitoring system.

According to an alternative embodiment, the NIM member further includes reflecting structures 3512, 3513, 3514, and 3515 (3512-3515) directly connected to the base assembly 3503. In an alternative embodiment, as compared to that illustrated in FIG. 34, the reflecting structures 3512-3515 are directly connected to the base assembly 3503 of the NIM member 3500 removing the coupling and base of the navigation enabling member. Such a design facilitates a low profile structure facilitating an improved field of view around the tool. It will be appreciated, that the reflecting structures 3512-3515 may further be replaced by active structures such as LEDs embedded within the base assembly 3503 further reducing the profile of the combined NIM member 3500 with navigation enabling structures.

Figure 36:
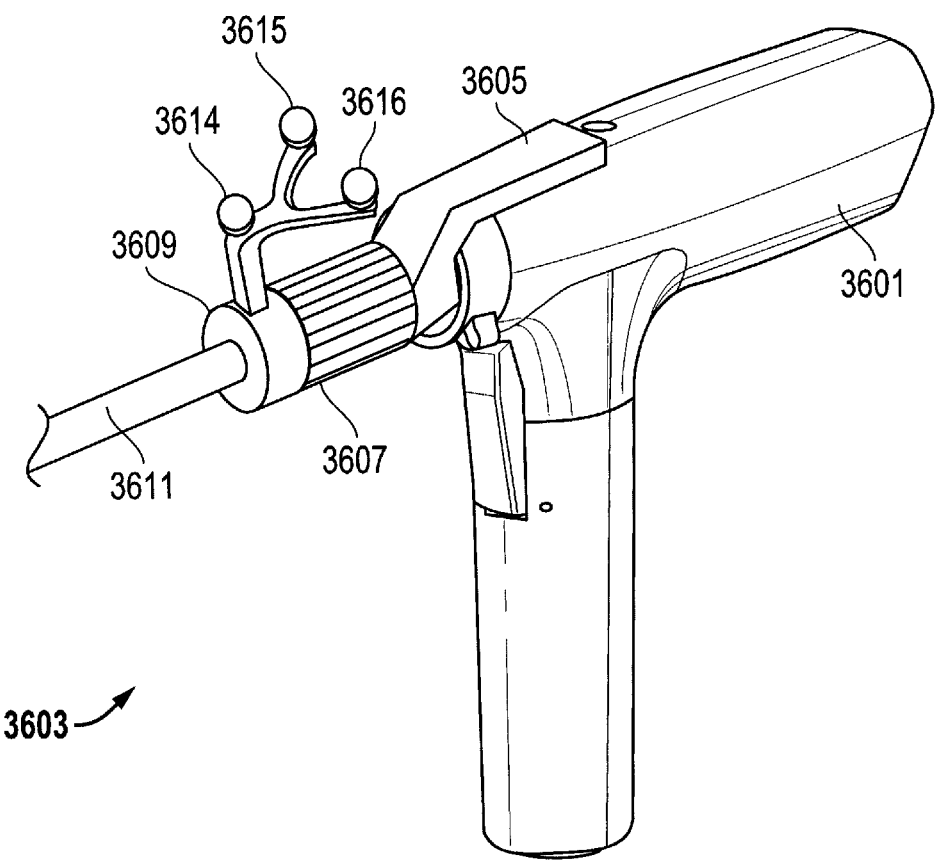
FIG. 36 includes a perspective view of a surgical tool including a neural integrity monitoring (NIM) member and a navigation enabling member in accordance with one embodiment.

Referring to FIG. 36, a perspective view of a surgical tool including a navigation enabling member and NIM member is illustrated in accordance with an embodiment. As illustrated, the combined NIM/NAV structure of 3603 includes a base assembly 3605 connected to the distal end of the housing 3601 proximate to the chuck. In one embodiment, a portion of the base assembly 3605 extends along a length of the housing 3601 and can be coupled to the housing 3601 to rigidly fix the NIM/NAV structure 3603 relative to the housing 3601. The NIM/NAV structure 3603 further includes an active assembly 3607 connected to the base assembly 3605 and configured to provide an electrical connection to a conductive portion of a bit 3611. In accordance with one embodiment, the active assembly 3607 may be freely rotatable in conjunction with the rotation of the bit 3611, while the base assembly 3605 and member 3609 may not necessarily rotate in conjunction with the active assembly 3607 and the bit 3611.

As further illustrated, the NIM/NAV structure 3603 includes a member 3609 connected to the active assembly 3607 and supporting a base 3608 that in turn supports reflective structures 3614, 3615, and 3616. In accordance with one embodiment the member 3609 is a non-rotating member. In accordance with another embodiment, the member 3609 may be rotatable between a series of set positions such that the base 3608 and reflecting structures 3614-3616 are properly oriented for identification by a detector within the operating room. Moreover, in still another embodiment, the member 3609 may be freely rotatable along with the active assembly 3607 such that the base and reflecting structures 3614-3616 are freely rotatable during rotation of the bit 3611. Free rotation of the base 3608 and reflecting structures 3614-3616 may not be problematic with respect to positioning of the tool as the base 3608 and reflecting structures 3614-3616 are a set distance away from the virtual axis defined by the longitudinal access of the bit 3611. It will be appreciated, in accordance with another embodiment, active structures such as LEDs may be provided of the NIM/NAV structure 3603 to further reduce the profile of the tool and increase visibility of the surgeon.

Embodiments provided herein represent a departure from the state of the art. In particular reference to tapping and driving bone screws and other implants, the state of the art still includes the use of manual tools often resulting in surgeon fatigue and inefficiency, which in turn results in more hazardous procedures. For example, when operating a manual tool for driving a threaded member, the natural motion of the body causes a procession or wobble of the tool in a conical shape. The procession or wobbling action is inefficient increasing surgeon fatigue and also increases the risk of injury to the patient leading to improper placement of the implant and the additional forces on the implant due to the wobbling may fatigue or weaken the implant. By contrast, the surgical tool provided herein includes a combination of features making such procedures more efficient and safer. The combination of features include, among other things, use of a power tool having particular dimensions suitable for one-handed use in sterile environments, a battery pack particularly designed for the tool and integration with its components, a passage extending through the tool having specific features and uses, a ratcheting mechanism, a failsafe switch, sealed portions within the housing, and use of autoclavable materials. Moreover, other features of the present embodiments include selective coupling and decoupling of portions of the output shaft depending upon the source of the torque to save the motor and allow for greater manual reversing torque to be applied by passing the torque to the housing as opposed to the motor. The combination of such features provide a power tool capable of reducing surgeon fatigue by making surgical procedures more efficient and less physically demanding and in turn reducing potential injury to patients and the surgeon.

Additionally, the tool is capable of integration with computer assisted surgery technologies, including NAV and NIM systems. Unlike conventional surgical tools, the integration of the NAV and NIM systems provided herein are particularly designed for the tool based upon its design and intended purpose. The surgical tool is a hand-held power tool, capable of providing power to perform delicate procedures, and particularly designed through empirical research to afford a surgeon proper tactile feedback, the NAV and NIM systems have been integrated into the design such that their impact on the tool is reduced and the surgeon's vision and feel are not compromised by the addition of such assemblies. Moreover, the incorporation of the NAV and NIM systems with the tool described herein utilize particular physical and electrical connections. Integration of NAV and NIM systems can be further enhanced by certain features of the tool, for example, the size of the housing and the passage.

According to one embodiment, a surgical tool can include a fail safe switch coupled to the housing and moveable between an off position and an on position, wherein the off position electrically decouples the motor from the battery. According to another embodiment, the surgical tool can include a fail safe switch coupled to the housing and moveable between an off state and an on state, wherein the off state decouples the output shaft from the motor. Use of the failsafe switch is suitable for single fault tolerance specifications desirable for tools used in sensitive applications, such as surgery.

As such, with regard to the fail safe switch, in light of particular embodiments provided herein directed to one-handed operation of the surgical tool, generally the fail safe switch is coupled to the housing in a position suitable for simultaneous operation with the trigger 1001. As such, in one embodiment, the fail safe trigger is simultaneously operable with the trigger 1001 with the first hand of the operator.

According to a first aspect, a tool for use during surgery includes a housing having a distal end and a proximal end, a motor disposed within the housing, and an output shaft having a proximal end coupled to the motor and a distal end extending from the distal end of the housing. The tool further includes a battery pack contained within the housing, and a passage extending from the distal end to the proximal end of the housing through the output shaft and the battery pack, wherein the passage is defined by an interior surface of the output shaft and a channel through the battery.

According to one embodiment of the first aspect, the tool further includes a sealed compartment within the housing. In a particular embodiment, the sealed compartment comprises the motor.

According to another embodiment, the passage has a generally circular cross-sectional contour including a diameter of at least about 1 mm. In a more particular embodiment, the diameter of the passage is not greater than about 10 mm. According to another embodiment of the first aspect, the passage has a length of at least about 10 cm. In a more particular embodiment, the passage has a length of not greater than about 25 cm. In another more particular embodiment, a portion of the passage extending through the battery pack has a length of at least about 5 cm.

In one embodiment of the first aspect, the passage further includes an electrically insulating liner extending for a portion of the passage. According to another embodiment, the electrically insulating liner extends for the entire length of the passage. In one particular embodiment, the electrically insulating liner defines the inner surface of the passage. In a more particular embodiment, the passage extends along a single axis from the distal end to the proximal end.

According to another embodiment of the first aspect, the tool includes a handle coupled to the housing and extending from the housing. In one particular embodiment, the handle extends from the housing and defines a non-orthogonal angle between the housing and the handle.

In accordance with one embodiment, the tool further includes a ratcheting mechanism coupled to the output shaft. In accordance with another embodiment, the tool further includes a switch coupled to the housing and electrically coupled to the motor, wherein the switch comprises a forward position and a reverse position, wherein the forward position is configured to actuate the motor in a forward direction and the reverse position is configured to actuate the motor in a reverse direction that is a direction opposite of the forward direction. In one particular embodiment, the switch further includes a neutral position. In another particular embodiment, the tool further includes a first optical indicator electrically coupled to the switch in the forward position and a second optical indicator electrically coupled to the switch in the reverse position.

In another embodiment of the first aspect, the tool further includes an anti-backdrive mechanism coupled to the output shaft and the housing. In another embodiment, the ratchet mechanism is decoupled from the output shaft in the reverse position. According to another embodiment of the first aspect, the motor is disposed within the handle. In one particular embodiment, the motor is reversible. In another particular embodiment, the motor is coupled to a planetary gear set. In a still more particular embodiment, the motor is coupled to a lower bevel gear.

In accordance with an embodiment of the first aspect, the battery pack includes multiple power cells. In accordance with another embodiment, the multiple power cells are arranged around the passage. In still another more particular embodiment, the battery pack has a longitudinal axis and a substantially triangular cross-sectional contour including three corners, wherein the power cells are disposed within the corners of the battery pack and the passage extends substantially along the longitudinal axis.

According to an embodiment of the first aspect, the tool further includes a trigger for engaging the motor, wherein the trigger is magnetically operated. In one particular embodiment, the trigger further includes a failsafe switch disposed on the trigger and moveable between an on position and an off position. In another particular embodiment, the tool further includes a trigger coupled to the handle and operable with a first hand of an operator, and a failsafe switch coupled to the housing, wherein the failsafe switch is simultaneously operable with the trigger with the first hand of the operator. In still another particular embodiment, the tool further includes a failsafe switch coupled to the housing and moveable between an off position and an on position, wherein the off position electrically decouples the motor from the battery. In accordance with another particular embodiment, the tool further includes a failsafe switch coupled to the housing and moveable between an off state and an on state, wherein the off state decouples the output shaft from the motor.

Still, according to another embodiment of the first aspect, the output shaft further comprises a chuck coupled to the distal end. In one embodiment, the chuck includes a quick-connect adapter. In another embodiment, the tool further includes a bit shaft including a proximal end coupled to the chuck of the output shaft and a working end opposite the proximal end. In still another embodiment, the working end comprises a tapper bit head. In another embodiment, the working end comprises a screwdriver bit head.

According to another embodiment, the tool comprises shielding around the motor to reduce electromagnetic interference. In one particular embodiment, the electromagnetic shielding includes metal mesh.

In another embodiment, the tool further includes a torque limiter comprising a microprocessor coupled to the motor and the battery. In one particular embodiment, the torque limiter is programmable by the user. In another particular embodiment, the tool further includes a torque limiter coupled to the output shaft.

According to a second aspect a surgical tool for affixing orthopedic anchors in bone includes an autoclavable housing comprising a distal end, a proximal end, and a handle extending from the housing between the distal end and the proximal end at an angle to a longitudinal axis of the housing, wherein the housing comprising a sealed portion containing a motor. The surgical tool further includes an output shaft extending along the longitudinal axis of the housing and coupled to the motor, and a ratcheting mechanism coupled to the output shaft. According to one embodiment of the second aspect, the sealed portion comprises a first o-ring abutting a portion of the housing and a second o-ring abutting a second portion of the housing.

According to a third aspect a surgical tool for affixing orthopedic anchors in bone includes a housing comprising a distal end, a proximal end opposite of the distal end, and a housing length defined as the distance between the proximal end and the distal end. The surgical tool of the third aspect further includes a motor, an output shaft within the housing having a proximal end and a distal end opposite the proximal end, wherein the proximal end is coupled to the motor, and a chuck having a distal end and a proximal end opposite the distal end coupled to the distal end of the output shaft. The surgical tool of the third aspect further includes a handle coupled to the housing and extending at an angle from the housing between the distal end and the proximal end, the handle having a front surface including a trigger and a back surface opposite the front surface, wherein a cradle distance defined as a distance between the back surface and the proximal end of the chuck is not greater than about 50% of the housing length.

In accordance with a particular embodiment of the third aspect, the cradle distance is within a range between about 30% and about 45% of the length of the housing. In another particular embodiment, the handle is closer to the distal end of the housing than the proximal end of the housing. In still another particular embodiment, the handle has a length defining a central longitudinal axis, wherein the distance between the central longitudinal axis and the distal end of the housing is not greater than about 30% of the housing length. According to another embodiment of the third aspect, the distance between the central longitudinal axis and the distal end of the housing is within a range between about 20% and about 30% of the housing length. As such, in one particular embodiment, the handle has a length of at least about 75% of the length of the housing.

The above-disclosed subject matter is to be considered illustrative, and not restrictive, and the appended claims are intended to cover all such modifications, enhancements, and other embodiments, which fall within the true scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A tool for use during surgery comprising:
a housing comprising a distal end and a proximal end,
a motor disposed within the housing;
an output shaft having a proximal end connected to the motor and a distal end;
a battery pack contained within the housing;
a segmented passage comprising a first portion disposed within an interior of the output shaft and a second portion extending through an interior of the battery pack, the first portion extending parallel to the second portion, the first and second portions being axially separated by an opening, and
an assembly configured to select between forward and reverse drive positions, the assembly comprising a sleeve having an inner surface defining a lumen, the lumen having a member rotatably disposed therein, the member comprising a first pin that faces toward the battery pack, the first in being configured to engage openings in an anti-backdrive assembly of the tool, thereby acting as a clutch configured to lock pawls within the anti-backdrive assembly in a particular location, the member comprising an inner surface defining a channel, the output shaft extending through the lumen and the channel.

2. The tool of claim 1, further comprising a sealed compartment, wherein the motor is disposed within the sealed compartment.

3. The tool of claim 1, wherein the passage has a generally circular cross-sectional contour including a diameter of at least about 1 mm.

4. The tool of claim 1, wherein the passage has a length of at least about 10 cm.

5. The tool of claim 1, wherein the passage further comprises an electrically insulating liner extending for a portion of the passage.

6. The tool of claim 1, further comprising a ratcheting mechanism connected to the output shaft.

7. The tool of claim 6, further comprising a switch connected to the housing and electrically connected to the motor, wherein the switch comprises a forward position and a reverse position, wherein the forward position is configured to actuate the motor in a forward direction and the reverse position is configured to actuate the motor in a reverse direction that is a direction opposite of the forward direction.

8. The tool of claim 7, further comprising an anti-backdrive mechanism connected to the output shaft and the housing.

9. The tool of claim 8, wherein the ratchet mechanism is decoupled from the output shaft in the reverse position.

10. The tool of claim 1, wherein the battery pack comprises multiple power cells.

11. The tool of claim 1, further comprising:
a trigger operable with a hand of an operator; and
a failsafe switch connected to the housing, wherein the failsafe switch is simultaneously operable with the trigger with the hand of the operator, and wherein the failsafe switch prevents operation of the motor without the hand of the operator.

12. The tool of claim 11, wherein the failsafe switch is disposed on the surface of the trigger and configured to detect the presence of a user's finger operating the trigger.

13. The tool of claim 12, wherein the failsafe switch includes a capacitive member configured to detect the presence of a user at the surface of the failsafe switch.

14. The tool of claim 11, wherein the failsafe switch and the trigger are distinct.

15. The article of claim 14, wherein the trigger is decoupled from the motor and the motor is in an off position when the failsafe switch is disengaged.

16. The tool of claim 1, wherein the first portion is coaxial with the second portion.

17. The tool of claim 1 wherein the member comprises a second pin extending parallel to the first pin and facing toward the batter pack, the second pin being configured to selectively engage openings within the anti-backdrive assembly to engage or disengage ratcheting capabilities of a ratcheting mechanism of the tool.

18. The tool of claim 17, wherein the second pin has a maximum length that is less than that of the first pin.

19. The tool of claim 18, wherein the first pin comprises three pins and the second pin comprises three pins.

20. A surgical tool for implanting devices within the body comprising:
an autoclavable housing comprising a distal end, a proximal end, and a handle extending from the housing between the distal end and the proximal end at an angle to a longitudinal axis of the housing, wherein the housing comprising a sealed portion containing a motor;
a battery pack contained within the housing;
an output shaft extending along the longitudinal axis of the housing and connected to the motor;
a segmented passage comprising a first portion disposed within an interior of the output shaft and a second portion extending through an interior of the battery pack, the first portion extending parallel to the second portion, the first and second portions being axially separated by an opening; and
a ratcheting mechanism connected to the output shaft
an assembly configured to select between forward and reverse drive positions, the assembly comprising a sleeve having an inner surface defining a lumen, the lumen having a member rotatably disposed therein, the member comprising a first pin that faces toward the battery pack, the first in being configured to engage openings in an anti-backdrive assembly of the tool, thereby acting as a clutch configured to lock pawls within the anti-backdrive assembly in a particular location, the member comprising an inner surface defining a channel, the output shaft extending through the lumen and the channel.

21. The tool of claim 20, wherein the sealed portion comprises a first gasket abutting a portion of the housing and a second gasket abutting a second portion of the housing.

22. A surgical tool for implanting devices within the body comprising:
a housing comprising a distal end, a proximal end opposite of the distal end, and a housing length defined as the distance between the proximal end and the distal end;
a battery pack contained within the housing;
a motor;
an output shaft having a proximal end and a distal end opposite the proximal end, wherein the proximal end is connected to the motor;
a segmented passage comprising a first portion disposed within an interior of the output shaft and a second portion extending through an interior of the battery pack, the first portion extending parallel to the second portion, the first and second portions being axially separated by an opening;
a chuck having a distal end and a proximal end opposite the distal end connected to the distal end of the output shaft; and a handle connected to the housing and extending at an angle from the housing between the distal end and the proximal end, the handle having a front surface including a trigger and a back surface opposite the front surface, wherein a cradle distance defined as a distance between the back surface and the proximal end of the chuck is not greater than about 50% of the housing length an assembly configured to select between forward and reverse drive positions, the assembly comprising a sleeve having an inner surface defining a lumen, the lumen having a member rotatably disposed therein, the member comprising a first pin that faces toward the battery pack, the first pin being configured to engage openings in an anti-backdrive assembly of the tool, thereby acting as a clutch configured to lock pawls within the anti-backdrive assembly in a particular location, the member comprising an inner surface defining a channel, the output shaft extending through the lumen and the channel.

23. The tool of claim 22, wherein the cradle distance is within a range between about 30% and about 45% of the length of the housing.

24. The tool of claim 22, wherein the handle is closer to the distal end of the housing than the proximal end of the housing.

* * * * *